United States Patent
Waddell et al.

(10) Patent No.: US 6,849,636 B2
(45) Date of Patent: Feb. 1, 2005

(54) TRIAZOLE DERIVATIVES AS INHIBITORS OF 11-BETA-HYDROXYSTEROID DEHYDROGENASE-1

(75) Inventors: Sherman T. Waddell, Westfield, NJ (US); Gina M. Santorelli, Oceanport, NJ (US); Milana M. Maletic, Summit, NJ (US); Aaron H. Leeman, Westfield, NJ (US); Xin Gu, Scotch Plains, NJ (US); Donald W. Graham, Mountainside, NJ (US); James M. Balkovec, Martinsville, NJ (US); Susan D. Aster, Teaneck, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/739,716

(22) Filed: Dec. 18, 2003

(65) Prior Publication Data

US 2004/0133011 A1 Jul. 8, 2004

Related U.S. Application Data

(60) Provisional application No. 60/503,410, filed on Sep. 16, 2003, provisional application No. 60/458,592, filed on Mar. 28, 2003, and provisional application No. 60/435,074, filed on Dec. 20, 2002.

(51) Int. Cl.$^7$ ................. A61K 31/4196; C07D 249/08; C07D 401/04; C07D 403/04; C07D 413/02
(52) U.S. Cl. ................. 514/256; 514/311; 514/340; 514/364; 514/365; 514/383; 544/333; 546/167; 546/272.4; 548/131; 548/203; 548/266.2; 548/266.4; 548/266.8; 548/267.2; 548/267.8; 548/269.4
(58) Field of Search .................. 544/333; 546/167; 546/272.4; 548/266.2, 266.4, 266.8, 267.2, 267.8, 269.4, 131, 203; 514/256, 311, 340, 364, 365, 383

(56) References Cited

U.S. PATENT DOCUMENTS 6,730,690 B2 * 5/2004 Olson et al. ................ 514/383

FOREIGN PATENT DOCUMENTS

| WO | WO 01/90092 | 11/2001 |
|---|---|---|
| WO | WO 01/90094 | 11/2001 |
| WO | WO 02/056891 | 7/2002 |
| WO | WO 02/076435 | 10/2002 |
| WO | WO 03/043999 | 5/2003 |
| WO | WO 03/044000 | 5/2003 |
| WO | WO 03/044009 | 5/2003 |
| WO | WO 03/059267 | 7/2003 |
| WO | WO 03/065983 | 8/2003 |
| WO | WO 03/086410 | 10/2003 |
| WO | WO 03/104208 | 12/2003 |
| WO | WO 2004/011410 | 2/2004 |

OTHER PUBLICATIONS

Walker, Brian, R., "11β–Hydroxysteroid dehydrogenase Type 1 as a novel therapeutic target in metabolic and neurodegenerative disease", Expert Opinion Therapeutic Targets, vol. 7(6), pp. 771–783 (2003).

* cited by examiner

Primary Examiner—Fiona T. Powers
(74) Attorney, Agent, or Firm—Richard C. Billups; Philippe L. Durette; Melvin Winokur

(57) ABSTRACT

Triazole derivatives of structural formula I are selective inhibitors of the 11β-hydroxysteroid dehydrogenase-1. The compounds are useful for the treatment of diabetes, such as noninsulin-dependent diabetes (NIDDM), hyperglycemia, obesity, insulin resistance, dyslipidemia, hyperlipidemia, hypertension, Metabolic Syndrome, and other symptoms associated with NIDDM.

49 Claims, No Drawings

TRIAZOLE DERIVATIVES AS INHIBITORS OF 11-BETA-HYDROXYSTEROID DEHYDROGENASE-1

This application claims benefit to U.S. Provisional application Nos. 60/435,074 filed on Dec. 20, 2002, 60/458,592 filed on Mar. 28, 2003, and 60/503,410 filed on Sep. 16, 2003.

FIELD OF THE INVENTION

The present invention relates to triazole derivatives as inhibitors of the enzyme 11-beta-hydroxysteroid dehydrogenase Type I (11β-HSD-1 or HSD-1) and methods of treatment certain conditions using such compounds. The compounds of the present invention are useful for the treatment of diabetes, such as non-insulin dependent Type 2 diabetes mellitus (NIDDM), insulin resistance, obesity, lipid disorders, hypertension, and other diseases and conditions.

BACKGROUND OF THE INVENTION

Diabetes is caused by multiple factors and is most simply characterized by elevated levels of plasma glucose (hyperglycemia) in the fasting state. There are two generally recognized forms of diabetes: Type 1 diabetes, or insulin-dependent diabetes mellitus (IDDM), in which patients produce little or no insulin, the hormone which regulates glucose utilization, and Type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, Type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

Persistent or uncontrolled hyperglycemia that occurs in diabetics is associated with increased morbidity and premature mortality. Abnormal glucose homeostasis is also associated both directly and indirectly with obesity, hypertension and alterations in lipid, lipoprotein and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy and retinopathy. Therefore, therapeutic control of glucose homeostasis, lipid metabolism, obesity and hypertension are critically important in the clinical management and treatment of diabetes mellitus.

Many patients who have insulin resistance but have not developed Type 2 diabetes are also at a risk of developing symptoms referred to as "Syndrome X" or "Metabolic Syndrome". Syndrome X or Metabolic Syndrome is characterized by insulin resistance, along with abdominal obesity, hyperinsulinemia, high blood pressure, low HDL and high VLDL. These patients, whether or not they develop overt diabetes mellitus, are at increased risk of developing the cardiovascular complications listed above.

Treatment of Type 2 diabetes typically includes physical exercise and dieting. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate insulin-resistant tissues. However, dangerously low levels of plasma glucose can result, and an increased level of insulin resistance can ultimately occur.

Biguanides increase insulin sensitivity, resulting in some correction of hyperglycemia. However, many biguanides, e.g., phenformin and metformin, cause lactic acidosis, nausea and diarrhea.

The glitazones (i.e. 5-benzylthiazolidine-2,4-diones) form a newer class of compounds with the potential for ameliorating hyperglycemia and other symptoms of Type 2 diabetes. These agents substantially increase insulin sensitivity in muscle, liver and adipose tissue, resulting in partial or complete correction of the elevated plasma levels of glucose substantially without causing hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes. For a review of insulin-sensitizing agents and other mechanisms for the treatment of Type 2 diabetes, see M. Tadayyon and S. A. Smith, "Insulin sensitisation in the treatment of Type 2 diabetes," *Expert Opin. Investig. Drugs*, 12: 307–324 (2003).

There is a continuing need for new methods of treating diabetes and related conditions, such as Metabolic Syndrome. The present invention meets this and other needs.

SUMMARY OF THE INVENTION

The present invention relates to bicyclo[2.2.2]-oct-1-yl-1,2,4-triazoles of structural formula I

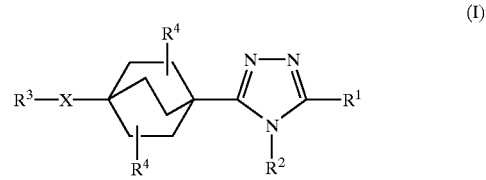

(I)

These bicyclo[2.2.2]-octyltriazole derivatives are effective as inhibitors of 11β-hydroxysteroid dehydrogenase type 1 (11β-HSD1). They are therefore useful for the treatment, control or prevention of disorders responsive to the inhibition of 11β-HSD1, such as Type 2 diabetes, lipid disorders, obesity, atherosclerosis, and Metabolic Syndrome.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of 11β-HSD1 in a subject in need thereof by administering the compounds and pharmaceutical compositions of the present invention.

The present invention also relates to methods for the treatment or control of Type 2 diabetes, obesity, lipid disorders, atherosclerosis, and Metabolic Syndrome by administering the compounds and pharmaceutical compositions of the present invention.

The present invention also relates to methods for treating obesity by administering the compounds of the present invention in combination with a therapeutically effective amount of another agent known to be useful to treat the condition.

The present invention also relates to methods for treating Type 2 diabetes by administering the compounds of the present invention in combination with a therapeutically effective amount of another agent known to be useful to treat the condition.

The present invention also relates to methods for treating atherosclerosis by administering the compounds of the present invention in combination with a therapeutically effective amount of another agent known to be useful to treat the condition.

The present invention also relates to methods for treating lipid disorders by administering the compounds of the present invention in combination with a therapeutically effective amount of another agent known to be useful to treat the condition.

The present invention also relates to methods for treating Metabolic Syndrome by administering the compounds of the present invention in combination with a therapeutically effective amount of another agent known to be useful to treat the condition.

The present invention is also concerned with the use of the compounds of structural formula I for the treatment hyperglycemia, insulin resistance, Type 2 diabetes, lipid disorders, obesity, atherosclerosis, and Metabolic Syndrome.

The present invention also provides for the use of the compounds of structural formula I in the manufacture of a medicament for use in the treatment of hyperglycemia, insulin resistance, Type 2 diabetes, lipid disorders, obesity, atherosclerosis, and Metabolic Syndrome.

DETAILED DESCRIPTION OF THE INVENTION

The present invention is concerned with bicyclo[2.2.2]-oct-1-yl-1,2,4-triazole derivatives useful as inhibitors of 11β-HSD1. Compounds of the present invention are described by structural formula I:

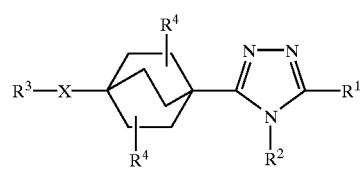

(I)

or a pharmaceutically acceptable salt thereof; wherein
each p is independently 0, 1, or 2;
each n is independently 0, 1, or 2;
X is selected from the group consisting of a single bond, O, $S(O)_p$, $NR^6$,

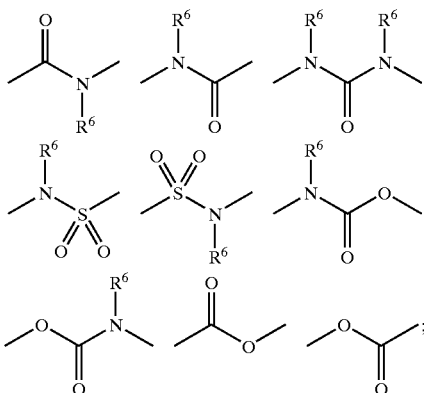

$R^1$ is selected from the group consisting of
  arylcarbonyl,
  $(CH_2)_n$-aryl, and
  $(CH_2)_n$-heteroaryl;
in which aryl and heteroaryl are unsubstituted or substituted with one to three substituents independently selected from $R^5$;
$R^2$ is selected from the group consisting of
  hydrogen,
  $C_{1-8}$ alkyl,
  $C_{2-6}$ alkenyl, and
  $(CH_2)_n$—$C_{3-6}$ cycloalkyl,
in which alkyl, alkenyl, and cycloalkyl are unsubstituted or substituted with one to three substituents independently selected from $R^8$ and oxo;
each $R^4$ is independently selected from the group consisting of
  hydrogen,
  halogen,
  hydroxy,
  oxo,
  $C_{1-3}$ alkyl, and
  $C_{1-3}$ alkoxy;
$R^3$ is selected from the group consisting of
  hydrogen,
  $C_{1-10}$ alkyl,
  $C_{2-10}$ alkenyl,
  $(CH_2)_n$—$C_{3-6}$ cycloalkyl,
  $(CH_2)_n$-aryl,
  $(CH_2)_n$-heteroaryl, and
  $(CH_2)_n$-heterocyclyl;
in which aryl, heteroaryl, and heterocyclyl are unsubstituted or substituted with one to three substituents independently selected from $R^5$; and alkyl, alkenyl, and cycloalkyl are unsubstituted or substituted with one to five groups independently selected from $R^8$ and oxo;
$R^5$ and $R^8$ are each independently selected from the group consisting of
  hydrogen,
  formyl,
  $C_{1-6}$ alkyl,
  $(CH_2)_n$-aryl,
  $(CH_2)_n$-heteroaryl,
  $(CH_2)_n$-heterocyclyl,
  $(CH_2)_n C_{3-7}$ cycloalkyl, halogen,
OR$^7$,
(CH$_2$)$_n$N(R$^7$)$_2$,
cyano,
(CH$_2$)$_n$CO$_2$R$^7$,
NO$_2$,
(CH$_2$)$_n$NR$^7$SO$_2$R$^6$,
(CH$_2$)$_n$SO$_2$N(R$^7$)$_2$,
(CH$_2$)$_n$S(O)$_p$R$^6$,
(CH$_2$)$_n$SO$_2$OR$^7$,
(CH$_2$)$_n$NR$^7$C(O)N(R$^7$)$_2$,
(CH$_2$)$_n$C(O)N(R$^7$)$_2$,
(CH$_2$)$_n$NR$^6$C(O)R$^6$,
(CH$_2$)$_n$NR$^6$CO$_2$R$^7$,
O(CH$_2$)$_n$C(O)N(R$^7$)$_2$,
CF$_3$,
CH$_2$CF$_3$,
OCF$_3$,
OCHCF$_2$, and
OCH$_2$CF$_3$;
wherein aryl, heteroaryl, cycloalkyl, and heterocyclyl are unsubstituted or substituted with one to three substituents independently selected from halogen, hydroxy, C$_{1-4}$ alkyl, trifluoromethyl, trifluoromethoxy, and C$_{1-4}$ alkoxy; and wherein any methylene (CH$_2$) carbon atom in R$^5$ and R$^8$ is unsubstituted or substituted with one to two groups independently selected from halogen, hydroxy, and C$_{1-4}$ alkyl; or two substituents when on the same methylene (CH$_2$) carbon atom are taken together with the carbon atom to which they are attached to form a cyclopropyl group;
each R$^6$ is independently selected from the group consisting of C$_{1-8}$ alkyl,
(CH$_2$)$_n$-aryl,
(CH$_2$)$_n$-heteroaryl, and
(CH$_2$)$_n$C$_{3-7}$ cycloalkyl;
wherein alkyl and cycloalkyl are unsubstituted or substituted with one to five substituents independently selected from halogen, oxo, C$_{1-4}$ alkoxy, C$_{1-4}$ alkylthio, hydroxy, amino; and aryl and heteroaryl are unsubstituted or substituted with one to three substituents independently selected from cyano, halogen, hydroxy, amino, carboxy, trifluoromethyl, trifluoromethoxy, C$_{1-4}$ alkyl, and C$_{1-4}$ alkoxy;
or two R$^6$ groups together with the atom to which they are attached form a 5- to 8-membered mono- or bicyclic ring system optionally containing an additional heteroatom selected from O, S, and NC$_{1-4}$ alkyl; and
each R$^7$ is hydrogen or R$^6$.

In one embodiment of the compounds of the present invention, R$^2$ is cyclopropyl, C$_{1-3}$ alkyl, or C$_{2-3}$ alkenyl and R$^1$ is phenyl or naphthyl in which phenyl and naphthyl are unsubstituted or substituted with one to three substituents independently selected from R$^5$. In a class of this embodiment, R$^5$ is selected from the group consisting of halogen, hydroxy, trifluoromethyl, trifluoromethoxy, C$_{1-3}$ alkyl, C$_{1-3}$ alkoxy, C$_{1-3}$ alkylthio, and C$_{1-3}$ alkylsulfonyl. In a subclass of this class, R$^2$ is methyl and R$^4$ is hydrogen.

In a second embodiment of the compounds of the present invention,
X is a single bond;
R$^1$ is phenyl or naphthyl in which phenyl and naphthyl are unsubstituted or substituted with one to three substituents independently selected from R$^5$;

R$^2$ is cyclopropyl, C$_{1-3}$ alkyl, or C$_{2-3}$ alkenyl; and
R$^3$ is C$_{1-6}$ alkyl unsubstituted or substituted with one to three substituents independently selected from R$^8$ and oxo.

In a class of this second embodiment, R$^5$ is selected from the group consisting of halogen, hydroxy, trifluoromethyl, trifluoromethoxy, C$_{1-3}$ alkyl, C$_{1-3}$ alkoxy, C$_{1-3}$ alkylthio, and C$_{1-3}$ alkylsulfonyl. In a subclass of this class, R$^2$ is methyl and R$^4$ is hydrogen. In another class of this embodiment, R$^8$ is selected from the group consisting of halogen, hydroxy, oxo, C$_{1-4}$ alkoxy, C$_{1-4}$ alkylthio, C$_{1-4}$ alkylsulfinyl, C$_{1-4}$ alkylsulfonyl, and phenyl unsubstituted or substituted with one to three groups independently selected from halogen and trifluoromethyl. In a subclass of this class, R$^2$ is methyl and R$^4$ is hydrogen. In a third class of this embodiment, R$^5$ is selected from the group consisting of halogen, hydroxy, trifluoromethyl, trifluoromethoxy, C$_{1-3}$ alkyl, C$_{1-3}$ alkoxy, C$_{1-3}$ alkylthio, and C$_{1-3}$ alkylsulfonyl; and R$^8$ is selected from the group consisting of halogen, hydroxy, oxo, C$_{1-4}$ alkoxy, C$_{1-4}$ alkylthio, C$_{1-4}$ alkylsulfonyl, and phenyl unsubstituted or substituted with one to three groups independently selected from halogen and trifluoromethyl. In a subclass of this class, R$^2$ is methyl and R$^4$ is hydrogen.

In a third embodiment of the compounds of the present invention,
X is a single bond;
R$^1$ is phenyl or naphthyl in which phenyl and naphthyl are unsubstituted or substituted with one to three substituents independently selected from R$^5$;
R$^2$ is cyclopropyl, C$_{1-3}$ alkyl, or C$_{2-3}$ alkenyl; and
R$^3$ is phenyl or heteroaryl wherein phenyl and heteroaryl are unsubstituted or substituted with one with one to three substituents independently selected from R$^5$.

In a class of this embodiment, R$^2$ is methyl and R$^4$ is hydrogen.

In another class of this embodiment, R$^3$ is phenyl unsubstituted or substituted with one with one to three substituents independently selected from R$^5$. In a subclass of this class, R$^5$ is selected from the group consisting of halogen, hydroxy, trifluoromethyl, trifluoromethoxy, C$_{1-3}$ alkyl, C$_{1-3}$ alkoxy, C$_{1-3}$ alkylthio, and C$_{1-3}$ alkylsulfonyl. In a subclass of this subclass, R$^2$ is methyl and R$^4$ is hydrogen.

In a third class of this embodiment, R$^3$ is oxadiazolyl, unsubstituted or substituted with one with one to two substituents independently selected from R$^5$.
In a subclass of this class, R$^5$ is phenyl unsubstituted or substituted with one to three substituents independently selected from halogen, hydroxy, C$_{1-4}$ alkyl, trifluoromethyl, trifluoromethoxy, and C$_{1-4}$ alkoxy. In a subclass of this subclass, R$^2$ is methyl and R$^4$ is hydrogen.

Illustrative, but nonlimiting examples, of compounds of the present invention that are useful as inhibitors of 11-beta-hydroxysteroid dehydrogenase Type I are the following:

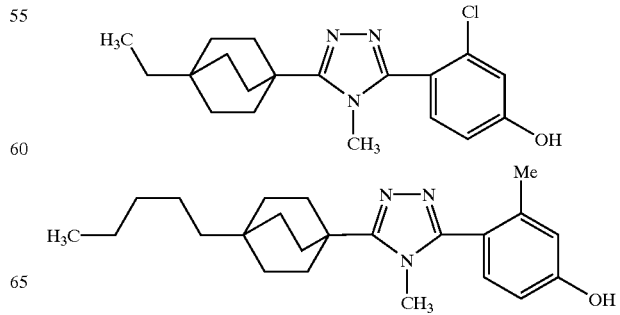

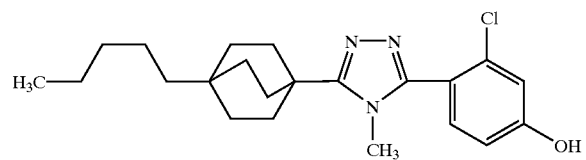
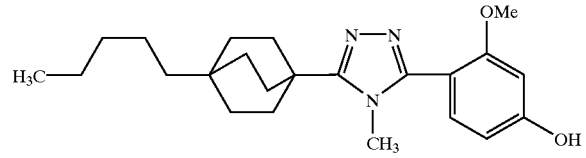
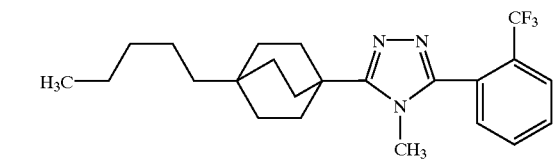
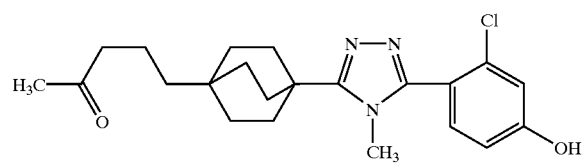
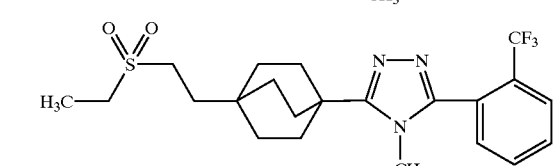
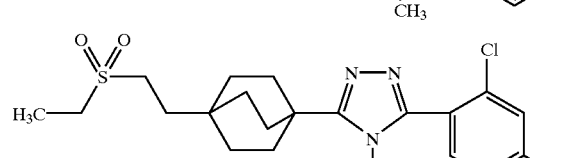
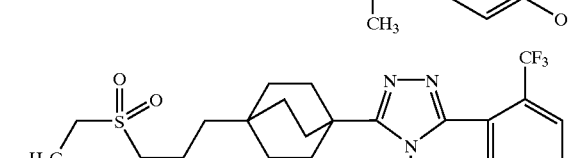
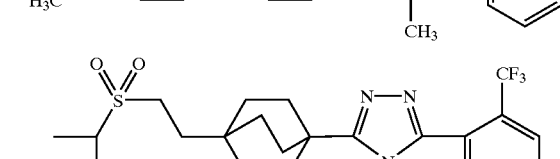
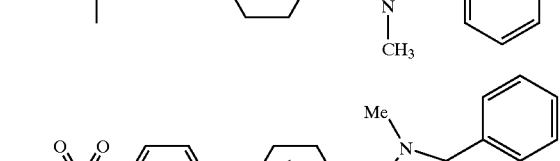
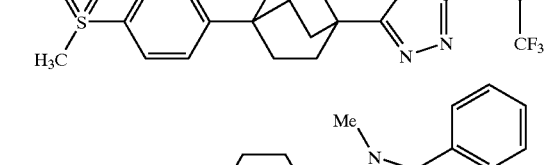
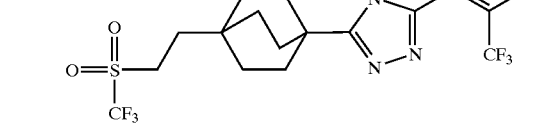

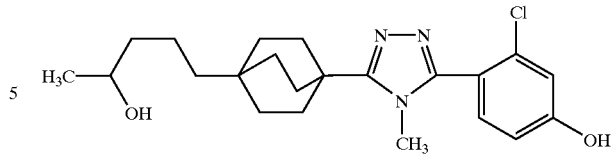
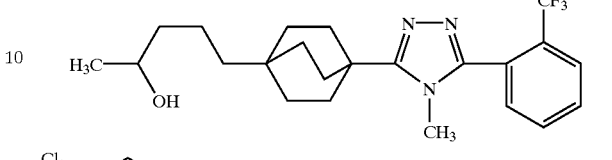
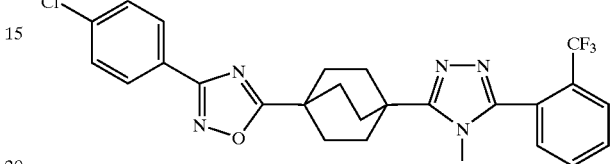
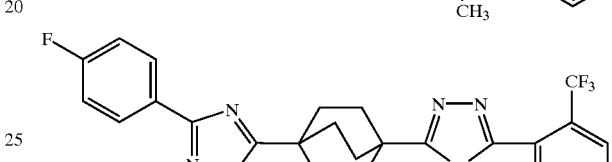
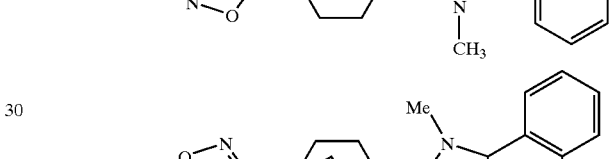
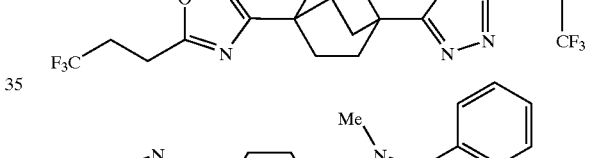
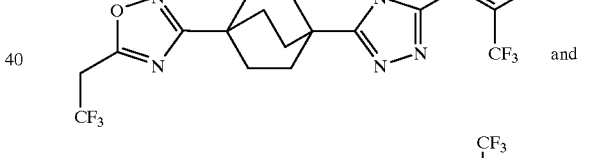
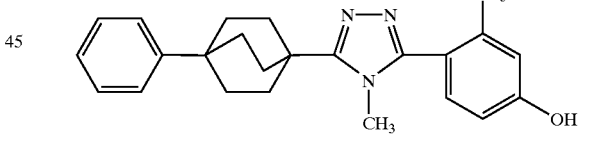
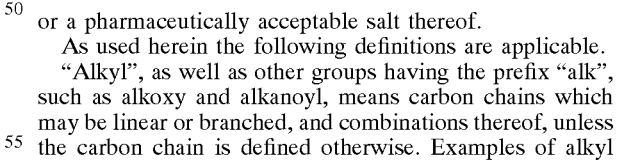
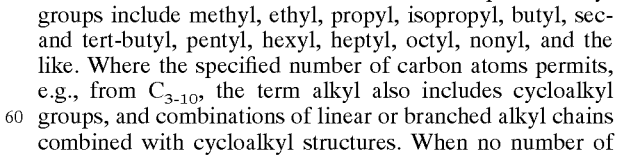 and
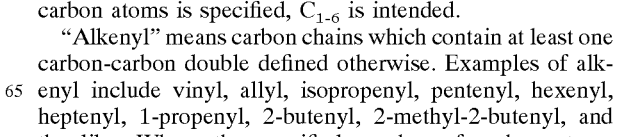

or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Alkenyl" means carbon chains which contain at least one carbon-carbon double defined otherwise. Examples of alkenyl include vinyl, allyl, isopropenyl, pentenyl, hexenyl, heptenyl, 1-propenyl, 2-butenyl, 2-methyl-2-butenyl, and the like. Where the specified number of carbon atoms permits, e.g., from $C_{5-10}$, the term alkenyl also includes cycloalkenyl groups, and combinations of linear, branched and cyclic structures. When no number of carbon atoms is specified, $C_{2-6}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl, and the like.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6–10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3–15 atoms are included, forming 1–3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto- enol tautomers. The individual tautomers, as well as mixtures thereof, are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

In a different aspect of the invention, a pharmaceutical composition is addressed comprising a compound in accordance with structural formula I, or a pharmaceutically acceptable salt or solvate thereof, in combination with a pharmaceutically acceptable carrier. By the term "solvate" is meant a hydrate, an alcoholate, or other solvate of crystallization.

In another aspect of the invention, a method of treating hyperglycemia, diabetes or insulin resistance in a mammalian patient in need of such treatment is addressed, which comprises administering to said patient an effective amount of a compound in accordance with structural formula I or a pharmaceutically salt or solvate thereof.

In another aspect of the invention, a method of treating non-insulin dependent (Type 2) diabetes mellitus in a mammalian patient in need of such treatment is disclosed comprising administering to the patient an anti-diabetic effective amount of a compound in accordance with structural formula I.

In another aspect of the invention, a method of treating obesity in a mammalian patient in need of such treatment is disclosed comprising administering to said patient a compound in accordance with structural formula I in an amount that is effective to treat obesity.

In another aspect of the invention, a method of treating Metabolic Syndrome in a mammalian patient in need of such treatment is disclosed, comprising administering to said patient a compound in accordance with structural formula I in an amount that is effective to treat Metabolic Syndrome.

In another aspect of the invention, a method of treating a lipid disorder selected from the group consisting of dyslipidemia, hyperlipidemia, hypertriglyceridemia, hypercholesterolemia, low HDL, and high LDL in a mammalian patient in need of such treatment is disclosed, comprising administering to said patient a compound in accordance with structural formula I in an amount that is effective to treat said lipid disorder.

In another aspect of the invention, a method of treating atherosclerosis in a mammalian patient in need of such treatment is disclosed, comprising administering to said patient a compound in accordance with structural formula I in an amount effective to treat atherosclerosis.

In another aspect of the invention, a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component, in a mammalian patient in need of such treatment is disclosed, comprising administering to the patient a compound in accordance with structural formula I in an amount that is effective to treat said condition.

In another aspect of the invention, a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to delay the onset of said condition.

In another aspect of the invention, a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to reduce the risk of developing said condition.

In another aspect of the invention, a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component, in a mammalian patient in need of such treatment, comprising administering to the patient an effective amount of a compound as defined in structural formula I and a compound selected from the group consisting of:

(a) dipeptidyl peptidase-IV (DP-IV) inhibitors;

(b) insulin sensitizing agents selected from the group consisting of (i) PPARγ agonists, (ii) PPARα agonists, (iii) PPARα/γ dual agonists, and (iv) biguanides;

(c) insulin and insulin mimetics;

(d) sulfonylureas and other insulin secretagogues;

(e) α-glucosidase inhibitors;

(f) glucagon receptor antagonists;

(g) GLP-1, GLP-1 analogs, and GLP-1 receptor agonists;

(h) GIP,GIP mimetics, and GIP receptor agonists;

(i) PACAP, PACAP mimetics, and PACAP receptor 3 agonists;

(j) cholesterol lowering agents selected from the group consisting of (i) HMG-CoA reductase inhibitors, (ii) sequestrants, (iii) nicotinyl alcohol, nicotinic acid and salts thereof, (iv) inhibitors of cholesterol absorption, (v) acyl CoA:cholesterol acyltransferase inhibitors, and (vi) anti-oxidants;

(k) PPARδ agonists;

(l) antiobesity compounds;

(m) ileal bile acid transporter inhibitors;

(n) anti-inflammatory agents, excluding glucocorticoids;

(o) protein tyrosine phosphatase 1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan;

said compounds being administered to the patient in an amount that is effective to treat said condition.

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutamine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677–1692 (2001)

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists, *Expert Opin. Ther. Patents*, 12: 1631–1638 (2002).

In another aspect of the invention, a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment is disclosed, comprising administering to the patient a therapeutically effective amount of a compound as defined in structural formula I and an HMG-CoA reductase inhibitor.

More particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, cerivastatin, fluvastatin, atorvastatin, itavastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound as defined in structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound as defined in structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of developing atherosclerosis in a human patient in need of such treatment is disclosed, wherein the HMG-Co A reductase inhibitor is a statin selected from the group consisting of: lovastatin, simvastatin, pravastatin, cerivastatin, fluvastatin, atorvastatin, itavastatin, and rosuvastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-CoA reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises
(1) a compound according to structural formula I,
(2) a compound selected from the group consisting of:
  (a) DP-IV inhibitors;
  (b) insulin sensitizing agents selected from the group consisting of (i) PPARγ agonists; (ii) PPARα agonists, (iii) PPARα/γ dual agonists, and (iv) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 analogs, and GLP-1 receptor agonists;
  (h) GIP, GIP mimetics, and GIP receptor agonists;
  (i) PACAP, PACAP mimetics, and PACAP receptor 3 agonists;
  (j) cholesterol lowering agents selected from the group consisting of (i) HMG-CoA reductase inhibitors, (ii) sequestrants, (iii) nicotinyl alcohol, nicotinic acid or a salt thereof, (iv) inhibitors of cholesterol absorption, (v) acyl CoA:cholesterol acyltransferase inhibitors, and (vi) anti-oxidants;

(k) PPARδ agonists;

(l) antiobesity compounds;

(m) ileal bile acid transporter inhibitors;

(n) anti-inflammatory agents other than glucocorticoids;

(o) protein tyrosine phosphatase 1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and (3) a pharmaceutically acceptable carrier.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylarmine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of structural formula I are included in the present invention as well.

The compounds described herein are selective inhibitors of the 11β-HSD1 enzyme. Thus, the present invention relates to the use of the 11β-HSD1 inhibitors for inhibiting the reductase activity of 11β-hydroxysteroid dehydrogenase, which is responsible for the conversion of cortisone to cortisol. Excess cortisol is associated with numerous disorders, including NIDDM, obesity, dyslipidemia, insulin resistance and hypertension. Administration of the compounds of the present invention decreases the level of cortisol and other 11β-hydroxysteroids in target tissues, thereby reducing the effects of excessive amounts of cortisol and other 11β-hydroxysteroids. Inhibition of 11β-HSD1 can be used to treat and control diseases mediated by abnormally high levels of cortisol and other 11β-hydroxysteroids, such as NIDDM, obesity, hypertension and dyslipidemia. Inhibition of 11β-HSD1 activity in the brain such as to lower cortisol levels may also be useful to treat or reduce anxiety, depression, and cognitive impairment.

The present invention includes the use of an 11β-HSD1 inhibitor for the treatment, control, amelioration, prevention, delaying the onset of or reducing the risk of developing the diseases and conditions that are described herein, as mediated by excess or uncontrolled amounts of cortisol and/or other corticosteroids in a mammalian patient, particularly a human, by the administration of an effective amount of a compound of structural formula I or a pharmaceutically acceptable salt or solvate thereof. Inhibition of the 11β-HSD1 enzyme limits the conversion of cortisone, which is normally inert, to cortisol, which can cause or contribute to the symptoms of these diseases and conditions if present in excessive amounts.

NIDDM and Hypertension:

The compounds of this invention are selective inhibitors of 11β-HSD1 over 11β-HSD2. While the inhibition of 11β-HSD1 is useful for reducing cortisol levels and treating conditions related thereto, inhibition of 11β-HSD2 is associated with serious side effects, such as hypertension.

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing Type 2 diabetes in the presence of abnormally high levels of cortisol.

High levels of cortisol in tissues where the mineralocorticoid receptor is present often lead to hypertension. Inhibition of 11β-HSD1 shifts the ratio of cortisol and cortisone in specific tissues in favor of cortisone.

Administration of a therapeutically effective amount of an 11β-HSD1 inhibitor is effective in treating, controlling and ameliorating the symptoms of NIDDM, and administration of a therapeutically effective amount of an 11β-HSD1 inhibitor on a regular basis delays or prevents the onset of NIDDM, particularly in humans.

Cushing's Syndrome:

The effect of elevated levels of cortisol is also observed in patients who have Cushing's Syndrome, which is a metabolic disease characterized by high levels of cortisol in the blood stream. Patients with Cushing's Syndrome often develop NIDDM.

Obesity, Metabolic Syndrome, Dyslipidemia:

Excessive levels of cortisol have been associated with obesity, perhaps due to increased hepatic gluconeogenesis. Abdominal obesity is closely associated with glucose intolerance, hyperinsulinemia, hypertriglyceridemia, and other factors of Metabolic Syndrome, such as high blood pressure, elevated VLDL and reduced HDL. Montague et al., *Diabetes*, 2000, 49: 883–888. Thus, the administration of an effective amount of an 11β-HSD1 inhibitor is useful in the treatment or control of obesity. Long-term treatment with an 11β-HSD1 inhibitor is also useful in delaying or preventing the onset of obesity, especially if the patient uses an 11β-HSD1 inhibitor in combination with controlled diet and exercise.

By reducing insulin resistance and maintaining serum glucose at normal concentrations, compounds of the present invention also have utility in the treatment and prevention of conditions that accompany Type II diabetes and insulin resistance, including the Metabolic Syndrome or Syndrome X, obesity, reactive hypoglycemia and diabetic dyslipidemia.

Cognition and Dementia:

Excessive levels of cortisol in the brain may also result in neuronal loss or dysfunction through the potentiation of neurotoxins. Cognitive impairment has been associated with aging, and excess levels of cortisol in the brain. See J. R. Secki and B. R. Walker, *Endocrinology*, 2001, 142: 1371–1376, and references cited therein. Administration of an effective amount of an 11β-HSD1 inhibitor results in the reduction, amelioration, control or prevention of cognitive impairment associated with aging and of neuronal dysfunction. Inhibitors of 11β-HSD1 may also be useful to treat anxiety and depression.

Atherosclerosis:

As described above, inhibition of 11β-HSD 1 activity and a reduction in the amount of cortisol are beneficial in treating or controlling hypertension. Since hypertension and dyslipidemia contribute to the development of atherosclerosis, administration of a therapeutically effective amount of an 11β-HSD1 inhibitor of the present invention may be especially beneficial in treating, controlling, delaying the onset of or preventing atherosclerosis.

Effects on Pancreas:

Inhibition of 11β-HSD1 activity in isolated murine pancreatic β-cells improves glucose stimulated insulin secretion (B. Davani et al., *J. Biol. Chem.*, 2000, 275: 34841–34844). Glucocorticoids have been shown to reduce insulin secretion in vivo. (B. Billaudel et al., *Horm. Metab. Res.*, 1979, 11: 555–560).

Reduction of Intraocular Pressure:

Recent data suggests a connection between the levels of glucocorticoid target receptors and the 11β-HSD enzymes and the susceptibility to glaucoma (J. Stokes et al., *Invest. Ophthamol.*, 2000, 41: 1629–1638). Therefore, inhibition of 11β-HSD1 activity is useful in reducing intraocular pressure in the treatment of glaucoma.

Immunomodulation:

In certain disease states, such as tuberculosis, psoriasis, and even under conditions of excessive stress, high glucocorticoid activity shifts the immune response to a humoral response, when in fact a cell based response may be more beneficial to the patient. Inhibition of 11β-HSD1 activity and the attendant reduction in glucocorticoid levels shifts the immune response toward a cell based response. See D. Mason, *Immunology Today*, 1991, 12: 57–60, and G. A. W. Rook, *Baillièr's Clin. Endocrinol. Metab.*, 1999, 13: 576–581.

Osteoporosis:

Glucocorticoids can inhibit bone formation, which can result in a net bone loss. 11β-HSD1 has a role in bone resorption. Inhibition of 11β-HSD1 is beneficial in preventing bone loss due to osteoporosis. See C. H. Kim et al., *J. Endocrinol.*, 1999, 162: 371–379; C. G. Bellows et al., *Bone*, 1998, 23: 119–125; and M. S. Cooper et al., *Bone*, 2000,27: 375–381.

Other Utilities:

The following diseases, disorders and conditions can be treated, controlled, prevented or delayed, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other disorders where insulin resistance is a component.

The above diseases and conditions can be treated using the compounds of structural formula I, or the compound can be administered to prevent or reduce the risk of developintg the diseases and conditions described herein. Since concurrent inhibition of 11β-HSD2 may have deleterious side effects or may actually increase the amount of cortisol in the target tissue where reduction of cortisol is desired, selective inhibitors of 11β-HSD1 with little or no inhibition of 11β-HSD2 are desirable.

The 11β-HSD1 inhibitors of structural formula I generally have an inhibition constant $IC_{50}$ of less than about 500 nM, and preferably less than about 100 nM. Generally, the $IC_{50}$ ratio for 11β-HSD2 to 11β-HSD1 of a compound is at least about two or more, and preferably about ten or greater. Even more preferred are compounds with an $IC_{50}$ ratio for 11β-HSD2 to 11β-HSD1 of about 100 or greater. For example, compounds of the present invention ideally demonstrate an inhibition constant $IC_{50}$ against 11β-HSD2 greater than about 1000 nM, and preferably greater than 5000 nM.

Compounds of structural formula I may be used in combination with one or more other drugs in the treatment, prevention, suppression or amelioration of diseases or conditions for which compounds of structural formula I or the other drugs have utility. Typically the combination of the drugs is safer or more effective than either drug alone, or the combination is safer or more effective than would be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to:

(a) dipeptidyl peptidase IV (DP-IV) inhibitors;
(b) insulin sensitizing agents including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin;
(c) insulin or insulin mimetics;
(d) sulfonylureas and other insulin secretagogues such as tolbutamide, glipizide, meglitinide and related materials;
(e) α-glucosidase inhibitors, such as acarbose;
(f) glucagon receptor antagonists such as those disclosed in WO 98/04528, WO 99/01423, WO 00/39088 and WO 00/69810;
(g) GLP-1, GLP-1 analogs, and GLP-1 receptor agonists such as those disclosed in WO00/42026 and WO00/59887;
(h) GIP, GIP mimetics such as those disclosed in WO00/58360, and GIP receptor agonists;
(i) PACAP, PACAP mimetics, and PACAP receptor 3 agonists such as those disclosed in WO 01/23420;
(j) cholesterol lowering agents such as (i) HMG-CoA reductase inhibitors (lovastatin, simvastatin, pravastatin, cerivastatin, fluvastatin, atorvastatin, itavastatin, rosuvastatin, and other statins), (ii) bile-acid sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as ezetimibe and beta-sitosterol, (v) acyl CoA:cholesterol acyltransferase inhibitors, such as, for example, avasimibe, and (vi) anti-oxidants, such as probucol;
(k) PPARδ agonists, such as those disclosed in WO97/28149;
(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin- receptor agonists, in particular melanocortin-4 receptor agonists, ghrelin antagonists, and melanin-concentrating hormone (MCH) receptor antagonists;
(m) ileal bile acid transporter inhibitors;
(n) agents intended for use in inflammatory conditions other than glucocorticoids, such as aspirin, non-steroidal anti-inflammatory drugs, azulfidine, and selective cyclooxygenase-2 inhibitors;
(o) protein tyrosine phosphatase 1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan.

The above combinations include a compound of structural formula I, or a pharmaceutically acceptable salt or solvate thereof, with one or more other active compounds. Non-limiting examples include combinations of compounds of structural formula I with two or more active compounds selected from biguanides, sulfonylureas, HMG-CoA reductase inhibitors, PPAR agonists, PTP-1B inhibitors, DP-IV inhibitors, and anti-obesity compounds.

Any suitable route of administration may be employed for providing a mammal, especially a human, with an effective dose of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols and the like. Preferably the compound of structural formula I is administered orally.

The effective dosage of the active ingredient varies depending on the particular compound employed, the mode of administration, the condition being treated and the severity of the condition. Such dosages may be ascertained readily by a person skilled in the art.

When treating or preventing the diseases and conditions described herein, for which compounds of structural formula I are indicated, satisfactory results are obtained when the compounds of the invention are administered at a daily dosage of from about 0.1 to about 100 milligram per kilogram (mpk) of body weight, preferably given as a single daily dose or in divided doses about two to six times a day. The total daily dosage thus ranges from about 0.1 mg to about 1000 mg, preferably from about 1 mg to about 50 mg. In the case of a typical 70 kg adult human, the total daily dose will range from about 7 mg to about 350 mg. This dosage may be adjusted to provide the optimal therapeutic response.

Another aspect of the present invention relates to a pharmaceutical composition which comprises a compound of structural formula I, or a pharmaceutically acceptable salt or solvate thereof, in combination with a pharmaceutically acceptable carrier.

The compositions include compositions suitable for oral, rectal, topical, parenteral (including subcutaneous, intramuscular, and intravenous), ocular (ophthalmic), transdermal, pulmonary (nasal or buccal inhalation), or nasal administration, although the most suitable route in any given case will depend on the nature and severity of the condition being treated and the active ingredient. They may be conveniently presented in unit dosage form and prepared by any of the methods well-known in the art of pharmacy.

The compound of structural formula I can be combined with the pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are preferred over oral liquids.

The oral solid dosage forms may also contain a binder such as gum tragacanth, acacia, corn starch or gelatin;

excipients such as dicalcium phosphate; a disintegrating agent such as corn starch, potato starch, alginic acid; a lubricant such as magnesium stearate; and a sweetening agent such as sucrose, lactose or saccharin. Capsules may also contain a liquid carrier such as a fatty oil.

Various other materials may be present to act as coatings or to modify the physical form of the dosage unit. For instance, tablets may be coated with shellac, sugar or both.

Tablets may be coated by standard aqueous or nonaqueous techniques. The typical percentage of active compound in these compositions may, of course, be varied from about 2 percent to about 60 percent on a w/w basis. Thus, tablets contain a compound of structural formula I or a salt or hydrate thereof in an amount ranging from as low as about 0.1 mg to as high as about 1.5 g, preferably from as low as about 1.0 mg to as high as about 500 mg, and more preferably from as low as about 10 mg to as high as about 100 mg.

Oral liquids such as syrups or elixirs may contain, in addition to the active ingredient, sucrose as a sweetening agent, methyl and propylparabens as preservatives, a dye and a favoring such as cherry or orange flavor.

Parenterals are typically in the form of a solution or suspension, typically prepared with water, and optionally including a surfactant such as hydroxypropylcellulose. Dispersions can be prepared in glycerol, liquid polyethylene glycols and mixtures thereof in oils. Typically preparations that are in diluted form also contain a preservative.

The pharmaceutical injectable dosage forms, including aqueous solutions and dispersions and powders for the extemporaneous preparation of injectable solutions or dispersions, are also sterile and must be fluid to the extent that easy syringability exists; they must be stable under the conditions of manufacture and storage and are usually preserved. The carrier thus includes the solvent or dispersion medium containing, for example, water, ethanol, polyol (e.g. glycerol, propylene glycol and liquid polyethylene glycol), suitable mixtures thereof, and vegetable oils.

Assays: Measurement of Inhibition Constants

In vitro enzymatic activity was assessed for test compounds via a Scintillation Proximity Assay (SPA). In short, tritiated-cortisone substrate, NADPH cofactor and titrated compound of structural formula I were incubated with 11β-HSD1 enzyme at 37° C. to allow conversion to cortisol to progress. Following this incubation, a preparation of protein A coated SPA beads, pre-blended with anti-cortisol monoclonal antibody and a non-specific 11β-HSD inhibitor, such as 18β-glycyrrhetinic acid, was added to each well. The mixture was shaken at 15° C. and was then read on a liquid scintillation counter suitable for 96 well plates. Percent inhibition was calculated relative to a non-inhibited control well and $IC_{50}$ curves were generated. This assay was similarly applied to 11β-HSD2, whereby tritiated cortisol and NAD were used as the substrate and cofactor, respectively. To begin the assay, 40 μL of substrate (25 nM $^3$H-Cortisone+ 1.25 mM NADPH in 50 mM HEPES Buffer, pH 7.4) was added to designated wells on a 96-well plate. The compound was dissolved in DMSO at 10 mM followed by a subsequent 50 fold dilution in DMSO. The diluted material was then titrated 4 fold, seven times. 1 μL of each titrated compound was then added in duplicate to the substrate. To start the reaction, 10 μL of 11β-HSD1 microsome from CHO transfectants was added to each well at the appropriate concentration to yield approximately 10% conversion of the starting material. For ultimate calculation of percent inhibition, a series of wells were added that represented the assay minimum and maximum: one set that contained substrate without compound or enzyme (background), and another set that contained substrate and enzyme without any compound (maximum signal). The plates were spun briefly at a low speed in a centrifuge to pool the reagents, sealed with an adhesive strip, mixed gently, and incubated at 37° C. for 2 h. After incubation, 45 μL of SPA beads, pre-suspended with anti-cortisol monoclonal antibody and a compound of formula I, were added to each well. The plates were resealed and shaken gently for greater than 1.5 h at 15° C. Data were collected on a plate based liquid scintillation counter such as a Topcount. To control for inhibition of anti-cortisol antibody/cortisol binding, substrate spiked with 1.25 nM $^3$H cortisol was added to designated single wells. 1 μL of 200 μM compound was added to each of these wells, along with 10 μL of buffer instead of enzyme. Any calculated inhibiton was due to compound interfering with the cortisol binding to the antibody on the SPA beads.

Assays: Measurement of In vivo Inhibition

In general terms, the test compound was dosed orally to a mammal and a prescribed time interval was allowed to elapse, usually between 1 and 24 h. Tritiated cortisone was injected intravenously, followed several min later by blood collection. Steroids were extracted from the separated serum and analyzed by HPLC. The relative levels of $^3$H-cortisone and its reduction product, $^3$H-cortisol, were determined for the compound and vehicle-dosed control groups. The absolute conversion, as well as the percentage of inhibition, was calculated from these values.

More specifically, compounds were prepared for oral dosing by dissolving them in vehicle (5% hydroxypropyl-beta-cyclodextrin v/v $H_2O$, or equivalent) at the desired concentration to allow dosing at typically 10 mg per kg. Following an overnight fasting, the solutions were dosed to ICR mice (obtained from Charles River) by oral gavage, 0.5 mL per dose per animal, with three animals per test group.

After the desired time had passed, routinely either 4 or 16 h, 0.2 mL of 3 μM $^3$H-cortisone in DPBS was injected by tail vein. The animal was caged for two min followed by euthanasia in a $CO_2$ chamber. Upon expiration, the mouse was removed and blood was collected by cardiac puncture. The blood was set aside in a serum separation tube for no less than 30 min at room temperature to allow for adequate coagulation. After the incubation period, blood was separated into serum by centrifugation at 3000×g, 4° C., for 10 min.

To analyze the steroids in the serum, they were first extracted with organic solvent. A 0.2 mL volume of serum was transferred to a clean microcentrifuge tube. To this a 1.0 mL volume of ethyl acetate was added, followed by vigorous vortexing for 1 min. A quick spin on a microcentrifuge pelleted the aqueous serum proteins and clarified the organic supernatant. 0.85 mL of the upper organic phase was transferred to a fresh microcentrifuge tube and dried. The dried sample was resuspended in 0.250 mL of DMSO containing a high concentration of cortisone and cortisol for analysis by HPLC.

A 0.200 mL sample was injected onto a Metachem Inertsil C-18 chromatography column equilibrated in 30% methanol. A slow linear gradient to 50% methanol separated the target steroids; simultaneous monitoring by UV at 254 nm of the cold standards in the resuspension solution acted as an internal standard. The tritium signal was collected by a radiochromatography detector that uploaded data to software for analysis. The percent conversion of $^3$H-cortisone to ³H-cortisol was calculated as the ratio of AUC for cortisol over the combined AUC for cortisone and cortisol.

Preparation of Compounds of the Invention:

The compounds of structural formula I of the present invention can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the their neutral form, but the triazole moeity can be further converted into a pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electrospray ion-mass spectroscopy (ESMS).

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. Cbz and BOC are commonly used protecting groups in organic synthesis, and their removal conditions are known to those skilled in the art.

Abbreviations Used in the Description of the Preparation of the Compounds of the Present Invention:

| AIBN | 2,2'-azobisisobutyronitrile |
|---|---|
| BOC | t-butyloxycarbonyl |
| BBr₃ | boron tribromide |
| 9-BBN | 9-borabicyclo[3.3.1]nonane |
| Bn | benzyl |
| nBuLi | n-butyl lithium |
| Cbz | benzyloxycarbonyl |
| CDI | 1,1'-carbonyldiimidazole |
| MeOTf | methyl trifluoromethanesulfonate |
| CH₂Cl₂ | dichloromethane |
| CH₂I₂ | diiodomethane |
| (COCl)₂ | oxalyl chloride |
| Cs₂CO₃ | cesium carbonate |
| DAST | (diethylamino)sulfur trifluoride |
| DMAP | 4-(dimethylamino)pyridine |
| DMF | N,N-dimethylformamide |
| Et | ethyl |
| Et₃N | triethylamine |
| EtOAc | ethyl acetate |
| Et₂Zn | diethylzinc |
| H₂O₂ | hydrogen peroxide |
| Me | methyl |
| MeCN | acetonitrile |
| MeOH | methanol |
| mCPBA | meta-chloroperbenzoic acid |
| MS | mass spectrum |
| NaBH₄ | sodium borohydride |
| NaHCO₃ | sodium hydrogencarbonate |
| NaOAc | sodium acetate |
| NBS | N-bromosuccinimide |
| Ph | phenyl |
| PyBROP | bromotripyrrolidinophosphonium hexafluorophosphate |
| PPh₃ | triphenylphosphine |
| pyr | pyridine |
| SOCl₂ | thionyl chloride |
| TFA | trifluoroacetic acid |
| TFFH | N,N,N',N'-tetramethylformamidinium hexafluorophosphate |
| THF | tetrahydrofuran |
| TLC | thin-layer chromatography |
| TsOH | p-toluenesulfonic acid |

Reaction Schemes 1–5 illustrate the methods employed in the synthesis of the compounds of the present invention of structural formula I. All substituents are as defined above unless indicated otherwise.

Reaction Scheme 1 illustrates a key step in the synthesis of the novel compounds of structural formula I of the present invention. As shown in reaction Scheme 1, a secondary amide (1-1) (N-Me or N-Et preferred) can be methylated by heating with neat methyl triflate in order to provide an iminoether (1-2). Alternatively other methylating reagents such as methyl iodide or methyl sulfate may be used neat or in a non-nucleophilic organic solvent. As shown in Scheme 1, a bicyclo[2.2.2]octane-1-carboxylic acid (1-3) is converted to an acyl hydrazide (1-4) by using the coupling reagent TFFH and hydrazine in the presence of a tertiary amine base such as triethylamine. Alternatively, other coupling reagents commonly used for preparing amides may be used for this tranformation along with hydrazine. Alternatively, a bicyclo[2.2.2]octane-1-carboxylic ester can be heated with hydrazine to prepare acyl hydrazides (1-4). The acyl hydrazide (1-4) and iminoether (1-2) thus produced can be heated together in an inert high boiling organic solvent such as toluene in the presence of a tertiary amine base such as triethylamine to provide bicyclo[2.2.2]octyltriazoles (1-5) of structural formula I.

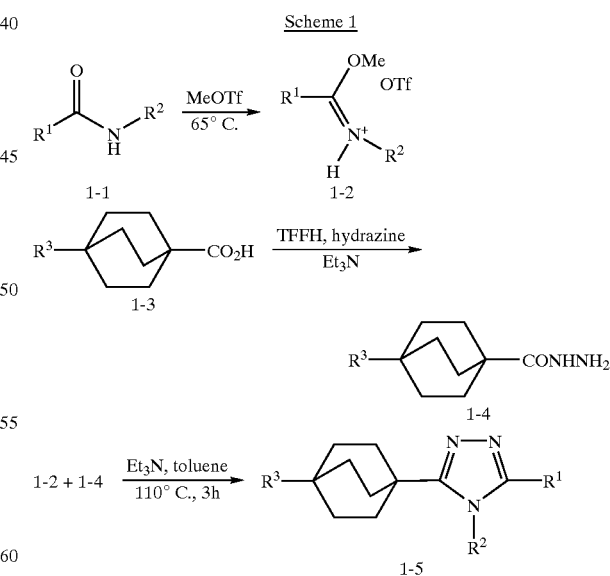

Scheme 1

Alternatively, the reaction can be conducted in the inverse manner as described by reaction Scheme 2. In this procedure a secondary amide (2-1) is prepared from a bicyclo[2.2.2]octane-1-carboxylic acid using a standard peptide coupling reaction. This compound is methylated to form the iminoether (2-2) and reacted with an acyl hydrazide as described for reaction Scheme 1 to provide bicyclo[2.2.2]octyltriazoles (2-3) of structural formula I.

Scheme 2

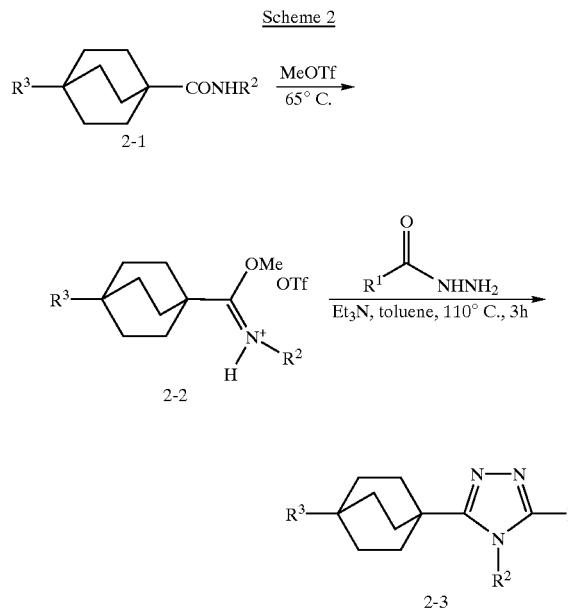

Reaction Scheme 3 describes an alternate approach to compounds of the present invention of structural formula I, in which the key step is the palladium catalyzed Suzuki coupling reaction between a bicyclo[2.2.2]octylbromotriazole (3-1) and an aryl boronic acid to produce triazoles (3-2) of structural formula I. The preferred conditions use tetrakis(triphenylphosphine)palladium(0) as the catalyst in DMF solvent with cesium carbonate, but other catalysts and conditions may be employed, as recognized by those skilled in the art.

Scheme 3

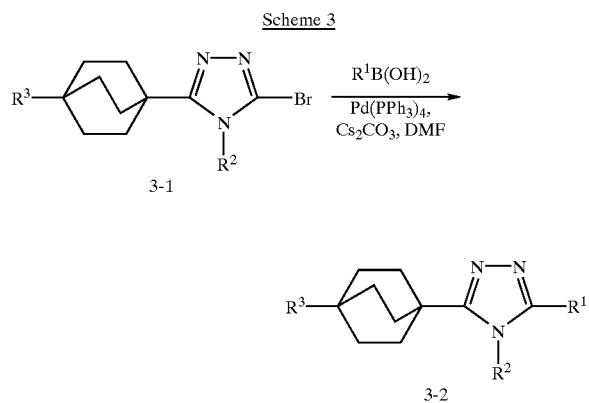

Reaction Scheme 4 describes yet another synthetic approach to the formation of compounds of structural formula I. Using this procedure, 4-(bicyclo[2.2.2]octyl)oxadiazoles (4-1) are dehydratively condensed with methylamine, either neat in a melt with methylammonium trifluoroacetate or in buffered MeOH solution. These reactions are best performed at high temperatures in a high pressure reactor to prevent the loss of methylamine.

Scheme 4

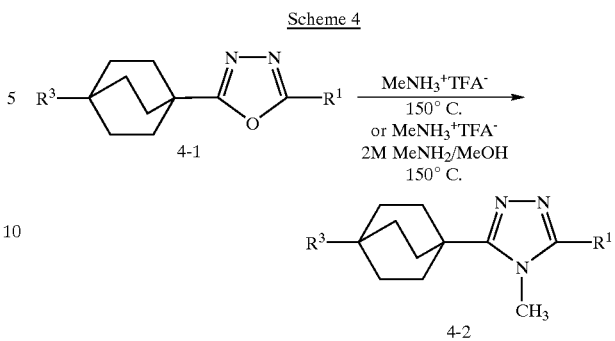

Reaction Scheme 5 describes yet another synthetic approach to the formation of compounds of structural formula I. Using this procedure, bicyclo[2.2.2]octylcarboxamides (5-1) are converted to iminochlorides (5-2), using a reagent such as oxalyl chloride, thionyl chloride, phosphorus oxychloride or phosphorus pentachloride, optionally in the presence of DMF. The iminochloride (5-2) is condensed with an aryl tetrazole in a high boiling inert organic solvent such as toluene to provide the triazole (5-3).

Scheme 5

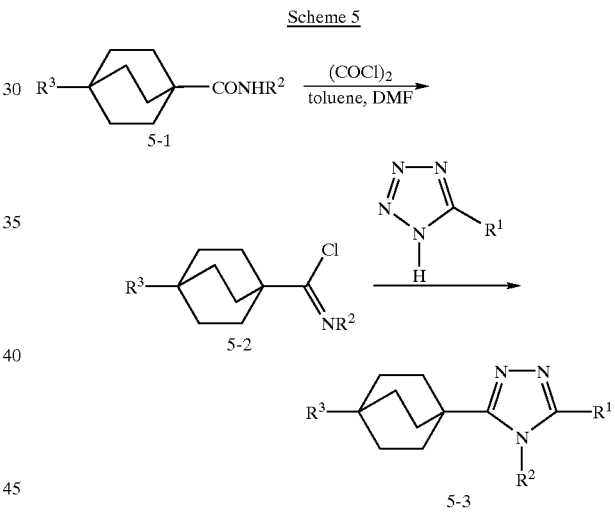

Preparation of [2.2.2]Bicyclooctyl Intermediates:

The procedures used in the preparation of [2.2.2]bicyclooctyl intermediates for use in the preparation of compounds of the present invention are provided below.

Intermediate Schemes 1–4 describe the preparation of oxadiazoles, which are important intermediates for the synthesis of compounds of structural formula I. They can be converted into compounds of structural formula I using, for example, the reactions described in reaction Scheme 4.

Intermediate Scheme I shows a preferred method for the preparation of oxadiazoles via the dehydration of diacyl hydrazides using a dehydrating reagent such as thionyl chloride. Alternatively, other dehydrating reagents such as phosphorus oxychloride, phosphorus pentachloride or oxalyl chloride may be employed. The diacyl hydrazides may be prepared preferentially from a hydrazide and an activated acid, such as an acid chloride, in the presence of a tertiary amine base. Alternatively, standard peptide coupling reactions may be employed to prepare the diacyl hydrazide from a hydrazide and a carboxylic acid.

Intermediate Scheme 2 shows a useful reagent for the dehydration of diacyl hydrazides to oxadiazoles, namely, 2-chloro-1,3-dimethyl-4,5-dihydro-1H-imidazol-3-ium chloride. This reagent in a non-polar solvent (methylene chloride is preferred) along with a tertiary amine base (triethylamine is preferred) gives the desired oxadiazole intermediates in an efficient manner.

Intermediate Scheme 3 shows a preferred reagent for the one pot formation (from a hydrazide and a carboxylic acid) and dehydration of diacyl hydrazides to oxadiazoles: 2-chloro-1,3-dimethyl-4,5-dihydro-1H-imidazol-3-ium chloride. This reagent in a non-polar solvent (methylene chloride is preferred) along with a tertiary amine base (triethylamine is preferred) gives the desired oxadiazole intermediates in an efficient manner.

Intermediate Scheme 4 shows an efficient method for the formation of oxadiazoles from secondary amides and hydrazides. The secondary amide (N—Me or N-Et preferred) can be methylated by heating with neat methyl triflate in order to provide an iminoether. Alternatively other methylating reagents such as methyl iodide or methyl sulfate may be used neat or in a non-nucleophilic organic solvent. Heating the iminoether thus formed in a high boiling inert organic solvent in the presence of a hydrazide affords oxadiazoles as shown in the Scheme.

INTERMEDIATE SCHEME 3:

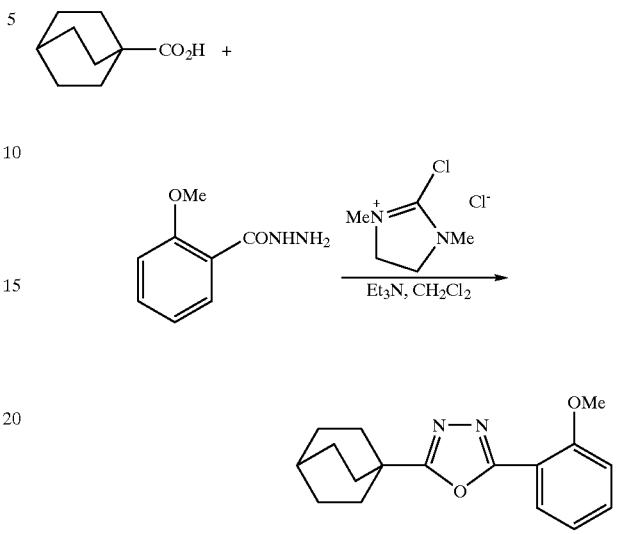

INTERMEDIATE SCHEME 1:

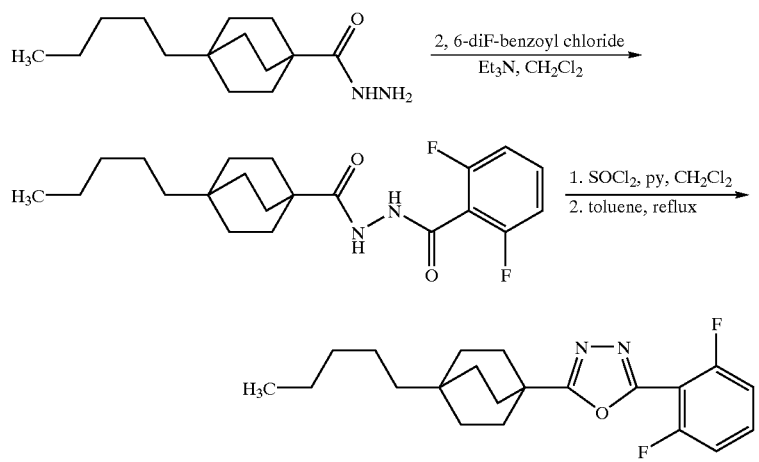

INTERMEDIATE SCHEME 2:

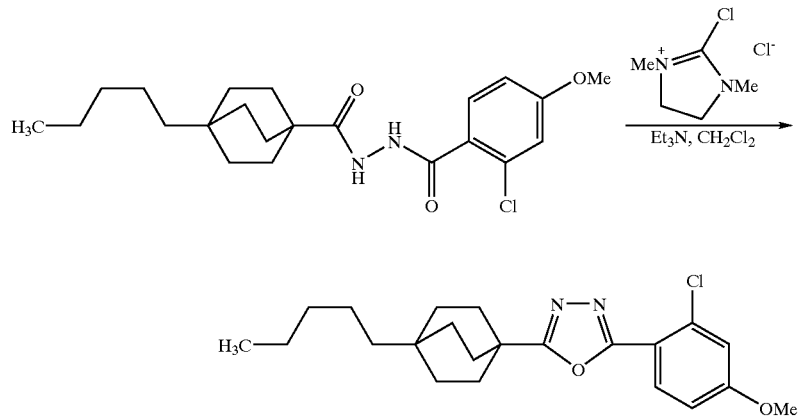

INTERMEDIATE SCHEME 4:

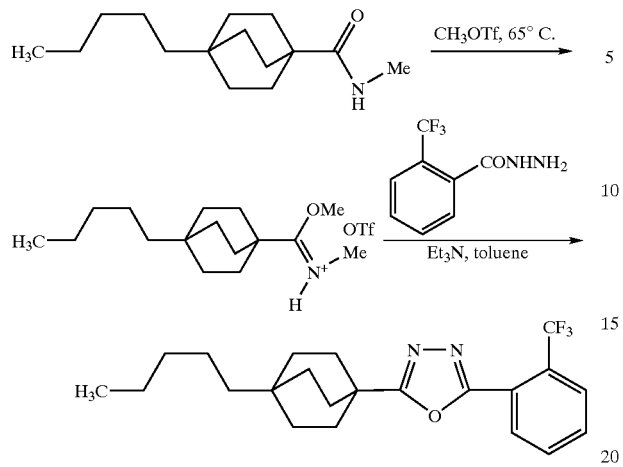

Intermediate Scheme 5 shows a preferred method for the synthesis of bicyclo[2.2.2]octane-1-carboxylic acid.

INTERMEDIATE SCHEME 5:

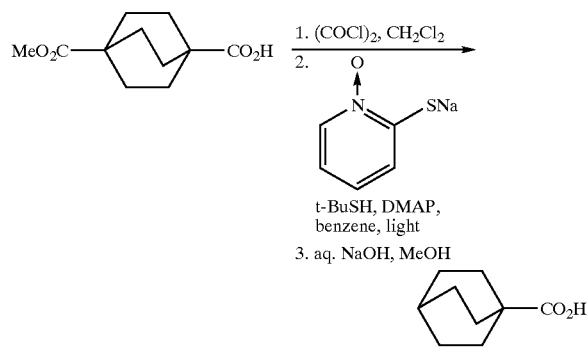

Intermediate Schemes 6 and 7 show preferred methods for the preparation of bicyclo[2.2.2]octane-1-carboxylic acids with a heteroaryl group at the $R^3$ position as given by structural formula I. Oxadiazoles at the $R^3$ position may be prepared by the condensation of a bicyclo[2.2.2]octyl-1-carboxylic acid with an amidoxime as shown in Intermediate Scheme 6. A useful reagent for this coupling is CDI. Alternatively, other reagents useful for dehydration or peptide coupling reactions may be employed. Intermediate Scheme 7 illustrates a preferred method for the synthesis of an intermediate of compounds of structural formula I bearing a thiazole group at the $R^3$ position.

INTERMEDIATE SCHEME 6:

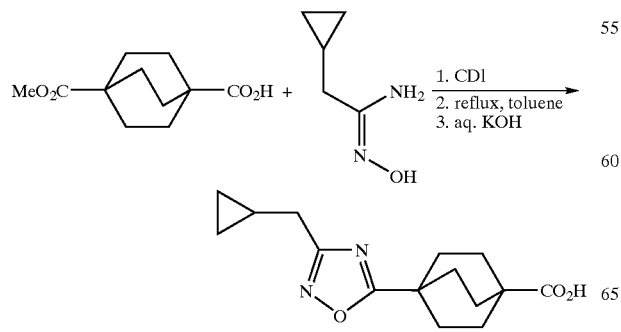

INTERMEDIATE SCHEME 7:

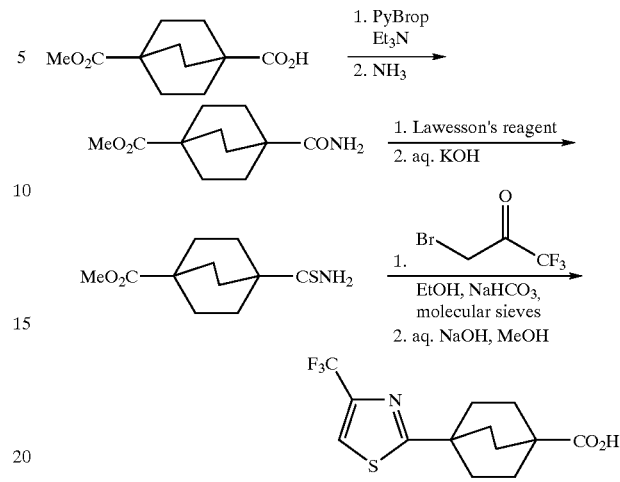

Intermediate Schemes 8–14 show preferred methods for the preparation of bicyclo[2.2.2]octane-1-carboxylic acids intermediates in the synthesis of compounds of structural formula I with various alkyl or alkenyl or substituted alkyl groups at the $R^3$ position. A key reaction is the Wittig reaction performed on a bicyclo[2.2.2]octane-1-carboxaldehyde, as shown in Intermediate Scheme 8. The double bond in the product of this reaction may be hydrogenated to generate an alkyl group of varying length and character (which will become the $R^3$ substituent in structural formula I), depending on the Wittig reagent, as shown in Intermediate Scheme 9. Alternatively, the double bond can be used to introduce other functionality, such as the hydroxy or fluoro group, as shown in Intermediate Scheme 10. The aldehyde itself may be used to provide the difluoromethyl group at position $R^3$, as shown in Intermediate Scheme 11. The alkene product of the Wittig reaction can undergo numerous other transformations, for example, cyclopropanation, as illustrated in Intermediate Scheme 12. Alternatively, the Wittig reagent may contain a remote functional group, for example, a ketal, as illustrated in Intermediate Scheme 13. This functional group may undergo characteristic functional group transformations after the Wittigtreduction sequence, for example, the hydrolysis of a ketal to a ketone, as illustrated in Intermediate Scheme 13, or the reduction of a ketal to an alcohol as illustrated in Intermediate Scheme 14. In this manner compounds of structural formula I with a variety of different $R^3$ substituents may be obtained. The specific examples given are intended to convey general principles and are not intended to limit the scope of the $R^3$ substituents.

INTERMEDIATE SCHEME 8:

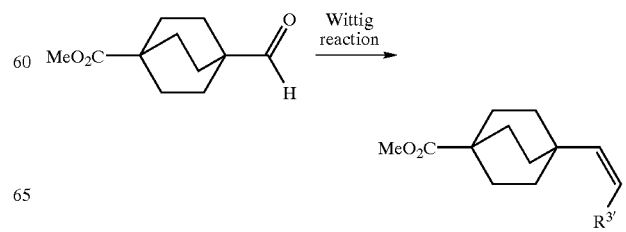

INTERMEDIATE SCHEME 9:

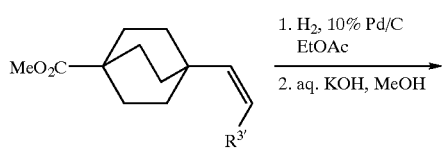

INTERMEDIATE SCHEME 10:

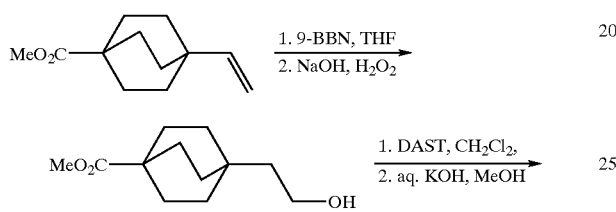

INTERMEDIATE SCHEME 11:

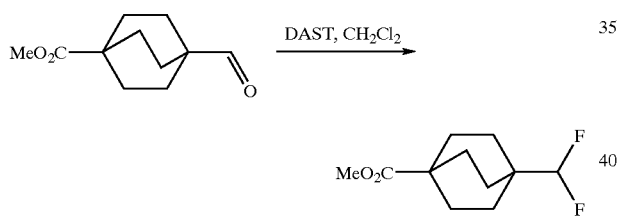

INTERMEDIATE SCHEME 12:

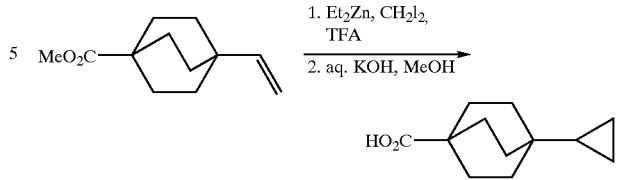

INTERMEDIATE SCHEME 13:

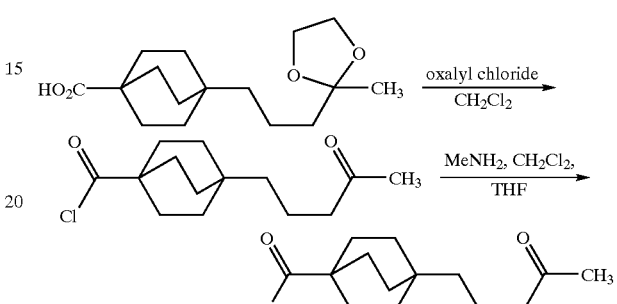

INTERMEDIATE SCHEME 14:

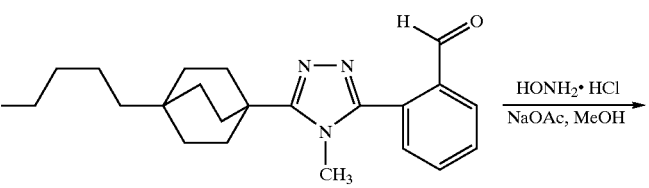

General functional group chemical transformations used to prepare compounds of the present invention are illustrated below in the preparation of specific compounds of the present invention.

These functional group transformations are of a general variety well understood by those skilled in the art.

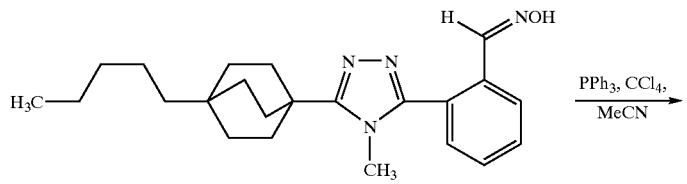

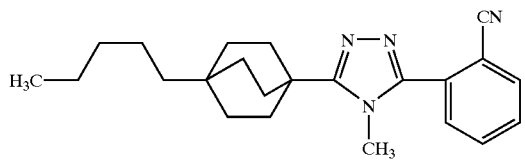

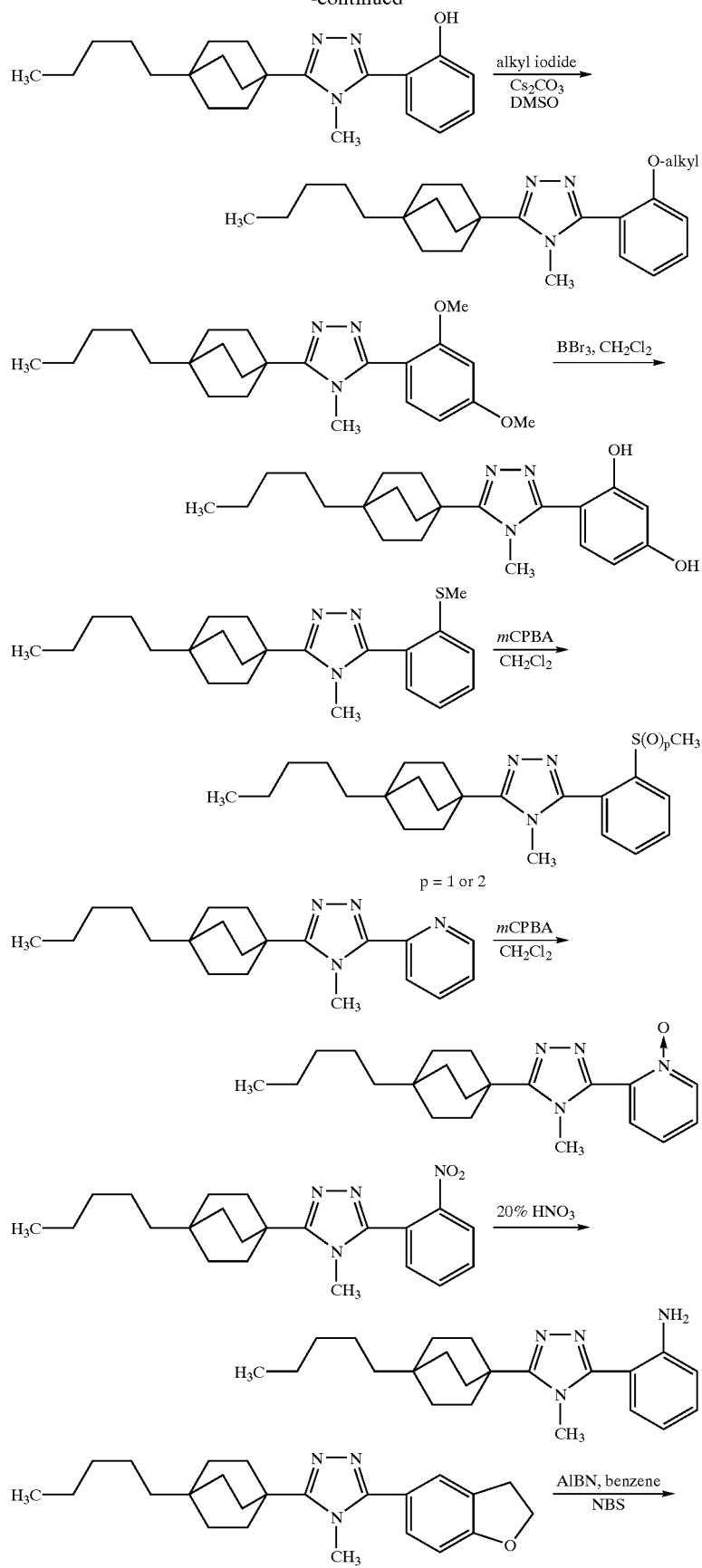

-continued
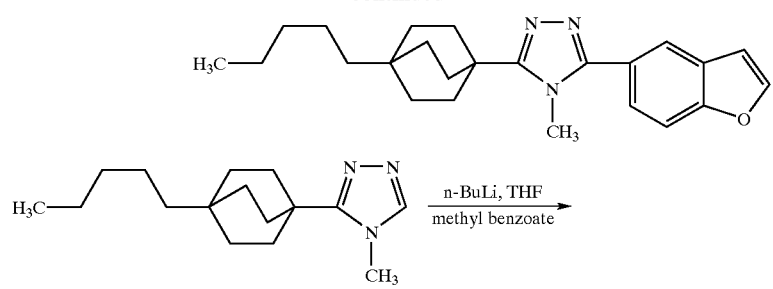
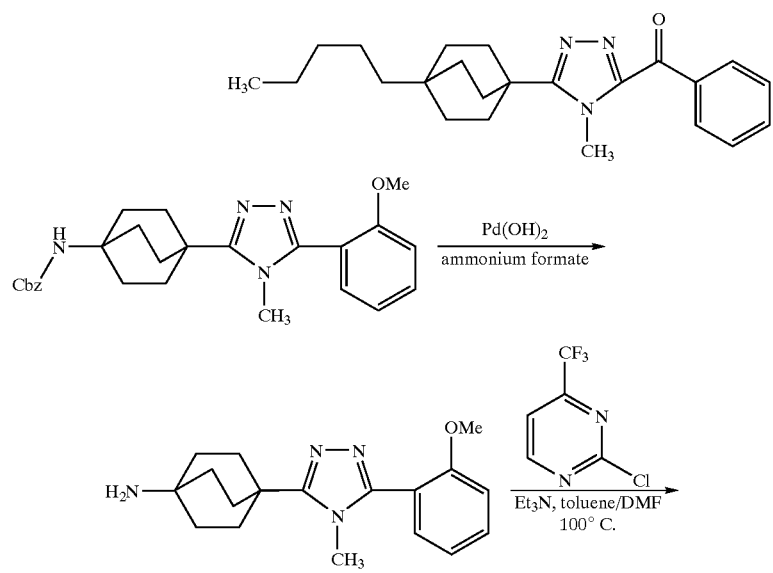
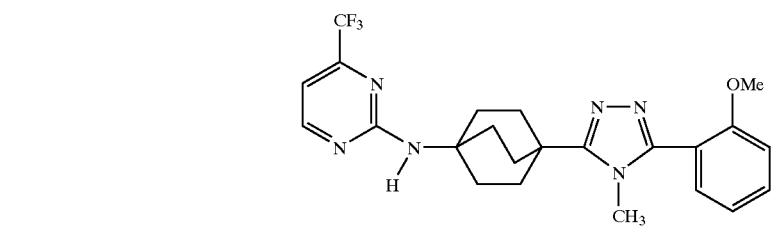
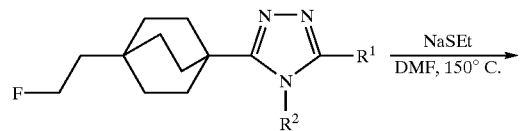
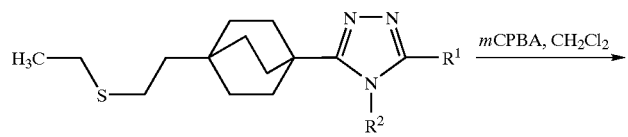
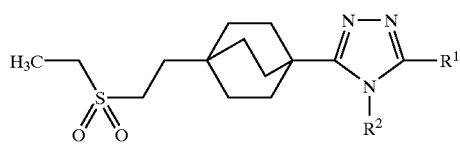
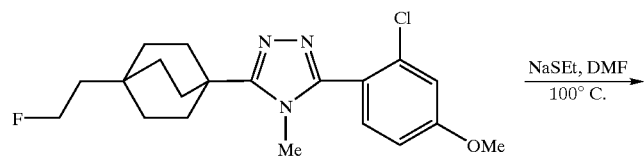

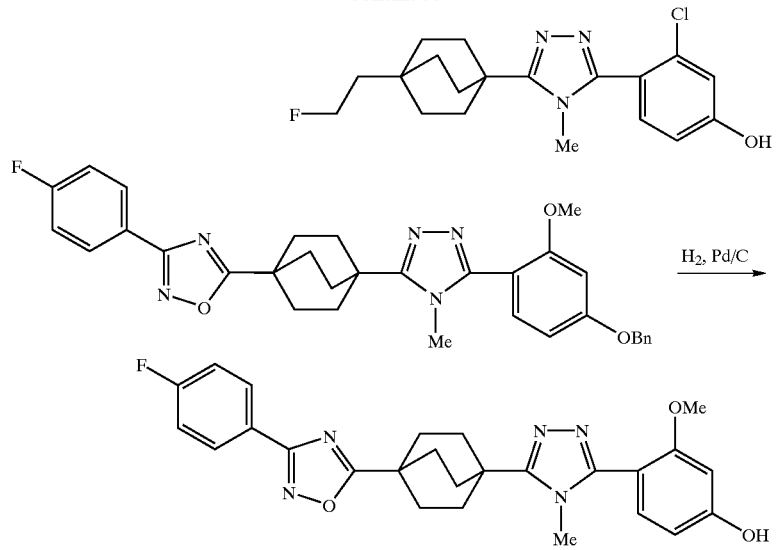

The following Examples are provided to illustrate the invention and are not to be construed as limiting the scope of the invention in any manner.

EXAMPLE 1

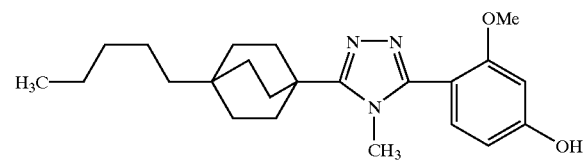

3-Methoxy-4-[4-methyl-5-(4-pentylbicyclo[2.2.2]oct-1-yl)-4H-1,2,4-triazol-3-yl]phenol (1-F)

Step A:

To a magnetically stirred solution of 4-benzyloxy-2-hydroxybenzonitrile (1-A, WO 00/69841) (7.95 g, 35.3 mmol) and iodomethane (5.43 mL, 87.2 mmol) in DMF (90 mL) cooled to −5° was added all at once sodium hydride (60% dispersion, 2.17 g, 54.2 mmol). The mixture was stirred for 30 min, warmed to room temperature and stirred for an additional 2 h. Most of the DMF was removed in vacuo, and the residue was partitioned between water and ethyl acetate. The aqueous phase was extracted three times with ethyl acetate. The combined organic phases were washed with water and saturated brine and dried (MgSO$_4$). The residue after removal of the solvent in vacuo was triturated with hexane and chromatographed on silica gel with hexanes-CH$_2$Cl$_2$ (2:3) to give 4-benzyloxy-2-methoxybenzonitrile (1-B). MS: m/z 240 (M+1); $^1$H NMR (500 MHz, CDCl$_3$): δ 7.47 (d, 1H, J=8.4 Hz), 7.36–7.45 (m,

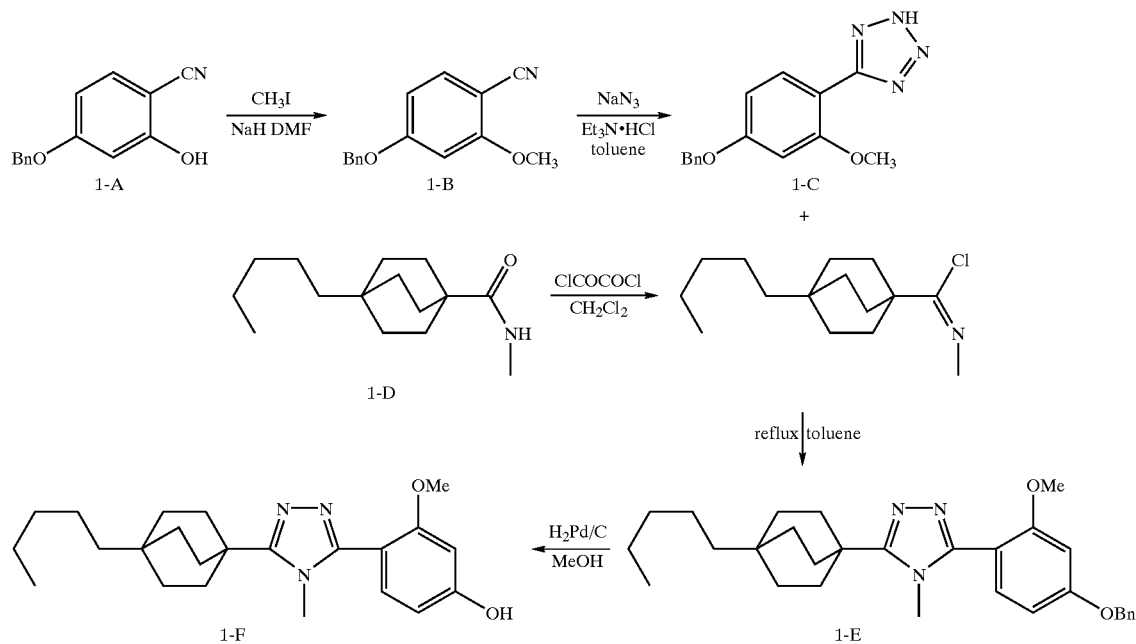

5H), 6.58 (dd, 1H, J=2.3, 8.4 Hz), 6.57 (d, 1H, J=2.3 Hz), 5.10 (s, 2H), 3.88 (s, 3H) ppm.

Step B:

A vigorously stirred suspension of 4-benzyloxy-2-methoxybenzonitrile (1-B) (1.20 g, 5.0 mmol), sodium azide (732 mg, 11.3 mmol), and triethylamine hydrochloride (1.54 g, 11.3 mmol) in toluene (6 mL) was heated at 110° for 48 h. The brown suspension was cooled, water (15 mL) was added, and the mixture stirred for 30 min. The organic layer was separated and extracted with water (5 mL). The combined aqueous extracts were acidified to about pH 1 with concentrated HCl. The gum that initially precipitated solidified upon stirring for 30 min. The solid was filtered, washed with water, and dried to give 5-[4-(benzyloxy)2-methoxyphenyl]-2H-tetrazole (1-C). $^1$H NMR (500 MHz, CDCl$_3$): δ 12.9 (vbs, 1H), 7.37 (d, 1H, J=8.7 Hz), 7.34–7.48 (m, 5H), 6.78 (dd, 1H, J=2.3, 8.7 Hz), 6.70 (d, 1H, J=2.3 Hz), 5.15 (s, 2H), 4.05 (s, 3H) ppm.

Step C:

Oxalyl chloride (3.49 ml, 40 mmol) was added dropwise to a solution of N-methyl-4-pentylbicyclo[2.2.2]octane-1-carboxamide (1-D) (952 mg, 4.0 mmol) in dry CH$_2$Cl$_2$ at room temperature. After the vigorous gas evolution subsided, the solution was stirred at room temperature for 2 h. The CH$_2$Cl$_2$ was removed carefully in vacuo at room temperature and then at 50°. The clear syrupy residue was dissolved in toluene (8 mL) and 5-[4-(benzyloxy)-2-methoxyphenyl]-2H-tetrazole (1-C) (1.13 g, 4.0 mmol) added. The mixture was heated at 120° for 9 h. The mixture was cooled, and the precipitated solid was filtered, washed with toluene and dried to afford the triazole hydrochloride salt. The salt was partitioned between CH$_2$Cl$_2$ and 10% aqueous K$_2$CO$_3$. The aqueous phase was extracted twice with CH$_2$Cl$_2$. The combined CH$_2$Cl$_2$ extracts were dried (MgSO$_4$) and evaporated in vacuo. The residue was chromatographed on silica gel with 5% MeOH/CH$_2$Cl$_2$ to give 3-[4-(benzyloxy)-2-methoxyphenyl]-4-methyl-5-(4-pentylbicyclo[2.2.2]oct-1-yl)-4H-1,2,4-triazole (1-E). MS: m/z 474 (M+1); $^1$H NMR (500 MHz, CDCl$_3$): δ 7.33–7.47 (m, 6H ), 6.65 (dd, 1H, J=2.3, 8.5 Hz), 6.60 (d, 1H, J=2.3 Hz), 5.10 (s, 2H), 3.75 (s, 3H), 3.48 (s, 3H), 2.08 (m, 6H), 1.51 (m, 6H), 1.00–1.35 (m, 8H), 0.89 (t, 3H, J=7.2) ppm.

Step D:

A solution of 3-[4-(benzyloxy)-2-methoxyphenyl]-4-methyl-5-(4-pentylbicyclo[2.2.2]oct-1-yl)-4H-1,2,4-triazole (1-E) (272 mg, 0.572 mmol) in MeOH (8 mL) was hydrogenated for 19 h with 10% Pd/C catalyst (27 mg) at room temperature and atmospheric pressure. The catalyst was filtered and washed with MeOH. The MeOH was removed in vacuo to afford 3-methoxy-4-[4-methyl-5-(4-pentylbicyclo[2.2.2]oct-1-yl)-4H-1,2,4-triazol-3-yl]phenol (1-F). MS: m/z 384 (M+1); $^1$H NMR (500 MHz, DMSO-d$_6$): δ 9.94 (s 1H), 7.09 (d, 1H, J=8.3), 6.53 (d, 1H, J=1.6 Hz), 6.46 (dd, 1H, J=2.2, 8.2 Hz), 3.72 (s, 3H), 3.40 (s, 3H), 1.95 (m, 6H), 1.44 (m, 6H), 1.07–1.33 (m, 8H), 0.86 (t, 3H, J=7.2).

EXAMPLE 2

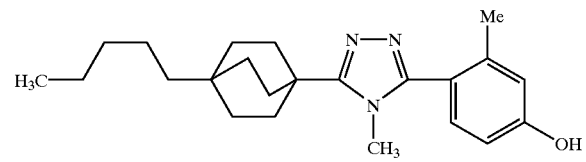

3-Methyl-4-[4-methyl-5-(4-pentylbicyclo[2.2.2]oct-1-yl)-4H-1,2,4-triazol-3-yl]phenol (2-G)

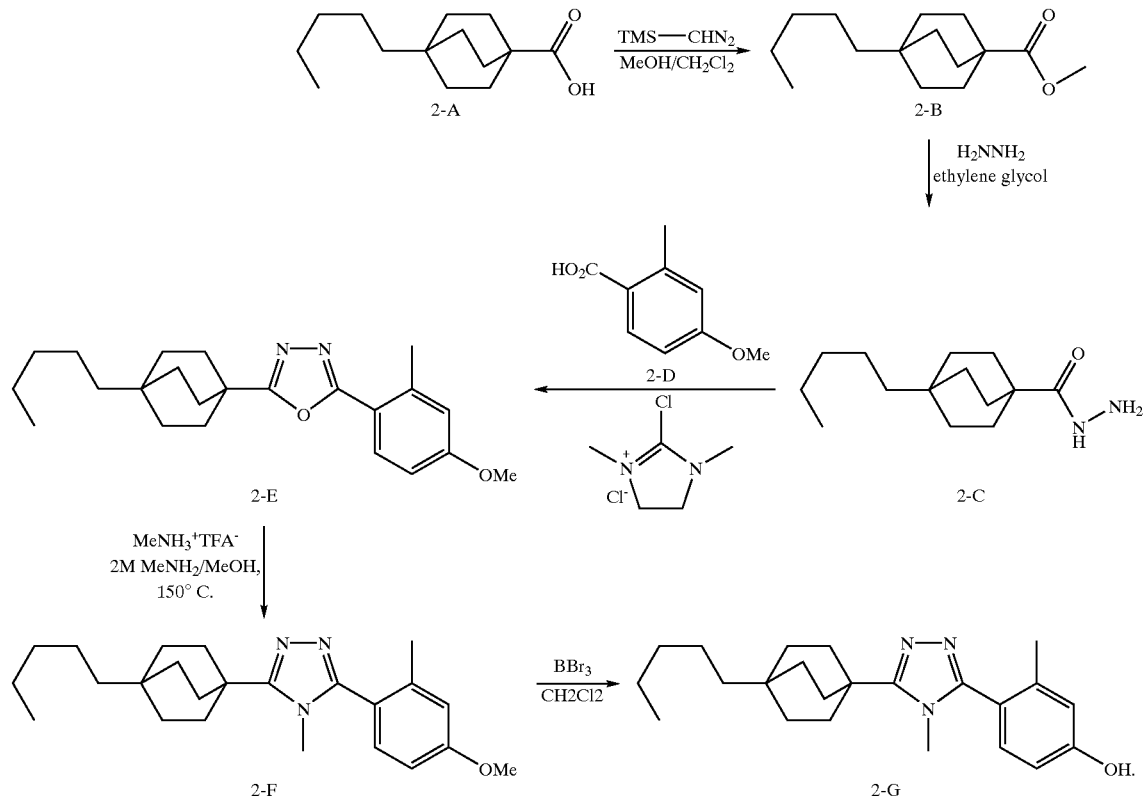

Step A:

(Trimethylsilyl)diazomethane (2M/hexane, 53 mL, 106 mmol) was added slowly to a solution of 4-pentylbicyclo[2.2.2]octane-1-carboxylic acid (2-A) (20.3 g, 90.6 mmol) in methylene chloride (100 mL) and methanol (40 mL) until the yellow color persisted. After stirring for 10 min at room temperature, the solution was concentrated in vacuo to give methyl 4-pentylbicyclo[2.2.2]octane-1-carboxylate (2-B). $^1$H NMR (500 MHz, CDCl$_3$): δ 0.89 (t, 3H); 1.20 (m, 8H); 1.39 (m, 6H); 1.77 (m, 6H); 3.65 (s, 3H) ppm.

Step B:

Hydrazine (anhydrous, 103 mL, 88.7 mmol) was added to a solution of methyl 4-pentylbicyclo[2.2.2]octane-1-carboxylate (2-B) in ethylene glycol (180 mL) and the mixture was stirred under reflux for 17 h. After cooling to room temperature, the mixture was poured into water (1500 mL) and extracted with methylene chloride (3×600 mL). The combined extracts were washed twice with water, brine, dried (MgSO$_4$) and concentrated in vacuo to provide 4-pentylbicyclo[2.2.2]octane-1-carbohydrazide (2-C). $^1$H NMR (500 MHz, CDCl$_3$): δ 0.90 (t, 3H); 1.21 (m, 8H); 1.43 (m, 6H); 1.74 (m, 6H); 3.85 (broad s, 2H); 6.81 (broad s, 1H) ppm.

Step C:

2-Chloro-1,3-dimethyl-4,5-dihydro-1H-imidazol-3-ium chloride (5.07 g, 30.0 mmol) was added to a solution of 2-methyl-4-methoxybenzoic acid (2-D) (856 mg, 5.0 mmol) and 4-pentylbicyclo[2.2.2]octane-1-carbohydrazide (2-C) (1.25 g, 5.25 mmol) in methylene chloride (60 mL) followed by triethylamine (8.36 mL, 60 mmol) and the mixture stirred at room temperature for 48 h. The mixture was diluted with methylene chloride and washed with water, 1N HCl, 10% NaHCO$_3$, brine, dried (MgSO$_4$) and concentrated in vacuo. The residue was purified by column chromatography (silica gel, hexane:ethyl acetate, 9:1) to give 2-(4-methoxy-2-methylphenyl)-5-(4-pentylbicyclo[2.2.2]oct-1-yl)-1,3,4-oxadiazole (2-E) Mass spectrum: 369 (M+1); $^1$H NMR (500 MHz, CDCl$_3$): δ 0.93 (t, 3H); 1.27 (m, 8H); 1.56 (m, 6H); 2.03 (m, 6H); 2.70 (s, 3H); 3.89 (s, 3H); 6.86 (m, 2H); 7.89 (d, 1H) ppm.

Step D:

2-(4-Methoxy-2-methylphenyl)-5-(4-pentylbicyclo[2.2.2]oct-1-yl)-1,3,4-oxadiazole (2-E) (988 mg, 2.68 mmol), methylammonium trifluoroacetate (9.72 g, 67 mmol, prepared by combining equimolar amounts of methylamine and trifluoroacetic acid in ether followed by concentration in vacuo), and methylamine (2M/MeOH, 33 mL, 67 mmol) were stirred together in a glass bomb at 150° C. for 114 h. The mixture was concentrated in vacuo and the residue partitioned with methylene chloride and water. The aqueous phase was extracted with methylene chloride and the combined extracts washed with brine, dried (MgSO$_4$) and concentrated in vacuo. The residue was purified by column chromatography (silica gel, ethyl acetate:hexane, 7:3, then 9:1) to give 3-(4-methoxy-2-methylphenyl)-4-methyl-5-(4-pentylbicyclo[2.2.2]oct-1-yl)-4H-1,2,4-triazole (2-F). Mass spectrum: 382 (M+1); $^1$H NMR (500 MHz, CDCl$_3$): δ 0.93 (t, 3H); 1.27 (m, 8H); 1.56 (m, 6H); 2.12 (m, 6H); 2.18 (s, 3H); 3.49 (s, 3H); 3.87 (s, 3H); 6.85 (m, 2H); 7.24 (d, 1H) ppm.

Step E:

Boron tribromide (1M/CH$_2$Cl$_2$, 3.21 mL, 3.21 mmol) was added to a solution of 3-(4-methoxy-2-methylphenyl)-4-methyl-5-(4-pentylbicyclo[2.2.2]oct-1-yl)-4H-1,2,4-triazole (2-F) (410 mg, 1.07 mmol) in methylene chloride (6 mL) at 0° C. The mixture was stirred at room temperature for 2 h. The solution was washed with water, 10% NaHCO$_3$, dried (MgSO$_4$) and concentrated in vacuo. The residue was purified by preparative TLC (silica gel, MeOH:methylene chloride, 5:95) to provide 3-methyl-4-[4-methyl-5-(4-pentylbicyclo[2.2.2]oct-1-yl)-4H-1,2,4-triazol-3-yl]phenol (2-G). Mass spectrum: 393 (M+1); $^1$H NMR (500 MHz, CDCl$_3$): δ 0.93 (t, 3H); 1.27 (m, 8H); 1.56 (m, 6H); 1.97 (s 3H); 2.12 (m, 6H); 3.50 (s, 3H); 6.65 (m, 2H); 6.98 (d, 1H) ppm.

EXAMPLE 3

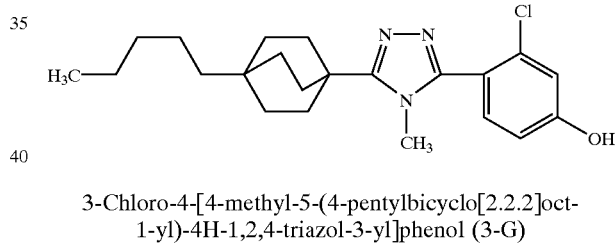

3-Chloro-4-[4-methyl-5-(4-pentylbicyclo[2.2.2]oct-1-yl)-4H-1,2,4-triazol-3-yl]phenol (3-G)

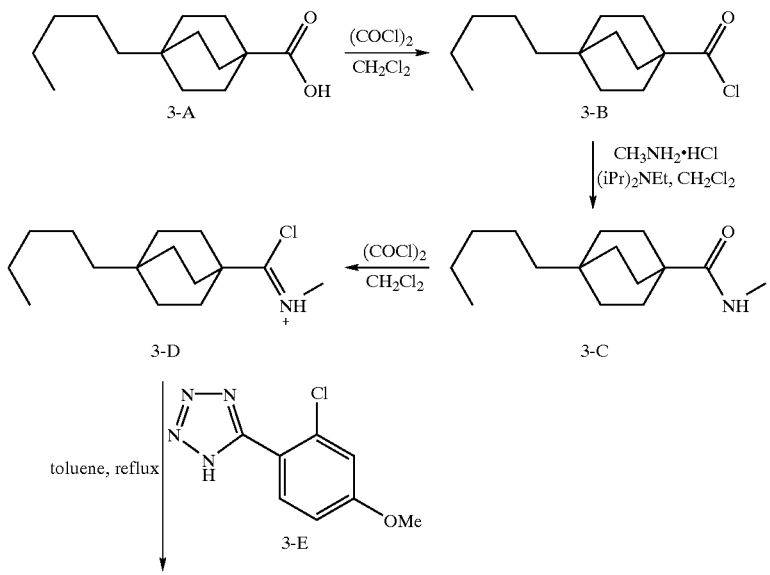

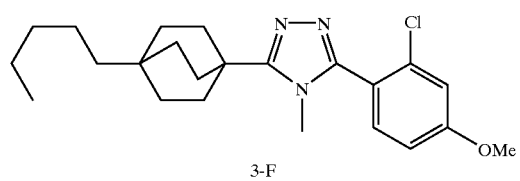

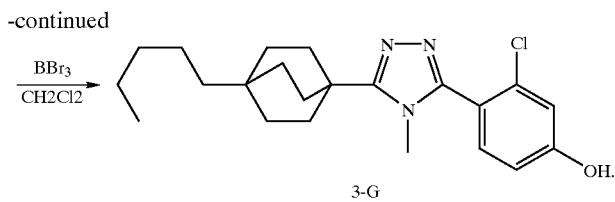

Step A:

Oxalyl chloride (505 μL, 5.79 mmol) was added dropwise to a mixture of 4-pentylbicyclo[2.2.2]octane-1-carboxylic acid (3-A) in methylene chloride (10 mL). The solution was stirred at room temperature for 3 h and then concentrated in vacuo to give 4-pentylbicyclo[2.2.2]octane-1-carbonyl chloride (3-B). $^1$H NMR (500 MHz, CDCl$_3$): δ 0.90 (t, 3H); 1.21 (m, 8H); 1.45 (m, 6H); 1.88 (m, 6H) ppm.

Step B:

N,N-Diisopropylethylamine (1.44 mL, 11.1 mmol) was added to a mixture of 4-pentylbicyclo[2.2.2]octane-1-carboxylic acid (3-A) (1.09 g, 4.45 mmol) and methylamine hydrochloride (1.5 g, 22.3 mmol) in methylene chloride (10 mL) was added and the mixture stirred at room temperature for 18 h. After diluting with methylene chloride, the mixture was washed with water, brine, dried (MgSO$_4$) and concentrated in vacuo to give N-methyl-4-pentylbicyclo[2.2.2]octane-1-carboxamide (3-C). $^1$H NMR (500 MHz, CDCl$_3$): δ 0.91 (t, 3H); 1.22 (m, 8M); 1.43 (m, 6H); 1.77 (m, 6H); 2.82 (d, 3H) ppm.

Step C:

Oxalyl chloride (846 μL, 9.7 mmol) was added dropwise to a solution of N-methyl-4-pentylbicyclo[2.2.2]octane-1-carboxamide (3-C) (230 mg, 0.97 mmol) in methylene chloride (2.0 mL) and the mixture stirred at room temperature for 4 h. The solvent and excess reagent were removed in vacuo to provide N-methyl-4-pentylbicyclo[2.2.2]octane-1-carboximidoyl chloride (3-D). Toluene (1.5 mL) was added followed by 5-(2-chloro-4-methoxyphenyl)-1H-tetrazole (3-E) (204 mg, 0.97 mmol) and the mixture refluxed for 18 h. The reaction was cooled to room temperature and the precipitate was filtered, washed with cold toluene, hexane, dissolved in methylene chloride, dried (MgSO$_4$) and concentrated in vacuo to provide 3-(2-chloro-4-methoxyphenyl)-4-methyl-5-(4-pentylbicyclo[2.2.2]oct-1-yl)-4H-1,2,4-triazole (3-F). Mass spectrum: 402 (M+1); $^1$H NMR (500 MHz, CDCl$_3$): δ 0.94 (t, 3H); 1.27 (m, 8H); 1.56 (m, 6H); 2.13 (m, 6H); 3.56 (s, 3H); 3.89 (s, 3H); 6.95 (dd, 1H); 7.07 (d, 1H); 7.43 (d, 1H).

Step D:

Boron tribromide (135 μL, 1.43 mmol) was added dropwise to a solution of 3-(2-chloro-4-methoxyphenyl)-4-methyl-5-(4-pentylbicyclo[2.2.2]oct-1-yl)-4H-1,2,4-triazole (3-F) (287 mg, 0.714 mmol) in methylene chloride (5 mL) at 0° C. The mixture was stirred at room temperature for 2.5 h. The solution was washed with water, 10% NaHCO$_3$, dried (MgSO$_4$) and concentrated in vacuo and the residue purified by column chromatography (silica gel, 5% MeOH/methylene chloride) to provide 3-chloro-4-[4-methyl-5-(4-pentylbicyclo[2.2.2]oct-1-yl)-4H-1,2,4-triazol-3-yl]phenol (3-G). Mass spectrum: 388 (M+1); $^1$H NMR (500 MHz, CDCl$_3$); δ 0.93 (t, 3H); 1.26 (m, 8H); 1.56 (m, 6H); 2.13 (m, 6H); 3.58 (s, 3H); 6.69 (dd, 1H); 6.92 (d, 1H); 7.09 (d 1H) ppm.

EXAMPLE 4

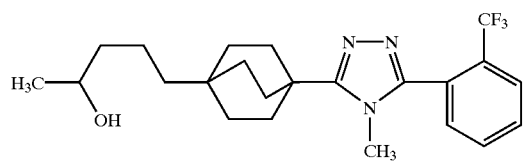

5-(4-{1-Methyl-5-[2-(trifluoromethyl)phenyl]-1-H-1,2,4-triazol-3-yl}bicyclo[2.2.2]oct-1-yl)pentan-2-ol
(4-J)

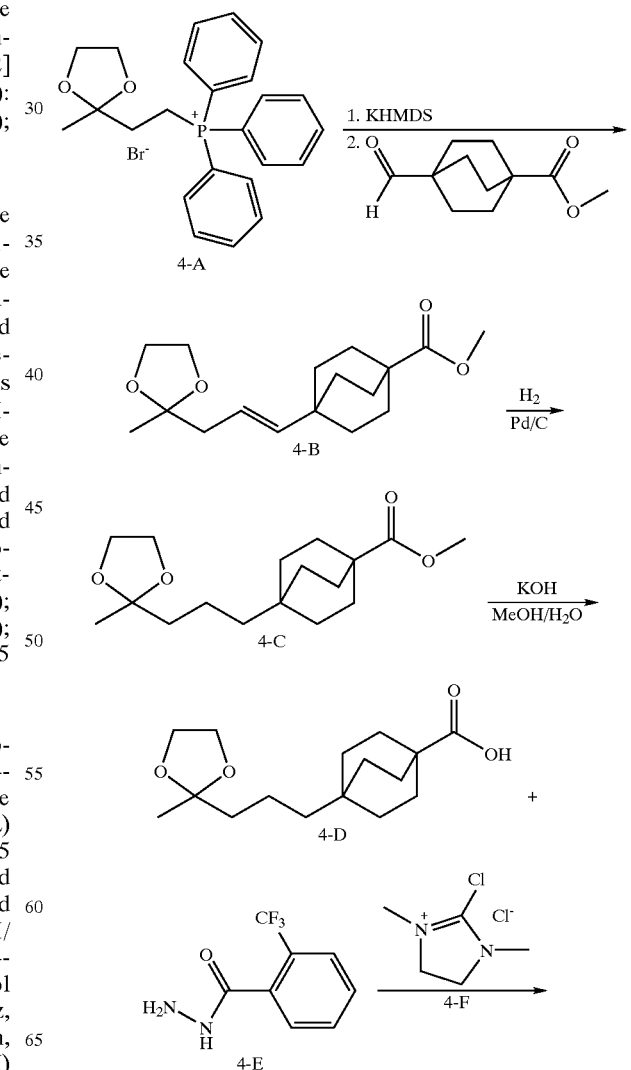

-continued

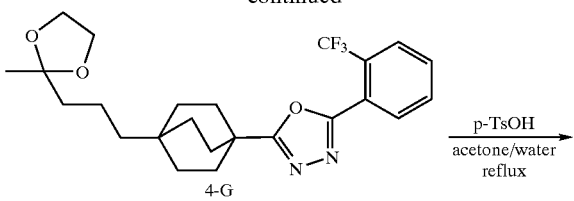
4-G p-TsOH
acetone/water
reflux

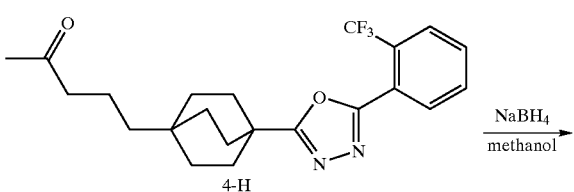
4-H

NaBH₄
methanol

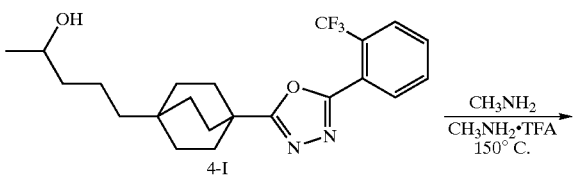
4-I

CH₃NH₂
CH₃NH₂·TFA
150° C.

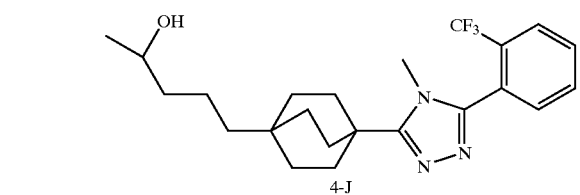
4-J

Step A:
[2-(2-Methyl-1,3-dioxolan-2-yl)ethyl](triphenyl)phosphonium bromide (4-A, *Synthesis*: 532 (1986)) (5.99 g, 12.7 mmol) was stirred in dry THF (200 mL). Potassium bis(trimethylsilyl)amide (20.4 mL, 2M soln in toluene, 10.2 mmol) was added. The reaction was allowed to stir for 30 min. The reaction mixture was then cooled to −78° C. Methyl 4-formylbicyclo[2.2.2]octane-1-carboxylate was added at −78° C. by cannula. The reaction was allowed to warm to room temperature overnight. The volume was reduced by evaporation of THF in vacuo. 100 mL of water was added. The mixture was then layered with 100 mL of diethyl ether. The ether was extracted and dried (MgSO₄). The product (methyl 4-[(1E)-3-(2-methyl-1,3-dioxolan-2-yl)prop-1-enyl]bicyclo[2.2.2]octane-1-carboxylate (4-B)) was purified by flash chromatography on silica gel with 10/90 ethyl acetate-hexane mixture.

Step B:
Methyl 4-[(1E)-3-(2-methyl-1,3-dioxolan-2-yl)prop-1-enyl]bicyclo[2.2.2]octane-1-carboxylate (4-B) (1.1 g) was stirred in ethanol (75 mL). A spatula tip scoop of 10% Pd on carbon (150 mg) was added. A hydrogen balloon was added and the mixture was stirred under hydrogen atmosphere for 3 h. The palladium-on-carbon was filtered and the ethanol was removed in vacuo to yield methyl 4-[3-(2-methyl-1,3-dioxolan-2-yl)propyl]bicyclo[2.2.2]octane-1-carboxylate (4-C).

Step C:
Methyl 4-[3-(2-methyl-1,3-dioxolan-2-yl)propyl]bicyclo[2.2.2]octane-1-carboxylate (4-C) (1.0 g, 3.38 mmol) was stirred in a solution of 90% methanol and 10% water (50 mL). Excess potassium hydroxide (2.0 g) was added. The mixture was refluxed overnight. The cooled mixture was acidified with 1N hydrochloric acid (100 mL) and then washed twice with ethyl acetate (100 mL). The combined organic layers were dried (MgSO₄). Ethyl acetate was removed in vacuo yielding pure 4-[3-(2-methyl-1,3-dioxolan-2-yl)propyl]bicyclo[2.2.2]octane-1-carboxylic acid (4-D).

Step D:
4-[3-(2-Methyl-1,3-dioxolan-2-yl)propyl]bicyclo[2.2.2]octane-1-carboxylic acid (4-D) (0.200 g, 0.708 mmol) was combined with 2-(trifluoromethyl)benzoic hydrazide (4-E) (0.173 g, 0.847 mmol) and azeotroped twice from toluene. The mixture was then stirred in dry methylene chloride (10 mL). 2-Chloro-1,3-dimethylimidazolinium chloride (4-F) (0.718 g, 4.25 mmol) was added followed by 1.184 mL of triethylamine. The reaction was allowed to stir for 2 h. The reaction was diluted with methylene chloride and was washed with water. The resulting oxadiazole, 2-{4-[3-(2-methyl-1,3-dioxolan-2-yl)propyl]bicyclo[2.2.2]oct-1-yl}-5-[2-(trifluoromethyl)phenyl]-1,3,4-oxadiazole (4-G) was purified by flash chromatography on silica gel with 50/50 ethyl acetate-hexane mixture.

Step E:
2-{4-[3-(2-Methyl-1,3-dioxolan-2-yl)propyl]bicyclo[2.2.2]oct-1-yl }-5-[2-(trifluoromethyl)phenyl]-1,3,4-oxadiazole (4-G) (0.158 g) was stirred in a mixure of 90% acetone/10% water (20 mL). p-Toluenesulfonic acid (10 mg) was added to the solution. The reaction was heated to reflux for 1 h. The volume was reduced by evaporation of acetone in vacuo. The mixture was then layered with ethyl acetate (25 mL) and saturated sodium bicarbonate solution (25 mL). The ethyl acetate layer was extracted and dried (MgSO₄). Solvent was removed in vacuo to afford pure 5-(4-{5-[2-(trifluoromethyl)phenyl]-1,3,4-oxadiazol-2-yl}bicyclo[2.2.2]oct-1-yl)pentan-2-one (4-H).

Step F:
5-(4-{5-[2-(Trifluoromethyl)phenyl]-1,3,4-oxadiazol-2-yl}bicyclo[2.2.2]oct-1-yl)pentan-2-one (4-H) (0.072 g) was stirred in methanol (2 mL) at 0° C. Sodium borohydride (20 mg) was added. The reaction was allowed to stir to room temperature. The mixture was then layered with ethyl acetate (15 mL) and water (15 mL). The ethyl acetate layer was extracted and dried (MgSO₄). Solvent was removed in vacuo to afford pure 5-(4-{5-[2-(trifluoromethyl)phenyl]-1,3,4-oxadiazol-2-yl}bicyclo[2.2.2]oct-1-yl)pentan-2-ol (4-I).

Step G:
5-(4-{5-[2-(Trifluoromethyl)phenyl]-1,3,4-oxadiazol-2-yl}bicyclo[2.2.2]oct-1-yl)pentan-2-ol (4-I) (50 mg) was placed in a sealed vial in a solution of 2M methylamine in methanol (2.5 mL). A small spatula scoop of methylamine TFA salt was added and the vial was sealed. The sealed vial was heated to 150° C. for 3 d. The reaction was diluted with ethyl acetate (15 mL), washed with water (15 mL), and dried (MgSO₄). Ethyl acetate was removed in vacuo. The product, 5-(4-{1-methyl-5-[2-(trifluoromethyl)phenyl]-1-H-1,2,4-triazol-3-yl}bicyclo[2.2.2]oct-1-yl)pentan-2-ol (4-J), was purified by preparative reverse phase HPLC on a C-18 silica gel column using a gradient of acetonitrile-water buffered with 0.1% trifluoroacetic acid. The effluent containing the pure triazole was made basic with 10% NaHCO₃, evaporated in vacuo to remove most of the acetonitrile, and extracted with methylene chloride. The organic extract was dried (MgSO$_4$) and evaporated, and the residue dried under vacuum to provide the desired compound. MS (ESI$^+$)=422.5 (M+1); $^1$H NMR (500 MHz, CDCl$_3$): δ 1.21 (2H, m), 1.23 (3H, d, J=6.5 Hz), 1.29 (2H, m), 1.57 (6H, m), 2.13 (6H, m), 3.47 (3H, s), 3.85 (1H, m), 7.51 (1H, m), 7.70 (2H, m), 7.85 (1H, m) ppm.

EXAMPLE 5

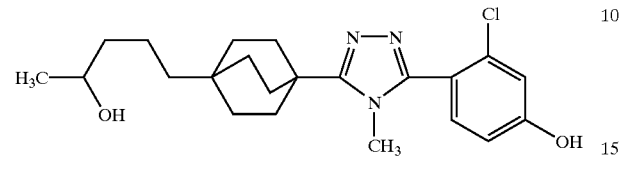

3-Chloro-4-{5-[4-(4-hydroxypentyl)bicyclo[2.2.2]oct-1-yl]-1-methyl-1-H-1,2,4-triazol-3-yl}phenol (5-K)

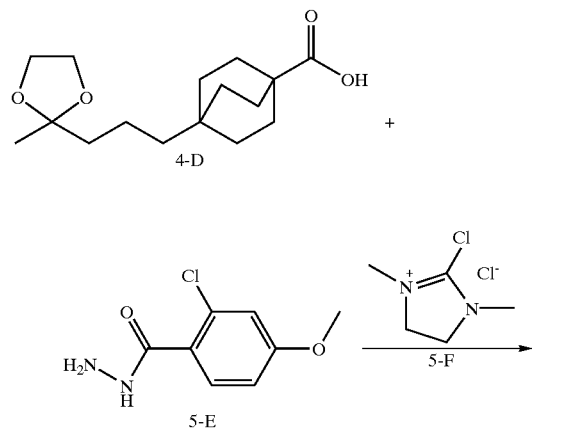

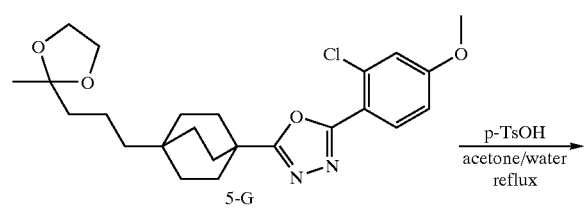

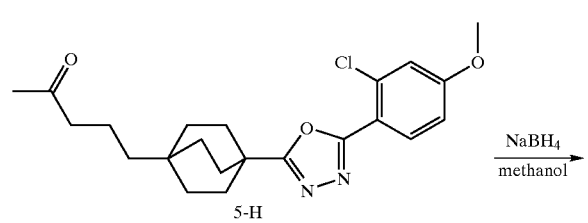

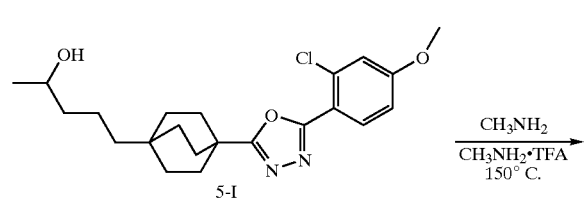

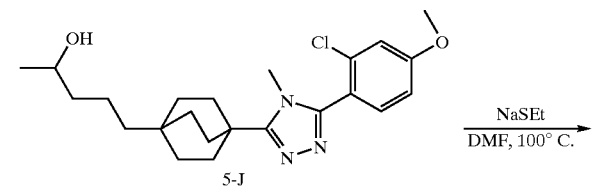

Step A:
4-[3-(2-Methyl-1,3-dioxolan-2-yl)propyl]bicyclo[2.2.2]octane-1-carboxylic acid (4-D) (0.300 g, 1.06 mmol) was combined with 2-chloro-4-methoxybenzohydrazide (5-E) (0.255 g, 1.275 mmol) and azeotroped twice from toluene. The mixture was then stirred in dry methylene chloride (15 mL). 2-Chloro-1,3-dimethylimidazolinium chloride (5-F) (1.075 g, 6.36 mmol) was added followed by 1.77 mL of triethylamine. The reaction was allowed to stir for 2 h. The reaction was diluted with methylene chloride and was washed with water. The resulting oxadiazole, 2-(2-chloro-4-methoxyphenyl)-5-{4-[3-(2-methyl-1,3-dioxolan-2-yl)propyl]bicyclo[2.2.2]oct-1-yl}-1,3,4-oxadiazole (5-G) was purified by flash chromatography on silica gel with 50/50 ethyl acetate-hexane mixture.

Step B:
2-(2-Chloro-4-methoxyphenyl)-5-{4-[3-(2-methyl-1,3-dioxolan-2-yl)propyl]bicyclo[2.2.2]oct-1-yl}-1,3,4-oxadiazole (5-G) (0.200 g) was stirred in a mixure of 90% acetone/10% water (20 mL). p-Toluenesulfonic acid (15 mg) was added to the solution. The reaction was heated to reflux for 1 h. The volume was reduced by evaporation of acetone in vacuo. The mixture was then layered with ethyl acetate (25 mL) and saturated sodium bicarbonate solution (25 mL). The ethyl acetate layer was extracted and dried (MgSO$_4$). Solvent was removed in vacuo to afford pure 5-{4-[5-(2-chloro-4-methoxyphenyl)-1,3,4-oxadiazol-2-yl]bicyclo[2.2.2]oct-1-yl}pentan-2-one (5-H).

Step C:
5-{4-[5-(2-Chloro-4-methoxyphenyl)-1,3,4-oxadiazol-2-yl]bicyclo[2.2.2]oct-1-yl}pentan-2-one (5-H) (0.150 g, 0.373 mmol) was stirred in methanol (5 mL) at 0° C. Sodium borohydride (0.0169 g, 0.448 mmol) was added. The reaction was allowed to stir to room temperature. The mixture was then layered with ethyl acetate (20 mL) and water (20 mL). The ethyl acetate layer was extracted and dried (MgSO$_4$). Solvent was removed in vacuo to afford 5-{4-[5-(2-chloro-4-methoxyphenyl)-1,3,4-oxadiazol-2-yl]bicyclo[2.2.2]oct-1-yl}pentan-2-ol (5-I).

Step D:
5-{4-[5-(2-Chloro-4-methoxyphenyl)-1,3,4-oxadiazol-2-yl]bicyclo[2.2.2]oct-1-yl}pentan-2-ol (5-I) (50 mg) was placed in a sealed vial in a solution of 2M methylamine in methanol (2.5 mL). A small spatula scoop of methylamine TFA salt was added and the vial was sealed. The sealed vial was heated to 150° C. for 24 h. The reaction was diluted with ethyl acetate (15 mL), washed with water (15 mL), and dried (MgSO$_4$). Ethyl acetate was removed in vacuo. The product, 5-{4-[5-(2-chloro-4-methoxyphenyl)-1-methyl-1-H-1,2,4-triazol-3-yl]bicyclo[2.2.2]oct-1-yl}pentan-2-ol (5-J), as purified by preparative TLC with 5% methanol/95% ethyl acetate.

Step E:

5-{4-[5-(2-Chloro-4-methoxyphenyl)-1-methyl-1-H-1,2,4-triazol-3-yl]bicyclo[2.2.2]oct-1-yl}pentan-2-ol (5-J) (0.036 g, 0.086 mmol) was placed in a small vial with 0.5 mL of DMF. Sodium ethanethiolate (0.0218 g, 0.260 mmol) was added to the solution. The vial was sealed and heated to 100° C. for 1.5 h. The incomplete reaction required another 1.5 equivalents of sodium ethanethiolate (0.011 g). The vial was resealed and heated at 100° C. for 1 h. The product, 3-chloro-4-{5-[4-(4-hydroxypentyl)bicyclo[2.2.2]oct-1-yl]-1-methyl-1-H-1,2,4-triazol-3-yl}phenol (5-K) was purified by preparative reverse phase HPLC on a C-18 silica gel column using a gradient of acetonitrile-water buffered with 0.1% trifluoroacetic acid. The effluent containing the pure triazole was made basic with 10% NaHCO$_3$, evaporated in vacuo to remove most of the acetonitrile, and extracted with methylene chloride. The organic extract was dried (MgSO$_4$) and evaporated, and the residue dried under vacuum to provide the desired compound. MS (ESI$^+$)=404.4 (M+1).

EXAMPLE 6

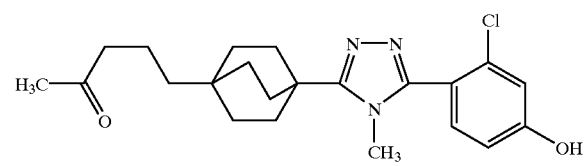

5-{4-[5-(2-chloro-4-hydroxyphenyl)-4-methyl-4H-1,2,4-triazol-3-yl]bicyclo[2.2.2]oct-1-yl}pentan-2-one (6-L)

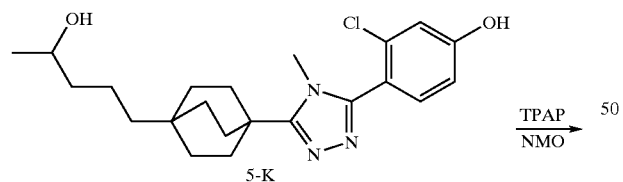

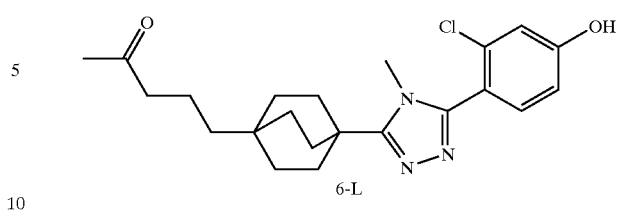

3-Chloro-4-{5-[4-(4-hydroxypentyl)bicyclo[2.2.2]oct-1-yl]-4-methyl-4H-1,2,4-triazol-3-yl}phenol (5-K) (0.0035 g, 0.00869 mmol) was stirred in 0.5 mL of dry methylene chloride over activated 4 Å sieves. N-methylmorpholine N-oxide (0.0015 g, 0.013 mmol) was added. The mixture was allowed to stir under N$_2$ for 15 min. Tetrapropylammonium perruthenate (0.00112 g, 0.00956 mmol) was added and the reaction was allowed to stir for 2 h. The mixture was filtered through celite filtering agent. The product, 5-{4-[5-(2-chloro-4-hydroxyphenyl)-4-methyl4H-1,2,4-triazol-3-yl]bicyclo[2.2.2]oct-1-yl}pentan-2-one (6-L), was purified by preparative reverse phase HPLC on a C-18 silica gel column using a gradient of acetonitrile-water buffered with 0.1% trifluoroacetic acid. The effluent containing the pure triazole was basified with 10% NaHCO$_3$, evaporated in vacuo to remove most of the acetonitrile, and extracted with methylene chloride. The organic extract was dried (MgSO$_4$) and evaporated, and the residue dried under vacuum to provide the desired compound. MS (ESI$^+$)=402.3 (M+1).

EXAMPLE 7

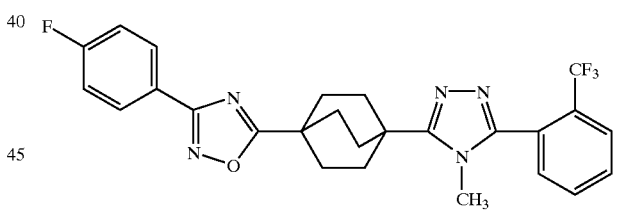

3-(4-Fluorophenyl)-5-[4-[4-methyl-5-[2-(trifluoromethyl)phenyl]-4H-1,2,4-triazol-3-yl]bicyclo[2.2.2]oct-1-yl]-1,2,4-oxadiazole (7-F)q2

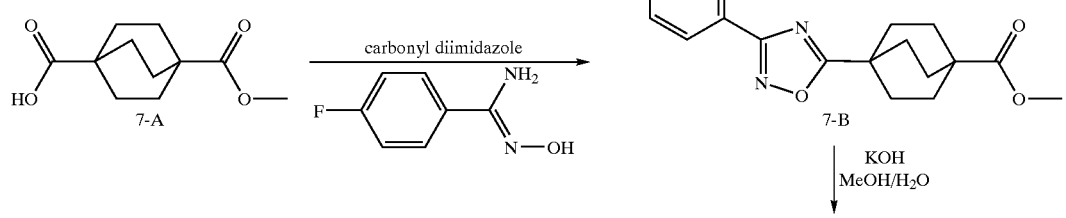

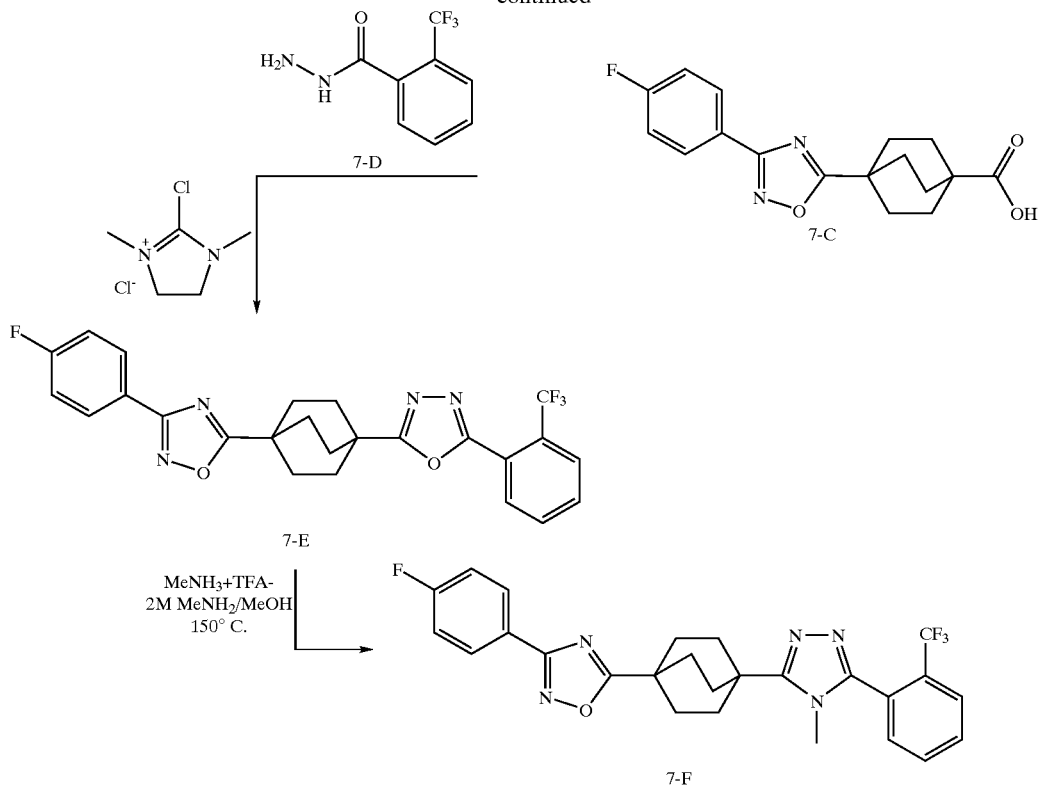

Step A:

To a suspension of 4-(methoxycarbonyl)bicyclo[2.2.2]octane-1-carboxylic acid (7-A) (0.906 g, 4.27 mmol) in dichloromethane (20 mL) was added 1,1'-carbonyldiimidazole (1.04 g, 6.41 mmol). The reaction turned into a clear solution instantly with evolving of gas. After the mixture was stirred at room temperature for 1 h, 4-fluorobenzamidoxime was added (1.98 g, 12.8 mmol). Stirring was continued overnight. The mixture was then concentrated and the residue was refluxed in toluene for 16 h. The mixture was concentrated and the residue was purified by column chromatography using hexane/ethyl acetate as eluent (7/1) to give methyl 4-[3-(4-fluorophenyl)-1,2,4-oxadiazol-5-yl]bicyclo[2.2.2]octane-1-carboxylate acid (7-B) as a white solid. $^1$H NMR (500 MHz, CDCl$_3$) δ 1.96–1.99 (m, 6H), 2.08–2.14 (m, 6H), 3.71 (s, 3H), 7.16–7.20 (m, 2H), 8.08–8.10 (m, 2H) ppm. ESI-MS m/z (M+H) 349.2.

Step B:

The ester (7-B) (1.01 g, 3.06 mmol) was treated with KOH (0.52 g, 9.18 mmol) in methanol/water (95/5, 20 mL). After it was heated at 60° C. for 12 h, the reaction mixture was concentrated, diluted with water, extracted twice with ethyl acetate. The aqueous layer was acidified with 1N HCl aqueous solution and a white solid precipitated out. The solid 4-[3-(4-fluorophenyl)-1,2,4-oxadiazol-5-yl]bicyclo[2.2.2]octane-1-carboxylic acid (7-C) was collected and further dried by co-evaporating with toluene. ESI-MS m/z (M+H) 317.2.

Step C:

A mixture of the acid (7-C) (138.9 mg, 0.439 nmol) and 2-(trifluoromethyl)benzoic hydrazide (7-D) (89.7 mg, 0.439 mmol) was first co-evaporated with toluene three times. Dichloromethane (7 mL) was added to the mixture as solvent. To the resulting suspension was added 2-chloro-1,3-dimethylimidazolinium chloride (743 mg, 4.39 mmol) followed by triethylamine (1.2 mL, 8.78 mmol). The mixture was allowed to stir at room temperature under nitrogen for 48 h to ensure the completion of the reaction. The reaction mixture was then diluted with dichloromethane, washed with water, 1N HCl, saturated sodium bicarbonate aqueous solution, and lastly brine. The organics were dried over anhydrous sodium sulfate, filtered and concentrated. The residue was purified by column chromatography using hexane/ethyl acetate (3/1) as eluent to give 3-(4-fluorophenyl)-5-(4-{5-[2-(trifluoromethyl)phenyl]-1,3,4-oxadiazol-2-yl}bicyclo[2.2.2]oct-1-yl)-1,2,4-oxadiazole (7-E) as a white solid. $^1$H NMR (500 MHz, CDCl$_3$) δ 2.25 (s, 12H), 7.21 (t, J=8.7 Hz, 2H), 7.74–7.76 (m, 2H), 7.91 (m, 1H), 8.11–8.15 (m, 3H) ppm. ESI-MS m/z (M+H) 485.2.

Step D:

A mixture of above 1,2,4-oxadiazole (7-E) (115.2 mg, 0.238 mmol) and the trifluoroacetic acid salt of methylamine (1.73 g, 11.9 mmol) in a 2M solution of methylamine in methanol (4 mL) was heated at 150° C. in a sealed tube for 48 h. The mixture was then concentrated, and the residue was taken up in dichloromethane, washed with saturated sodium bicarbonate aqueous solution. The organics were concentrated and the residue was purified using reverse-phase HPLC with TFA- buffered acetonitrile/water (40–80%) as eluent. The fractions containing the product were combined, neutralized with saturated sodium bicarbonate aqueous solution and lyophilized from acetonitrile/water to provide 3-(4-fluorophenyl)-5-(4-{4-methyl-5-[2-(trifluoromethyl)phenyl]-4H-1,2,4-triazol-3-yl}bicyclo[2.2.2]oct-1-yl)-1,2,4-oxadiazole (7-F). $^1$HNMR (CDCl$_3$) δ 2.25–2.35 (m, 12H), 3.53 (s, 3H), 7.21 (t, J=8.7 Hz, 2H), 7.54 (m, 1H), 7.73 (m, 2H), 7.88 (m, 1H), 8.13 (m, 2H). ESI-MS m/z (M+H) 498.2.

EXAMPLE 8

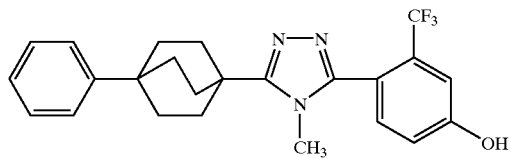

4-[4-Methyl-5-(4-phenylbicyclo[2.2.2]oct-1-yl)-4H-1,2,4-triazol-3-yl]-3-(trifluoromethyl)phenol (8-F)

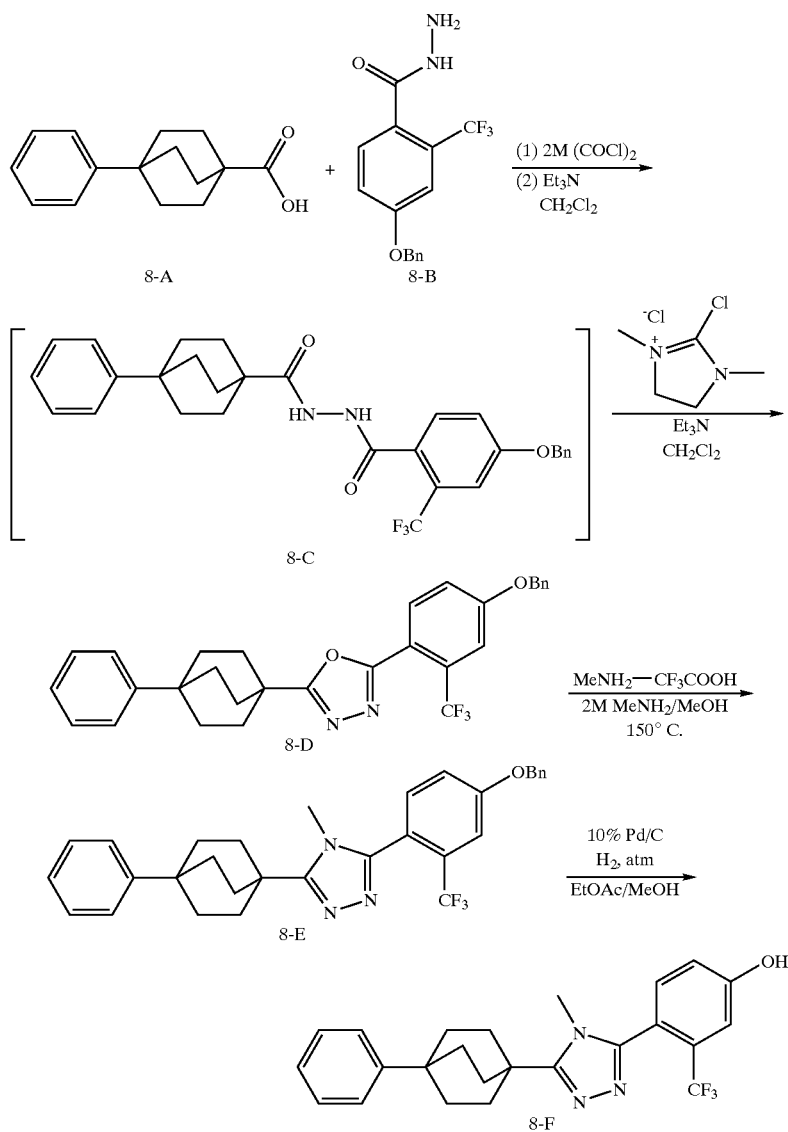

Preparation of 4-phenylbicyclo[2.2.2]octane-1-carboxylic acid (8-A)
Literature reference:
Chapman, N. B, Sotheeswaran, S., and Toyne, K. J, J.Org.Chem, 35: 917–923 (1970)
Step A:
To a magnetically stirred solution of 4-phenylbicyclo[2.2.2]octane-1-carboxylic acid (8-A) (70 mg, 0.30 mmol) in methylene chloride (1 mL) at room temperature was added 2 M oxalyl chloride in methylene chloride (0.61 mL, 1.22 mmol). Two drops of catalytic DMF were added to catalyze the reaction. The reaction was stirred for 30 min and solvent and reagent removed in vacuo. Methylene chloride (I mL) was added to the residue, followed by 4-(benzyloxy)-2-(trifluoromethyl)benzoic hydrazide (8-B) (141 mg, 0.46 mmol) and triethylamine (0.07 mL, 0.46 mmol). The reaction was stirred at room temperature overnight to afford intermediate 8-C,N'-[4-(benzyloxy)-2-(trifluoromethyl)benzoyl]-4-phenylbicyclo[2.2.2]octane-1-carbohydrazide, which was not isolated. To the crude product (8-C) were then added 2-chloro-1,3-dimethylimidazolinium chloride (257 mg, 1.52 mmol), more triethylamine (0.42 mL, 3.04 mmol), and methylene chloride (2 mL). The reaction was stirred at room temperature for 4 h. The reaction mixture was then diluted with methylene chloride (30 mL) and washed with water (30 mL) two times and with brine (30 mL) once. The combined aqueous layers were extracted with methylene chloride (25 mL) once. The combined organic layers were dried (MgSO$_4$) and the solvent removed in vacuo. The residue was chromatographed on silica with 10% ethyl acetate in hexanes as eluant to give 2-[4-(benzyloxy)-2-

(trifluoromethyl)phenyl]-5-(4-phenylbicyclo[2.2.2]oct-1-yl)-1,3,4-oxadiazole (8-D). MS: m/z 505 (M+1).
Step B:

The trifluoroacetate salt of methylamine (380 mg, 2.61 mmol) and 2-[4-(benzyloxy)-2-(trifluoromethyl)phenyl]-5-(4-phenylbicyclo[2.2.2]oct-1-yl)-1,3,4-oxadiazole (8-D) were suspended in a 2 M solution of methylamine in methanol (1.3 mL, 2.61 mmol) and heated at 150° C. overnight. After being cooled to room temperature, the reaction mixture was partitioned between ethyl acetate (25 mL) and saturated aqueous sodium bicarbonate (30 mL). The layers were separated and the aqueous layer extracted with twice with ethyl acetate (25 mL). The combined organic layers were washed with brine, dried (MgSO$_4$), and solvent removed in vacuo. The residue was then dissolved in methanol (8 mL) and purified by reverse phase chromatography using gradient elution with 10% acetonitrile (0.1% TFA) /water (0.1% TFA) to 100% acetonitrile (0.1% TFA) over 10 min (20 mL/min). The fractions containing product were partitioned between saturated aqueous sodium bicarbonate (25 mL) and methylene chloride (15 mL). The layers were separated and the aqueous layer was extracted with methylene chloride (15 mL) three times, dried (MgSO$_4$), and the solvent removed in vacuo to afford 3-[4-(benzyloxy)-2-(trifluoromethyl)phenyl]-4-methyl-5-(4-phenylbicyclo[2.2.2]oct-1-yl)-4H-1,2,4-triazole (8-E). MS: m/z 518 (M+1).
Step C:

The 3-[4-(Benzyloxy)-2-(trifluoromethyl)phenyl]-4-methyl-5-(4-phenylbicyclo[2.2.2]oct-1-yl)-4H-1,2,4-triazole (8-E) (27 mg, 0.05 mmol) was dissolved in ethyl acetate/methanol (1:1, 4 mL) to which 10% palladium-on-carbon (4 mg) was added. The reaction was then placed under hydrogen atmosphere and stirred for 3 h at room temperature and pressure. After appropriate evacuation of the hydrogen atmosphere, the palladium was filtered through a filter aid with methanol (40 mL). The filtrate was collected and the solvent removed in vacuo to afford 4-[4-methyl-5-(4-phenylbicyclo[2.2.2]oct-1-yl)-4H-1,2,4-triazol-3-yl]-3-(trifluoromethyl)phenol (8-F). MS: m/z 428 (M+1); $^1$H NMR (500 MHz, CDCl$_3$): δ 1.92 (6H, m), 2.11 (6H, m), 3.41 (3H, s), 7.17 (2H, m), 7.24 (1H, m), 7.31 (2H, m), 7.38 (3H, m) ppm.

EXAMPLE 9

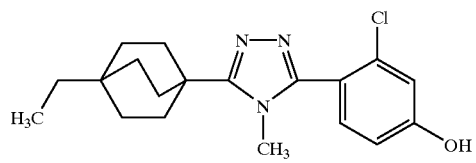

3-Chloro-4-[5-(4-ethylbicyclo[2.2.2]oct-1-yl)-4-methyl-4H-1,2,4-triazol-3-yl]phenol (9-E)

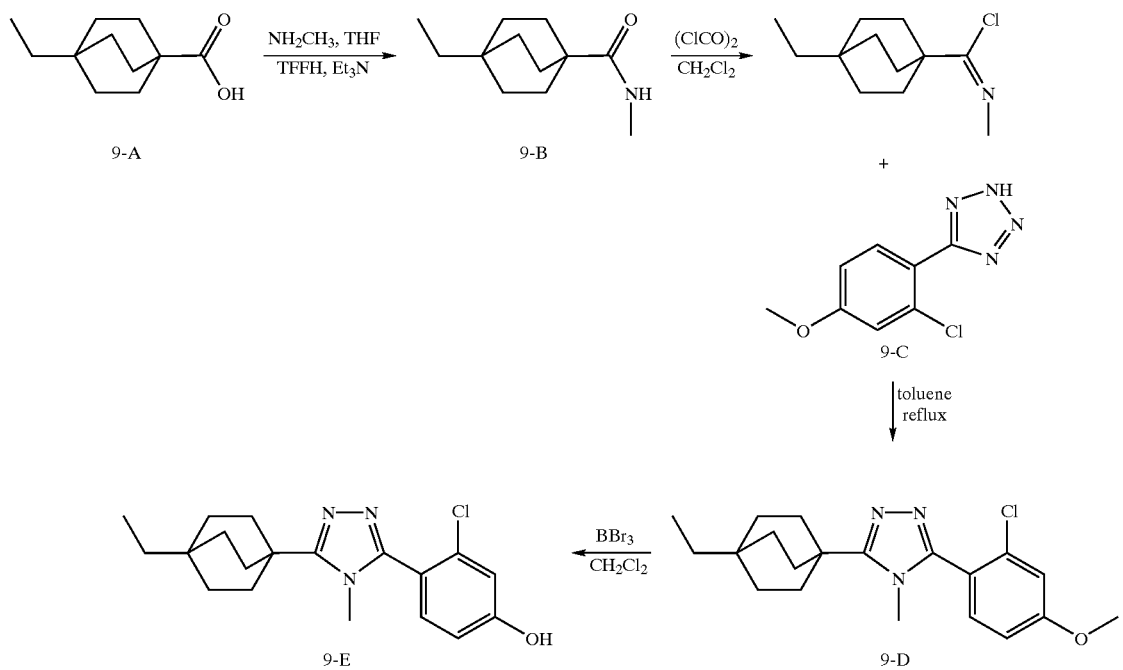

Step A:

To a stirred solution of 4-ethyl-1-carboxylbicyclo[2.2.2]octane (Chapman, N. B. et al. *J. Org. Chem.*, 1970, 35, 917) (45 mg, 0.26 mmol) in 1 mL of degassed DMF were added methylamine (2M in THF, 1 mL, 2 mmol), triethylamine (0.075 mL, 0.53 mmol) and TFFH (70 mg, 0.26 mmol). The solution was stirred at room temperature for 1 h, then diluted with 20 mL of ethyl acetate and washed with 1N aqueous HCl and brine. The organic layer was dried over anhydrous sodium sulfate and evaporated. The brown oily residue was loaded onto a flash silica gel column and eluted with a gradient ranging from 10 to 40% of ethyl acetate in hexanes. 4-Ethyl-N-methylbicyclo[2.2.2]octane-1-carboxamide (9-B) was isolated as a clear, colorless oil.

$^1$H NMR (500 MHz, CDCl$_3$): δ 0.80 (3H, t, J=7.2 Hz), 1.18 (2H, q, J=7.2 Hz), 1.42 (6H, m), 1.76 (6H, m), 2.81 (3H, d, J=6.1 Hz).

Step B:

To a stirred solution of 9-B (45 mg, 0.23 mmol) in 0.25 mL of dry CH$_2$Cl$_2$ was added oxalyl chloride (2M in CH$_2$Cl$_2$, 0.29 mL, 0.58 mmol) and 1 drop of dry DMF. The solution was stirred at room temperature for 2 h, then evaporated. The yellow residue was redissolved in dry toluene and 5-(2-chloro-4-methoxyphenyl)-2H-tetrazole (9-C) was added. The reaction mixture was heated to reflux under inert atmosphere and stirred for additional 1.5 h before being cooled down to room temperature. The solid was filtered, washed with toluene, then redissolved in methylene chloride and washed with saturated aqueous sodium bicarbonate and brine solution. The organic layer was dried, then evaporated. The yellowish residue was purified on a short plug of flash silica gel, eluting with a gradient ranging from 0% to 3% of methanol in methylene chloride. 3-(2-Chloro-4-methoxyphenyl)-5-(4-ethylbicyclo[2.2.2]oct-1-yl)-4-methyl-4H-1,2,4-triazole (9-D) was isolated as a white powder. MS (ESI$^+$)=360.3 (M+1); $^1$H NMR (500 MHz, CDCl$_3$): δ 0.82 (3H, t, J=7.0 Hz), 1.22 (2H, q, J=7.0 Hz), 1.52 (6H, m), 2.10 (6H, m), 3.55 (3H,s), 3.88 (3H, s), 6.92 (1H, dd, J=8.4 Hz, J=2.8 Hz), 7.04 (1H, d, J=2.4 Hz), 7.41 (1H, d, J=8.4 Hz).

Step C:

Triazole 9-D (30 mg, 0.08 mmol) was dissolved in 0.5 mL of dry methylene chloride, placed under an inert atmosphere, and cooled to 0° C. To this solution was added BBr$_3$ (1 M in CH$_2$Cl$_2$, 0.25 mL, 0.25 mmol) and the cooling bath was immediately removed. The reaction was stirred for 2 h then diluted with 20 mL of methylene chloride and washed with 1 N aqueous NaOH and brine. The residue was chromatographed by reverse-phase HPLC, eluting with a gradient of 0 to 100% acetonitrile in water. The product, 3-chloro-4-[5-(4-ethylbicyclo[2.2.2]oct-1-yl)4-methyl-4 H-1,2,4-triazol-3-yl]phenol (9-E), was isolated as a white powder. MS (ESI$^+$)=346.2 (M+1); $^1$H NMR (500 MHz, CDCl$_3$): δ 0.85 (3H, t, J=7.5 Hz), 1.25 (2H, q, J=7.5 Hz), 1.55 (6H, m), 2.13 (6H, m), 3.58 (3H, s), 6.68 (1H, dd, J=8.4 Hz, J=2.6 Hz), 6.91 (1H, d, J=2.6 Hz), 7.10 (1H, d, J=8.4 Hz).

EXAMPLE 10

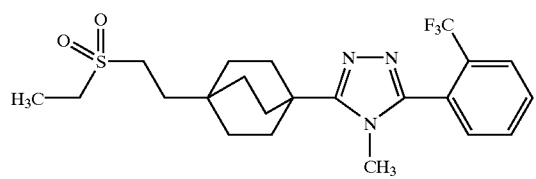

3-{4-[2-(Ethylsulfonyl)ethyl]bicyclo[2.2.2]oct-1-yl}-4-methyl-5-[2-(trifluoromethyl)phenyl]-4H-1,2,4-triazole (10-6)

Scheme 10

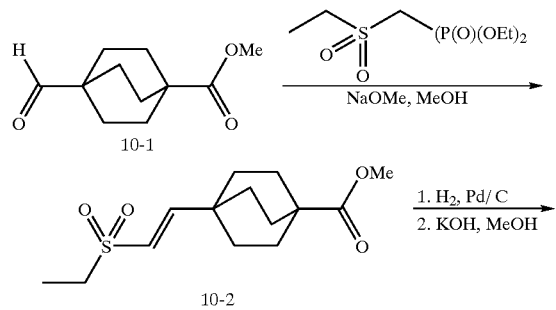

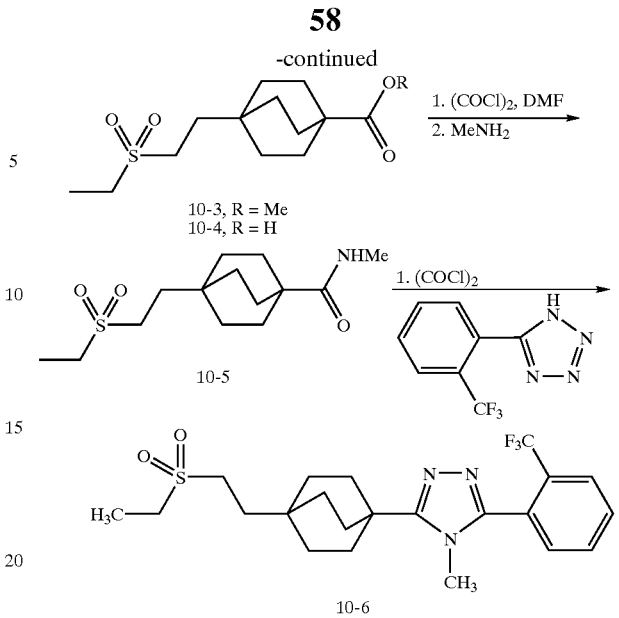

Step A:

Diethyl (ethylsulfonomethane)phosphonate (1.12 g, 4.6 mmol) (Popoff, I. C. et al. *J. Org. Chem.* 34: 1128–30 (1969)) and 4-carbomethoxybicyclo[2.2.2]octane-1-carboxaldehyde (10-1) (0.82 g, 4.2 mmol) (Adock, W., Kok, G. B. *J. Org. Chem.* 50: 1079–1087 (1985)) were dissolved in 8 mL of absolute methanol. The mixture was placed under nitrogen atmosphere, cooled in an ice-bath, and treated with 0.5M solution of sodium methoxide in methanol (8.8 mL, 4.4 mmol). The reaction mixture was kept under reflux for 4 h, then cooled to room temperature, concentrated under diminished pressure, then treated with 2 mL of water and allowed to sit in the refrigerator overnight. The mixture was filtered and the solid washed with a small amount of cold 1:1 MeOH/water. The resulting white solid was collected and dried under vacuum to give the unsaturated sulfone 10-2. MS (ESI$^+$)=287 (M+1).

Step B:

Sulfone 10-2 (880 mg, 3.08 mmol) was dissolved in a 1:2 mixture of ethyl acetate/methanol (30 mL), placed under nitrogen atmosphere, then treated with 10% Pd/C (800 mg). The reaction was placed under hydrogen atmosphere and stirred vigorously for 90 min. The resulting solution was filtered through celite, washed with methanol and ethyl acetate and evaporated to give methyl 4-[2-(ethylsulfonyl) ethyl]bicyclo[2.2.2]octane-1-carboxylate (10-3) as a white solid.

Step C:

Ester 10-3 (880 mg, 3 mmol) was dissolved in 10% water/methanol solution (100 mL) and treated with 1 g of potassium hydroxide. The reaction was heated at 60° C. for 1 h then at 45° C. overnight. The mixture was concentrated in vacuo then acidified to pH 2 with 1M HCl and extracted with three portions of methylene chloride. The organic layers were combined, dried over anhydrous sodium sulfate and evaporated to give 4-[2-(ethylsulfonyl)ethyl]bicyclo [2.2.2]octane-1-carboxylic acid (10-4).

Step D:

Carboxylic acid 10-4 (810 mg, 2.96 mmol) was dissolved in 12 mL of anhydrous methylene chloride under nitrogen atmosphere, treated with oxalyl chloride (2M in methylene chloride, 4.4 mL, 8.8 mmol) and subsequently with 5 drops of DMF. The reaction was stirred at room temperature under nitrogen atmosphere for 90 min, then evaporated and placed under vacuum for 20 min. The acid chloride was dissolved in anhydrous methylene chloride (12 mL), cooled in an ice-bath, and then treated dropwise with a solution of methylamine (2M in THF, 8.9 mL, 17.8 mmol). Upon addition of the amine, the cooling bath was removed and the reaction stirred at ambient temperature for 30 min. The mixture was diluted with 200 mL of methylene chloride and washed with 1N aqueous HCl, saturated aqueous sodium bicarbonate, and brine. The organic layer was dried over anhydrous sodium sulfate and evaporated. The residue was subjected to chromatography on silica gel eluting with a gradient from 0 to 3.5% methanol in methylene chloride to give 4-[2-(ethylsulfonyl)ethyl]-N-methylbicyclo[2.2.2]octane-1-carboxamide 10-5 as a white powder. MS (ESI$^+$)= 288 (M+1).

Step E:

Methyl amide 10-5 (220 mg, 0.77 mmol) was dissolved in anhydrous methylene chloride (2 mL) and treated with oxalyl chloride (2M in methylene chloride, 0.77 mL, 1.54 mmol) and DMF (2 drops). The solution was stirred at room temperature for 1 h, then solvent removed by evaporation under diminished pressure. The residue was redissolved in anhydrous toluene (2 mL) and treated with 5[2-(trifluoromethyl)phenyl]1H-tetrazole (214 mg, 1 mmol). The mixture was refluxed for 18 h. The reaction was cooled to room temperature and the cream-colored precipitate was filtered and washed to give 300 mg of crude product as the HCl salt. The salt was taken up in methylene chloride/1N HCl and the aqueous layer was washed with two additional portions of methylene chloride. The organic layers were combined and evaporated and the residue was chromatographed by flash silica gel chromatography. Elution was carried out with a gradient ranging from 0 to 5% methanol/methylene chloride. The appropriate fractions were combined and evaporated to give 3-{4-[2-(ethylsulfonyl)ethyl]bicyclo[2.2.2]oct-1-yl}-4-methyl-5-[2-(trifluoromethyl)phenyl]-4H 1,2,4-triazole (10-6) as a white powder.

MS (ESI$^+$)=456.2 (M+1); $^1$H NMR (500 MHz, CDCl$_3$): δ 1.46 (3H, t, J=7.3 Hz), 1.63 (6H, m), 1.78 (2H, m), 2.19 (6H, m), 2.96 (2H, m), 3.05 (2H, q, J=7.2 Hz), 3.50 (3H, s), 7.56 (1H, m), 7.72 (2H, m), 7.87 (1H, m) ppm.

EXAMPLE 11

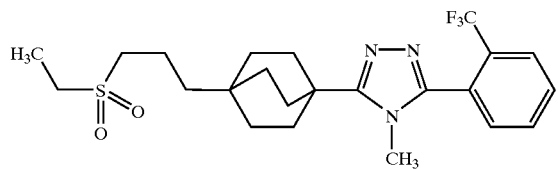

3-{4-[3-(Ethylsulfonyl)propyl]bicyclo[2.2.2]oct-1-yl}-4-methyl-5-[2-(trifluoromethyl)phenyl]-4H -1,2,4-triazole (11-10)

Scheme 11

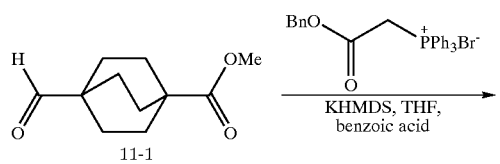

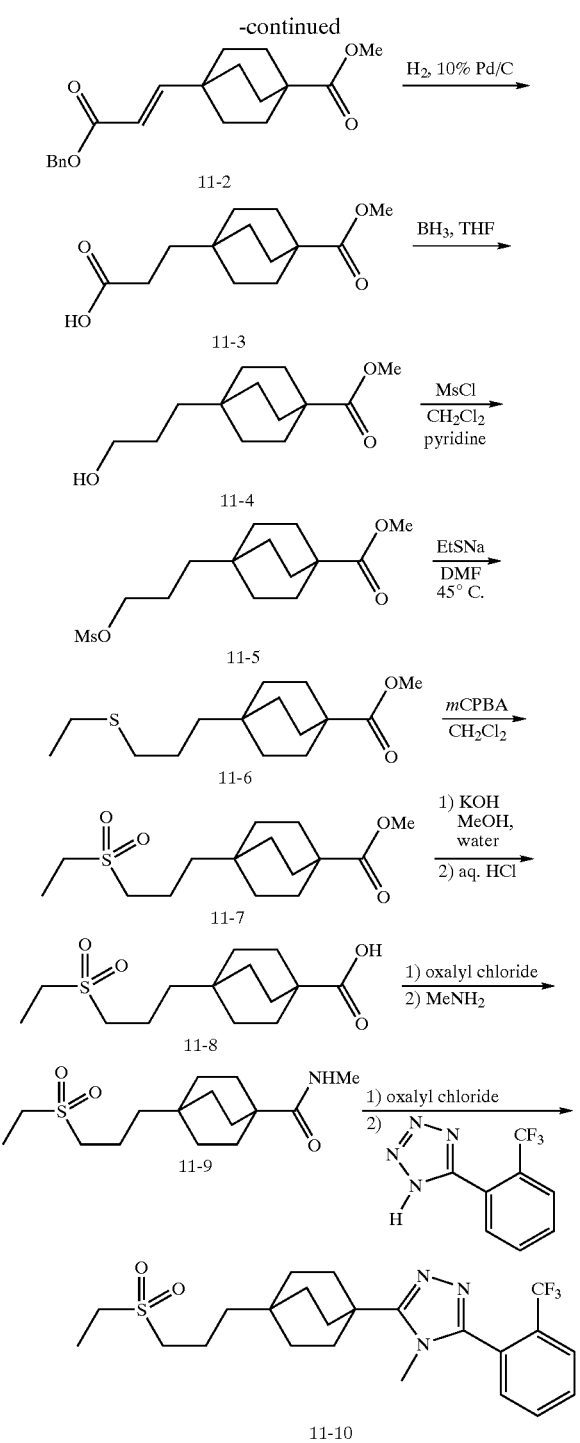

Step A:

(Benzyloxycarbonylmethyl)triphenylphosphonium bromide (4.6 g, 9.4 mmol) was azeotroped twice from toluene, and then suspended in 30 mL dry THF. Potassium hexamethyldisilazide (0.5 M in toluene, 16.8 mL, 8.4 mmol) was added dropwise at room temperature and the yellow solution was allowed to stir for 1 h, after which time it became milky white. A solution of 4carbomethoxybicyclo[2.2.2]octane-1-carboxaldehyde (11-1) (0.50 g, 2.55 mmol) (Adcock, W., Kok, G. B. *J. Orp. Chem.* 50: 1079–1087 (1985)) and benzoic acid (0.015 g, 0.13 mmol) in 2 mL of dry THF was prepared and added dropwise by syringe at room temperature. The mixture was heated to 90° C. and allowed to stir at reflux temperature, after which time the mixture was diluted with 200 mL of ethyl acetate and washed consecutively with 50 mL portions of 1 N HCl (twice), saturated aq. sodium bicarbonate, and brine. The organic layer was dried using magnesium sulfate, and the solvent was removed under reduced pressure. The residue was chromatographed on silica, eluting with a gradient of 5% to 10% ethyl acetate in hexane to provide methyl 4-[(1E)-3-(benzyloxy)-3-oxoprop-1-en-1-yl]bicyclo[2.2.2]octane-1-carboxylate (11-2) as a colorless oil. $^1$H NMR (500 MHz, CDCl$_3$): δ 7.4 (5H, m), 6.94 (1H, d, J=17 Hz), 5.77 (1H, d, J=17 Hz), 5.21 (2H, s), 3.69 (3H, s), 1.86 (6H, m), 1.63 (6H, m) ppm.

Step B:

Diester 11-2 (0.625 g, 1.90 mmol) was dissolved in a 1:1 mixture of ethyl acetate/methanol (30 mL), placed under nitrogen atmosphere, then treated with 10% Pd/C (500 mg) and 0.1 mL of acetic acid. The reaction was placed under hydrogen atmosphere and stirred vigorously for 2 hr. The resulting solution was filtered through celite and the solvent was removed under reduced pressure. The residue was partitioned between 200 mL of ethyl acetate and 200 mL of 1 N NaOH solution. The aqueous layer was separated and neutralized, then extracted three times with 50 mL of methylene chloride. The combined organic layers were dried over magnesium sulfate and the solvent was removed under reduced pressure to afford 3-[4-(methoxycarbonyl)bicyclo[2.2.2]oct-1-yl]propanoic acid (11-3). $^1$H NMR (500 MHz, CDCl$_3$): δ 3.62 (3H, s), 2.20 (2H, broad t, J=9 Hz), 1.75 (6H, m), 1.47 (2H, broad t, J=9 Hz), 1.38 (6H, m) ppm.

Step C:

Carboxylic acid 11-3 (400 mg, 1.67 mmol) was dissolved in tetrahydrofuran (5 mL) and borane (1 M solution in THF, 2.17 mL, 1.3 eq.) was added dropwise at room temperature. After 2 h the reaction was added to 50 mL of 1 N HCl and then extracted three times with 50 mL of methylene chloride. The combined organic layers were dried over magnesium sulfate and the solvent was removed under reduced pressure to afford crude methyl 4-(3-hydroxypropyl)bicyclo[2.2.2]octane-1-carboxylate (11-4) which was used without purification in the next step. $^1$H NMR (500 MHz, CD$_3$OD): δ 3.66 (3H, s), 3.62 (2H, t, J=6.5 Hz), 1.78 (6H, m), 1.50 (2H, m), 1.41 (2H, m), 1.17 (2H, m) ppm.

Step D:

Hydroxyester 11-4 (430 mg, 1.9 mmol) was dissolved in 2.5 mL of anhydrous methylene chloride under nitrogen atmosphere, treated with pyridine (0.5 mL) and methanesulfonyl chloride (0.368 mL, 4.8 mmol) and stirred for 4 h at room temperature. The mixture was diluted with 100 mL of ethyl acetate and washed with 1N aqueous HCl, saturated aqueous sodium bicarbonate, and brine. The organic layer was dried over anhydrous sodium sulfate and evaporated. The crude methyl 4-{3-[(methylsulfonyl)oxy]propyl}bicyclo-[2.2.2]octane-1-carboxylate (11-5) thus afforded was used without purification in the next reaction. $^1$H NMR (500 MHz, CDCl$_3$): δ 4.22 (2H, t, J=7.5 Hz), 3.68 (3H, s), 3.04 (3H, s), 1.82 (6H, m), 1.70 (2H, m), 1.44 (6H, m), 1.24 (2H, m) ppm.

Step E:

Mesylate 11-5 (3.30 g, 10.9 mmol) was dissolved in DMF (20 mL) and treated with sodium ethanethiolate (1.82 g, 21.7 mmol). The solution was stirred at 45° C. for 3 h, then the mixture was diluted with 100 mL of ethyl acetate and washed twice with 1N aqueous HCl, then with saturated aqueous sodium bicarbonate, and brine. The organic layer was dried over anhydrous sodium sulfate and evaporated to afford methyl 4-[3-(ethylthio)propyl]bicyclo[2.2.2]octane-1-carboxylate (11-6) as a crude oil which was used without purification in the next step.

$^1$H NMR (500 MHz, CDCl$_3$): δ 3.68 ppm (3H, s), 2.56 (2H, q, J=7 Hz), 2.51 (2H, t, J=7.5 Hz), 1.80 (6H, m), 1.52 (2H,m), 1.42 (6H, m), 1.28 (2H, t, J=7 Hz), 1.02 (2H, m).

Step F:

Sulfide 11-6 (3.0 g, 11 mmol) was dissolved in methylene chloride (50 mL) and treated with m-chloroperbenzoic acid (75%, 6.2 g). The solution was stirred at room temperature for 2 h, then the mixture was diluted with 100 mL of methylene chloride and washed with saturated aqueous sodium bicarbonate, then twice with saaturated aqueous sodium bisulfite, then twice with saturated aqueous sodium bicarbonate, and brine. The organic layer was dried over anhydrous sodium sulfate and evaporated to afford methyl 4-[3-(ethylsulfonyl)propyl]bicyclo[2.2.2]octane-1-carboxylate (11-7) as a crude oil which was used without purification in the next step. $^1$H NMR (500 MHz, CDCl$_3$): δ 3.68 ppm (3H, s), 2.56 (2H, q, J=7 Hz), 2.51 (2H, t, J=7.5 Hz), 1.80 (6H, m), 1.52 (2H, m), 1.42 (6H, m), 1.28 (2H, t, J=7 Hz), 1.02 (2H, m) ppm.

Step G:

Sulfone 11-7 (3.1 g, 10 mmol) was dissolved in 9:1 MeOH/water (50 mL) and treated with potassium hydroxide (3 g). The solution was stirred at room temperature overnight, then the mixture was acidified with 1 N HCl and extracted four times with 50 mL of methylene chloride. The organic layer was dried over anhydrous sodium sulfate and evaporated to afford 4-[3-(ethylsulfonyl)propyl]bicyclo[2.2.2]octane-1-carboxylic acid (11-8) which was used without purification in the next step. $^1$H NMR (500 MHz, CDCl$_3$): δ 3.03 (2H, q, J=7 Hz), 2.94 (2H, dd, J=7.5 Hz), 1.84 (8H, m), 1.45 (8H, m), 1.30 (2H, m) ppm.

Step H:

Carboxylic acid 11-8 (3.0 g, 11 mmol) was dissolved in 50 mL of anhydrous methylene chloride under nitrogen atmosphere, treated with oxalyl chloride (2 M in methylene chloride, 16.2 mL, 32.4 mmol) and subsequently with 5 drops of DMF. The reaction was stirred at room temperature under nitrogen atmosphere for 90 min, then evaporated and placed under vacuum for 20 min. The acid chloride was dissolved in anhydrous methylene chloride (12 mL), cooled in an ice-bath, and then treated dropwise with a solution of methylamine (2M in THF, 27 mL, 54 mmol). Upon addition of the methylamine, the cooling bath was removed and the reaction stirred at ambient temperature for 30 min. The mixture was diluted with 200 mL of methylene chloride and washed with 1N aqueous HCl, saturated aqueous sodium bicarbonate, and brine. The organic layer was dried over anhydrous sodium sulfate and evaporated. The residue was subjected to chromatography on silica gel eluting with a gradient from 0 to 3% methanol in ethyl acetate to give 4-[3-(ethylsulfonyl)propyl]-N-methylbicyclo[2.2.2]octane-1-carboxamide 11-9 as a white powder. MS (ESI$^+$)=302 (M+1).

1H NMR (500 MHz, CDCl$_3$): δ 5.56 (1H, br s), 3.02 (2H, q, J=7 Hz), 2.94 (2H, dd, J=7.5 Hz), 2.82 (3H, d, J=4 Hz), 1.80 (8H, m), 1.45 (9H, m), 1,28 (2H, m) ppm.

Step I:

Methyl amide 11-9 (0.470 g, 1.56 mmol) was dissolved in anhydrous methylene chloride (5 mL) and treated with oxalyl chloride (2M in methylene chloride, 1.56 mL, 3.12 mmol) and DMF (2 drops). The solution was stirred at room temperature for 1 h, then solvent removed by evaporation under reduced pressure. The residue was redissolved in anhydrous toluene (7 mL) and treated with 5[2-(trifluoromethyl)phenyl]1H-tetrazole (368 mg, 1.72 mmol).

The mixture was refluxed for 18 h. The reaction was cooled to room temperature and the precipitate was filtered and washed to give 300 mg of crude product as the HCl salt. The salt was taken up in methylene chloride/1N HCl and the aqueous layer was washed with two additional portions of methylene chloride. The organic layers were combined and evaporated and the residue was chromatographed by flash silica gel chromatography. Elution was carried out with a gradient ranging from 0 to 5% methanol/methylene chloride. The appropriate fractions were combined and evaporated to give 3-{4-[3-(ethylsulfonyl)propyl]bicyclo[2.2.2]oct-1-yl}-4methyl-5-[2-(trifluoromethyl)phenyl]-4H -1,2,4-triazole (11-10) as a white powder.

MS (ESI$^+$)=470.4 (M+1). $^1$H NMR (500 MHz, CDCl$_3$): δ 7.87 (1H, m), 7.72 (2H, m), 7.56 (1H, m), 3.49 (3H, s), 3.05 (2H, q, J=7.2 Hz), 2.96 (2H, m), 2.18 (6H, m), 1.86 (2H, m), 1.62 (6H, m), 1.46 (3H, t, J=7.3 Hz), 1.36 (2H, m) ppm.

EXAMPLE 12

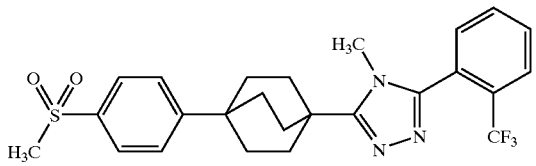

4-Methyl-3-{4-[4-(methylsulfonyl)phenyl]bicyclo[2.2.2.]oct-1-yl}-5-[2-(trifluoromethyl)phenyl]-4H-1,2,-triazole (12-G)

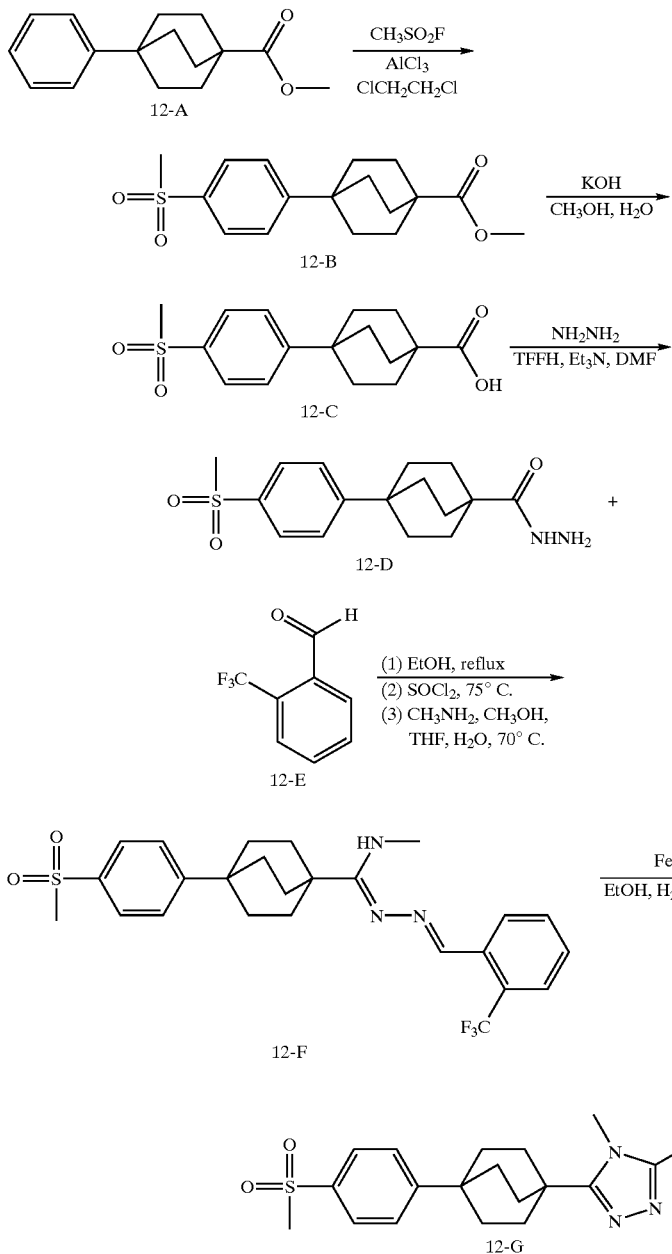

Step A:

To a stirred solution of methyl 4-phenylbicyclo[2.2.2]octane-1-carboxylate 12-A (Chapman, N. B. et al. J. Org. Chem., 1970, 35, 917) (4.80 g, 19.6 mmol) in 1,2-dichloroethane (2 ml, 1M) was added methanesulfonyl fluoride (4.05 ml, 58.9 mmol) followed by aluminum trichloride (9.17 g, 68.8 mmol). The reaction mixture was stirred overnight under nitrogen atmosphere at ambient temperature followed by addition of another portion of methanesulfonyl fluoride (4.05 ml, 58.9 mmol) and aluminum trichloride (9.17 g, 68.8 mmol). The resulting mixture was heated at 80° C. for 3 h, then cooled to room temperature and diluted with 300 ml of dichloromethane and 200 ml water. The layers were separated and the aqueous layer was washed with two 100 ml portions of dichloromethane. The organic layers were combined, washed with brine, dried (MgSO$_4$), and concentrated in vacuo. The crude product was chromatographed on normal phase flash silica gel column, eluting with a gradient 10–50% EtOAc/hexanes to yield 1.4 g of 12-B (>95% pure). The material was recrystallized from EtOAc to yield compound 12-B.

$^1$H NMR (500 MHz, CDCl$_3$): δ 1.93 (6H, m), 1.99 (6H, m), 3.08 (3H, s), 3.73 (3H, s), 7.55 (2H, d, J=8.3 Hz), 7.90 (2H, d, J=8.1 Hz) ppm.

Step B:

Carboxylic acid 12-C was prepared in quantitative yield by hydrolysis of ester 12-B (1.1 g, 3.4 mmol) using the procedures described in Example 11, Step G. $^1$H NMR (500 MHz, CDCl$_3$): δ 1.98 (6H, m), 2.04 (6H, m), 3.11 (3H, s), 7.58 (2H, d, J=7.8 Hz), 7.92 (2H, d, J=7.9 Hz) ppm.

Step C:

Carboxylic acid 12-C (0.99 g, 3.2 mmol) was converted to hydrazide 12-D using hydrazine (0.124 ml, 4 mmol) and the standard coupling procedure analogous to Example 9, step A. Crude product was purified by flash silica gel chromatography eluting with 0–2% MeOH/CH$_2$Cl$_2$ gradient to yield a white powder. MS (ESI$^+$)=323.2 (M+1).

Step D:

To a suspension of 12-D (0.67 g, 2.1 mmol) in EtOH (11 ml) was added aldehyde 12-E (0.36 g, 2.1 mmol) and the mixture was refluxed for 18 h. The solvent was removed in vacuo and the solid residue was heated in thionyl chloride (2.9 ml, 40 mmol) for 2 h at 75° C. then stripped to dryness. This residue was treated with methylamine (2M THF, 2 ml) and methylamine (40% aqueous, 1 ml) for 18 h at 70° C. The volatiles were removed in vacuo and the solid was chromatographed on a flash silica gel column using a 10–25% acetone/hexanes gradient to yield compound 12-F. MS (ESI$^+$)=492.3 (M+1);

$^1$H NMR (500 MHz, CDCl$_3$) (2 isomers ratio 3:2): major isomer: δ 2.00 (6H, m), 2.14 (6H, m), 3.10 (3H, s), 3.28 (3H, d, J=5.1 Hz), 5.71 (1H, br. s), 7.47 (1H, m), 7.59 (3H, m), 7.72 (1H, d, J=7.9 Hz), 7.92 (2H, m), 8.26 (1H, d, J=7.9 Hz), 8.70 (1H, br. s) ppm; minor isomer: δ 2.00 (6H, m), 2.32 (6H, m), 2.98 (3H, d, J=4.7 Hz), 3.10 (3H, s), 4.70 (1H, br. s), 7.47 (1H,m), 7.59 (4H, m), 7.92 (2H, m), 8.30 (1H, d, J=7.8 Hz), 8.56 (1H, br. s) ppm.

Step E:

A solution of 12-F (0.58 g, 1.2 mmol) in EtOH (5 ml) was heated to 40° C. then treated with a solution of ferric chloride (0.4 g, 2.4 mmol) in water (1 ml). The resulting mixture was heated at 90° C. for 18 h. Another portion of ferric chloride (0.4 g, 2.4 mmol) was added and the reaction heated at 90° C. for 24 h. The volatiles were removed in vacuo and the solid was redissolved in CH$_2$Cl$_2$ and washed with a saturated aqueous solution of EDTA and brine then dried (MgSO$_4$) and stripped. The crude product was purified and isolated using the conditions described for purification of 4-J (Example 4, step G) to yield compound 12-G.

MS (ES$^+$)=490.3 (M+1); $^1$H NMR (500 MHz, CDCl$_3$): δ 2.06 (6H, m), 2.31 (6H, m), 3.08 (3H, s), 3.52 (3H, s), 7.52 (1H, m), 7.59 (2H, d, J=8.4 Hz), 7.71 (2H, m), 7.86 (1H, m), 7.92 (2H, d, J=8.6 Hz) ppm.

EXAMPLE 13

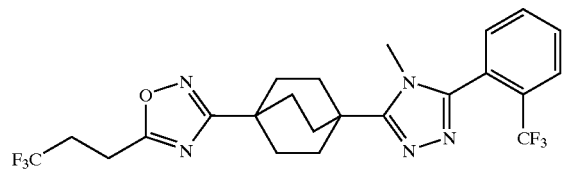

3-(4-{4-Methyl-5-[2-(trifluoromethyl)phenyl]-4H-1,2,4-triazol-3-yl}bicyclo[2.2.2]oct-1-yl)-5-(3,3,3-trifluoropropyl)-1,2,4-oxadiazole (13-F)

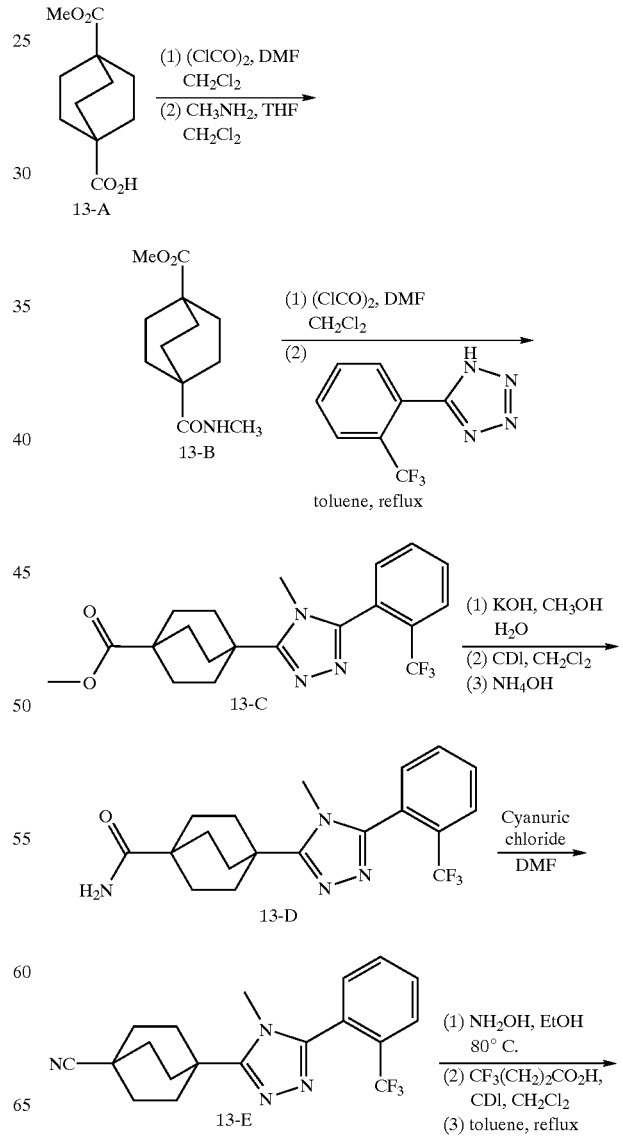

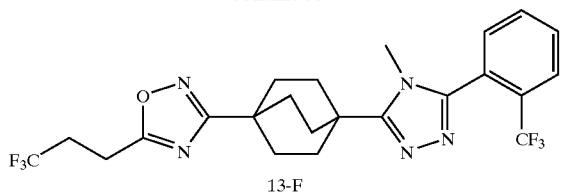

13-F

Step A:
4-(Methoxycarbonyl)bicyclo[2.2.2]octane-1-carboxylic acid 13-A (Chapman, N. B. et al. J. Org. Chem., 1970, 35, 917) (4.0 g, 18.9 mmol) was converted to methyl 4-[(methylamino)carbonyl]bicyclo[2.2.2]octane-1-carboxylate 13-B using the methods described in Example 10, steps C and D. Product was purified by flash silica gel chromatography, eluting with 0–5% MeOH/CH$_2$Cl$_2$ gradient to yield a white solid. MS (ESI$^+$)=226.2 (M+1).

Step B:
Methyl 4-[(methylamino)carbonyl]bicyclo[2.2.2]octane-1-carboxylate 13-B (2.76 g, 12.3 mmol) was converted to 1,2,4-triazole 13-C using the procedures described in Example 10, Step E. The product, which precipitated out of reaction mixture as the HCl salt, was dissolved in CH$_2$Cl$_2$, washed twice with saturated aqueous sodium bicarbonate solution, dried (MgSO$_4$) and stripped to yield a white solid. MS (ESI$^+$)=394.2 (M+1);
$^1$H NMR (500 MHz, CDCl$_3$): δ 2.00 (6H, m), 2.18 (6H, m), 3.48 (3H, s), 3.72 (3H, s), 7.51 (1H, m), 7.71 (2H, m), 7.85 (1H, m) ppm.

Step C:
A solution of methyl ester 13-C (1.19 g, 3.0 mmol) in 5% H$_2$O/MeOH (30 ml) was treated with KOH (0.51 g, 9.0 mmol) at 60° C. under nitrogen atmosphere for 18 h. The resulting mixture was concentrated down, diluted with water (150 ml), washed with EtOAc and acidified with aqueous HCl (1 N) to pH=3. The precipitate was filtered, washed with a small amount of water and ether and dried under vacuum to yield a pink solid (0.87 g, 76%). A portion of the solid (0.67 g, 1.77 mmol) was suspended in CH$_2$Cl$_2$ (15 ml) and treated with carbonyldiimidazole (0.57 g, 3.54 mmol) at room temperature and nitrogen atmosphere. After 2 h, concentrated ammonium hydroxide was added (40 ml) and the reaction was stirred for 18 h. The crude mixture was diluted with water (150 ml) and extracted with 3 portions of CH$_2$Cl$_2$ (70 ml). The organic washes were combined, washed with brine, dried (Na$_2$SO$_4$), and stripped to yield compound 13-D as a white powder. MS (ESI$^+$)=379.3 (M+1).

Step D:
A solution of carboxamide 13-D (0.64 g, 1.7 mmol) and cyanuric chloride (0.47 g, 2.53 mmol) in DMF (15 ml) was stirred at room temperature under nitrogen atmosphere. After 2 h, DMF was removed in vacuo and the solid was redissolved in CH$_2$Cl$_2$ (100 ml) and washed with saturated aqueous sodium bicarbonate and brine, dried (Na$_2$SO$_4$), and stripped to give the nitrile 13-E as a pale yellow solid. MS (ESI$^+$)=361.3 (M+1); $^1$H NMR (500 MHz, CDCl$_3$): δ 2.15 (6H, m), 2.22 (6H, m), 3.47 (3H, s), 7.51 (1H, m), 7.72 (2H, m), 7.87 (1H, m) ppm.

Step E:
A solution of nitrile 13-E (0.56 g, 1.6 mmol) and hydroxylamine (50% aqueous, 4 ml) in ethanol (40 ml) was heated at 80° C. for 18 h. The resulting mixture was cooled to room temperature and concentrated in vacuo. The solid was suspended in toluene, the solvent removed in vacuo, and the solid was dried under reduced pressure. A portion of the resulting white powder (0.050 g, 0.13 mmol) was added to a pre-stirred solution of 4,4,4-trifluorobutyric acid (0.072 g, 0.51 mmol) and carbonyldiimidazole (0.082 g, 0.51 mmol) in CH$_2$Cl$_2$ (3 ml). The resulting mixture was stirred at room temperature for 48 h, then concentrated down. The solid was resuspended in toluene and refluxed under nitrogen atmosphere for 3 h. The crude product was purified and isolated using the conditions described for purification of 4-J (Example 4, step G) to yield 13-F as a white powder.
MS (ESI$^+$)=500.2 (M+1); $^1$H NMR (500 MHz, CDCl$_3$): δ 2.12 (6H, m), 2.30 (6H, m), 2.73 (2H, m), 3.18 (2H, m), 3.54 (3H, s), 7.61 (1H, m), 7.74 (2H, m), 7.87 (1H, m) ppm.

EXAMPLE 14

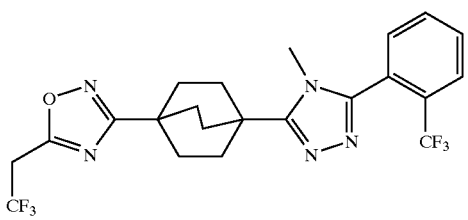

3-(4-{4-Methyl-5-[2-(trifluoromethyl)phenyl]-4H-1,2,4-triazol-3-yl}bicyclo[2.2.2]oct-1-yl)-5-(3,3,3-trifluoroethyl)-1,2,4-oxadiazole (14-B)

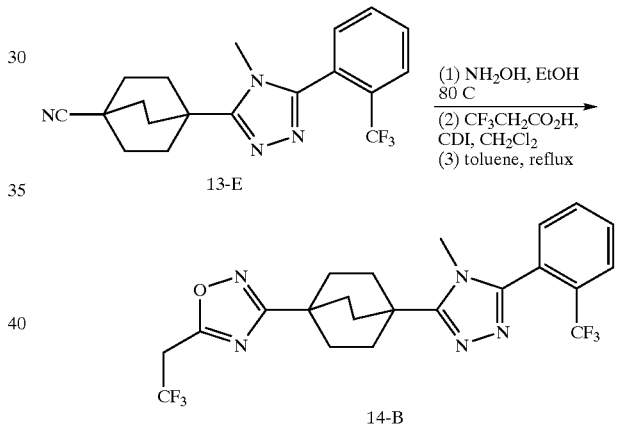

Step A:
Triazole 14-B was prepared from nitrile 13-E (0.053 g, 0.14 mmol) and 3,3,3-trifluoromethylpropionic acid (0.036 ml, 0.41 mmol) using the method described in Example 13, step E. 3-(4-{4-Methyl-5-[2-(trifluoromethyl)phenyl]-4H-1,2,4-triazol-3-yl}bicyclo[2.2.2]oct-1- yl)-5-(3,3,3-trifluoroethyl)-1,2,4-oxadiazole (14-B) was isolated as a white powder. MS (ESI$^+$)=486.2 (M+1); $^1$H NMR (500 MHz, CDCl$_3$): δ 2.14 (6H, m), 2.31 (6H, m), 3.53 (3H, s), 3.81 (2H, q, J=9.5 Hz), 7.57 (1H, m), 7.73 (2H, m), 7.87 (1H, m) ppm.

EXAMPLE 15

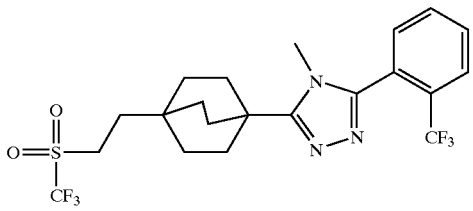

4-Methyl-3-[2-(trifluoromethyl)phenyl]-5-(4-{2-[(trifluoromethyl)sulfonyl]ethyl}bicyclo[2.2.2]oct-1-yl)-4H-1,2,4-triazole (15-G)

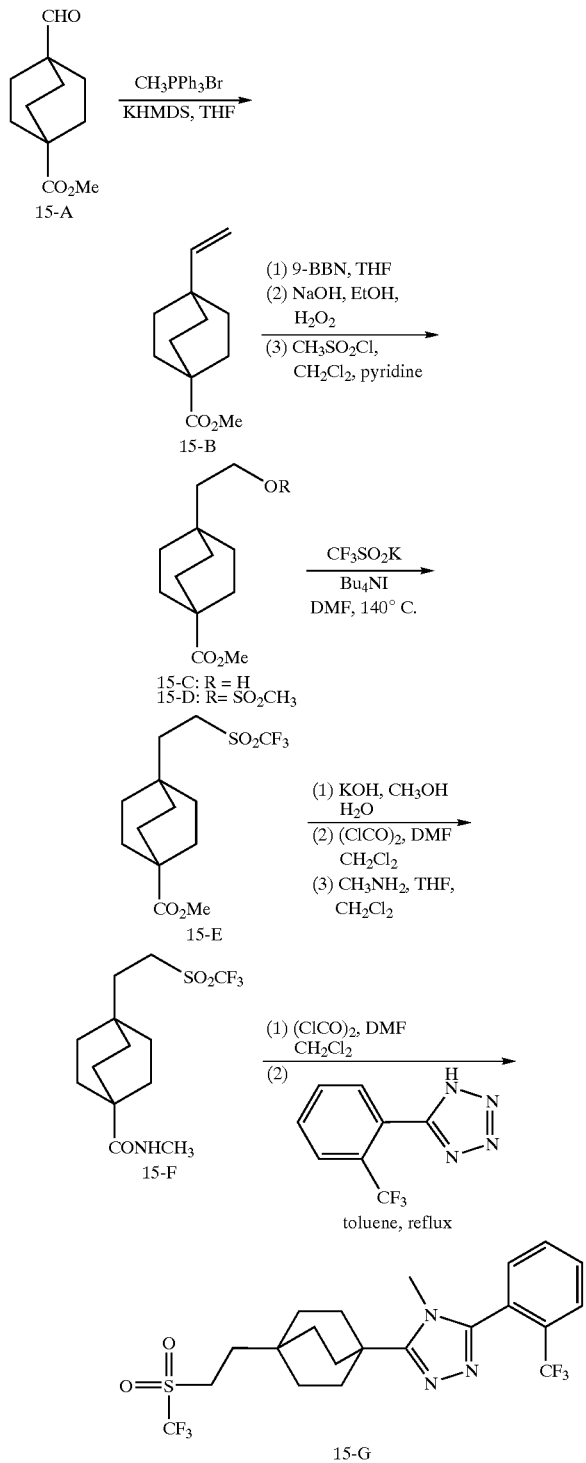

Step A:

To a stirred solution of methyltriphenylphosphonium bromide (9.1 g, 12.8 mmol) in THF (50 ml) at 0° C. was added potassium hexamethyldisilazide (0.5M in toluene, 48.6 ml), dropwise over 5 min. The resulting mixture was allowed to warm up to room temperature over 1 h, then cooled again to 0° C. and treated with methyl 4-formylbicyclo[2.2.2]octane-1-carboxylate 15-A (Chapman, N. B. et al. J. Org. Chem., 1970, 35, 917) (2.5 g, 12.8 mmol). The reaction mixture was stirred at room temperature for 18 h then diluted with EtOAc (350 ml). The organic phase was washed with aqueous HCl (1 N), saturated aqueous sodium bicarbonate, and brine, then dried ($Na_2SO_4$) and concentrated in vacuo. The resulting solid was purified by flash silica gel chromatography, eluting with a gradient 0–4% EtOAc/hexanes. The resulting methyl 4-vinylbicyclo[2.2.2]octane-1-carboxylate 15-B was isolated as a clear, colorless oil.

Step B:

To a stirred solution of olefin 15-B (1.6 g, 8.3 mmol) in THF (20 ml) was added 9-BBN (0.5M in THF, 49 ml), dropwise. The solution was allowed to stir at room temperature for 18 h, then treated sequentially with ethanol (14.5 ml), aqueous NaOH (5N, 5 ml), and hydrogen peroxide (30% aqueous, 9.7 ml). The reaction mixture was acidified to pH=2 with aqueous HCl (1 N) and extracted three times with $CH_2Cl_2$. The organic layers were combined, washed with brine, dried ($Na_2SO_4$), and stripped. The resulting alcohol 15-C was purified by silica gel chromatography eluting with a gradient 30–50% EtOAc/hexanes and isolated as a clear, colorless oil.

Step C:

A solution of alcohol 15-C (1.5 g, 7.1 mmol) in $CH_2Cl_2$ (7.5 ml), pyridine (1.5 ml) was cooled to 0° C. and treated with methanesulfonyl chloride (1.65 ml, 21.3 mmol), dropwise over 5 min. The reaction mixture was allowed to warm to room temperature, then stirred for 3 h. EtOAc (300 ml) was added and the organic phase was washed with aqueous HCl (1 N) three times, saturated aqueous sodium bicarbonate two times, and brine. The organic layer was dried ($Na_2SO_4$), and stripped to yield methyl 4-{2-[(methylsulfonyl)oxy]ethyl}bicyclo[2.2.2]octane-1-carboxylate 15-D as a white solid. $^1$H NMR (500 MHz, $CDCl_3$): δ 1.52 (6H, m), 1.66 (2H, t, J=7.1 Hz), 1.84 (6H, m), 3.04 (3H, s), 3.69 (3H, s), 4.29 (2H, t, J=7.2 Hz) ppm.

Step D:

A solution of 15-D (0.25 g, 0.86 mmol), potassium trifluoromethanesulfinate (0.3 g, 1.72 mmol), and tetrabutylammonium iodide (0.15 g, 0.4 mmol) in DMF (5 ml) was heated at 140° C. for 5 h. under nitrogen atmosphere. The solution was then cooled to room temperature and diluted with EtOAc (100 ml) and washed with aqueous HCl (1N) two times and brine. The organic layer was dried ($Na_2SO_4$), stripped, and chromatographed on flash silica gel, eluting with a gradient 5–20% EtOAct hexanes. The resulting trifluoromethylsulfone 15-E was isolated as a white solid. $^1$H NMR (500 MHz, $CDCl_3$): δ 1.50 (6H, m), 1.78 (2H, m), 1.82 (6H, m), 3.17 (2H, m), 3.67 (3H, s) ppm.

Step E:

Methyl ester 15-E (0.035 g, 0.11 mmol) was converted to the methyl amide 15-F using the methods described in Example 10, steps C and D. The N-methyl-4-{2-[(trifluoromethyl)sulfonyl]ethyl}bicyclo[2.2.2]octane-1-carboxamide was isolated as a white solid; MS (ESI$^+$)=328.2 (M+1).

Step F:

Methyl amide 15-F (0.030 g, 0.092 mmol) was converted to triazole 15-G using the procedures outlined in Example 10, step E. 4-Methyl-3-[2-(trifluoromethyl)phenyl]-5-(4-{2-[(trifluoromethyl)sulfonyl]ethyl}bicyclo[2.2.2]oct-1-yl)-4H-1,2,4-triazole (15-G) was isolated as a white powder; MS (ESI$^+$)=496.4 (M+1).

EXAMPLES 16–150

Following procedures similar to those described above, the following compounds of formula II were also prepared:

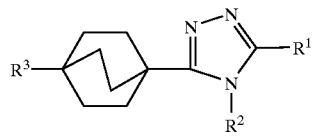
(II)
| Ex. # | R³ | R² | R¹ | Parent Ion m/z |
|---|---|---|---|---|
| 16 | H₃C~~~~~ | CH₃ | phenyl | 338 |
| 17 | H₃C~~~~~ | CH₃ | 2-(CF₃)phenyl | 406 |
| 18 | H₃C~~~~~ | CH₃ | 2-CH₃-phenyl | 352 |
| 19 | H₃C~~~~~ | CH₃ | 2-Cl-phenyl | 372 |
| 20 | H₃C~~~~~ | CH₃ | 2-F-phenyl | 356 |
| 21 | H₃C~~~~~ | CH₃ | 2-MeO-phenyl | 368 |
| 22 | H₃C~~~~~ | CH₃ | 2-MeS-phenyl | 384 |
| 23 | H₃C~~~~~ | CH₃ | 2-O₂N-phenyl | 383 |
| 24 | H₃C~~~~~ | CH₃ | 2-MeO₂S-phenyl | 416 |

-continued
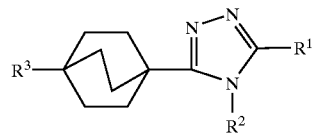
(II)
| Ex. # | R³ | R² | R¹ | Parent Ion m/z |
|---|---|---|---|---|
| 25 | H₃C~~~~~ | CH₃ | ⟨o-OCF₃-C₆H₄⟩ | 422 |
| 26 | H₃C~~~~~ | CH₃ | ⟨o-OH-C₆H₄⟩ | 354 |
| 27 | H₃C~~~~~ | CH₃ | ⟨o-OEt-C₆H₄⟩ | 382 |
| 28 | H₃C~~~~~ | CH₃ | ⟨p-OCF₃-C₆H₄⟩ | 422 |
| 29 | H₃C~~~~~ | CH₃ | ⟨p-OMe-C₆H₄⟩ | 368 |
| 30 | H₃C~~~~~ | CH₃ | ⟨p-OH-C₆H₄⟩ | 354 |
| 31 | H₃C~~~~~ | CH₃ | ⟨3,5-Br₂-C₆H₃⟩ | 496 |
| 32 | H₃C~~~~~ | CH₃ | ⟨3-Br-C₆H₄⟩ | 417 |
| 33 | H₃C~~~~~ | CH₃ | ⟨3-Cl-C₆H₄⟩ | 372 |
| 34 | H₃C~~~~~ | CH₃ | ⟨4-Cl-C₆H₄⟩ | 372 |

-continued
(II)
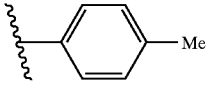
| Ex. # | R³ | R² | R¹ | Parent Ion m/z |
|---|---|---|---|---|
| 35 | H₃C~~~~~ | CH₃ | ~~~-C₆H₄-Me (4-) | 352 |
| 36 | H₃C~~~~~ | CH₃ | 2,3-(MeO)₂-C₆H₃- | 398 |
| 37 | H₃C~~~~~ | CH₃ | 2-MeO-4-Me-C₆H₃- | 382 |
| 38 | H₃C~~~~~ | CH₃ | 2-MeOS-C₆H₄- | 400 |
| 39 | H₃C~~~~~ | CH₃ | 3-OMe-C₆H₄- | 368 |
| 40 | H₃C~~~~~ | CH₃ | 4-F-C₆H₄- | 356 |
| 41 | H₃C~~~~~ | CH₃ | 2-Me-CH₂-C₆H₄- | 366 |
| 42 | H₃C~~~~~ | CH₃ | 2,4-(MeO)₂-C₆H₃- | 398 |
| 43 | H₃C~~~~~ | CH₃ | 2,4-F₂-C₆H₃- | 374 |
| 44 | H₃C~~~~~ | CH₃ | 2-HF₂CO-C₆H₄- | 404 |

-continued
(II)
| Ex. # | R³ | R² | R¹ | Parent Ion m/z |
|---|---|---|---|---|
| 45 | 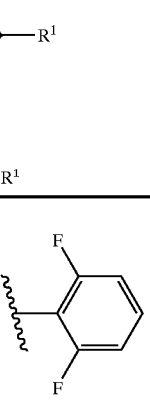 | CH₃ | 2,6-difluorophenyl | 374 |
| 46 | 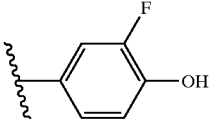 | CH₃ | 3-fluoro-4-hydroxyphenyl | 372 |
| 47 | 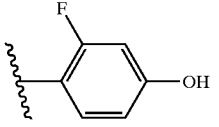 | CH₃ | 2-fluoro-4-hydroxyphenyl | 372 |
| 48 | 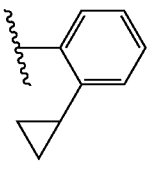 | CH₃ | 2-cyclopropylphenyl | 378 |
| 49 | 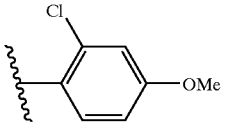 | CH₃ | 2-chloro-4-methoxyphenyl | 402 |
| 50 | 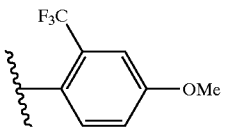 | CH₃ | 2-trifluoromethyl-4-methoxyphenyl | 436 |
| 51 | 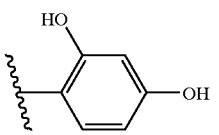 | CH₃ | 2,4-dihydroxyphenyl | 370 |
| 52 | 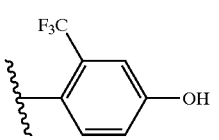 | CH₃ | 2-trifluoromethyl-4-hydroxyphenyl | 422 |
| 53 | 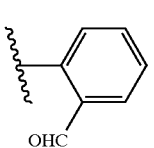 | CH₃ | 2-formylphenyl | 366 |

-continued (II)

| Ex. # | R³ | R² | R¹ | Parent Ion m/z |
|---|---|---|---|---|
| 54 | H₃C-(hexyl) | CH₃ | 2-(MeO₂S—NH)-phenyl | 431 |
| 55 | H₃C-(hexyl) | CH₃ | 2-Me-4-OMe-phenyl | 382 |
| 56 | H₃C-(hexyl) | CH₃ | 4-OPh-phenyl | 430 |
| 57 | H₃C-(hexyl) | CH₃ | 2-Ph-phenyl | 414 |
| 58 | H₃C-(hexyl) | CH₃ | 2-Br-phenyl | 418 |
| 59 | H₃C-(hexyl) | CH₃ | 2-MeO-4-OCH₂Ph-phenyl | 474 |
| 60 | H₃C-(hexyl) | CH₃ | 2-PhO-phenyl | 430 |
| 61 | H₃C-(hexyl) | CH₃ | 2-H₂N-phenyl | 353 |
| 62 | H₃C-(hexyl) | CH₃ | 2-NC-phenyl | 363 |

-continued
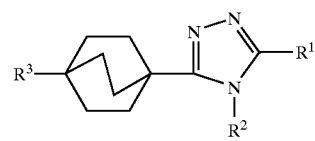
(II)
| Ex. # | R³ | R² | R¹ | Parent Ion m/z |
|---|---|---|---|---|
| 63 | H₃C~~~~~ | CH₃ | ~~C(O)-C₆H₅ | 366 |
| 64 | H₃C~~~~~ | CH₃ | 2-pyridyl | 339 |
| 65 | H₃C~~~~~ | CH₃ | 3-pyridyl | 339 |
| 66 | H₃C~~~~~ | CH₃ | 4-pyridyl | 339 |
| 67 | H₃C~~~~~ | CH₃ | 2-pyridyl N-oxide | 355 |
| 68 | H₃C~~~~~ | CH₃ | 2-pyrimidyl | 340 |
| 69 | H₃C~~~~~ | CH₃ | 1-naphthyl | 388 |
| 70 | H₃C~~~~~ | CH₃ | 2-naphthyl | 388 |
| 71 | H₃C~~~~~ | CH₃ | 4-benzofuranyl | 378 |
| 72 | H₃C~~~~~ | CH₃ | 4-indolyl | 377 |

-continued
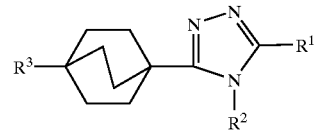
(II)
| Ex. # | R³ | R² | R¹ | Parent Ion m/z |
|---|---|---|---|---|
| 73 | H₃C~~~~~ | CH₃ | quinolin-8-yl | 389 |
| 74 | H₃C~~~~~ | CH₃ | 1H-indol-7-yl | 377 |
| 75 | H₃C~~~~~ | CH₃ | 2,3-dihydrobenzofuran-4-yl | 380 |
| 76 | H₃C~~~~~ | CH₃ | 2,3-dihydrobenzofuran-7-yl | 380 |
| 77 | H₃C~~~~~ | CH₃ | benzo[1,3]dioxol-4-yl | 382 |
| 78 | H₃C~~~~~ | CH₃ | 3-chlorothiophen-2-yl | 378 |
| 79 | H₃C~~~~~ | CH₂CH₃ | 2-methoxyphenyl | 382 |
| 80 | H₃C~~~~~ | CH₂CH₃ | 4-methoxyphenyl | 382 |
| 81 | H₃C~~~~~ | CH₂CH₃ | phenyl | 352 |

-continued (II)

R³—[bicyclo]—[triazole]—R¹, N-R²

| Ex. # | R³ | R² | R¹ | Parent Ion m/z |
|---|---|---|---|---|
| 82 | H₃C~~~~~ (hexyl) | CH₂CH₃ | 4-hydroxyphenyl | 368 |
| 83 | H₃C~~~~~ (hexyl) | CH₂CH₃ | 2-CHO-phenyl | 380 |
| 84 | H₃C~~~~~ (hexyl) | CH₂CH₃ | 2-Me-phenyl | 366 |
| 85 | H₃C~~~~~ (hexyl) | CH₂CH=CH₂ | phenyl | 364 |
| 86 | isohexyl | CH₃ | 2-Cl-phenyl | 373 |
| 87 | isohexyl | CH₃ | 3-Cl-4-OH-phenyl | 389 |
| 88 | H₃C~~~~~ (hexyl) | cyclopropyl | phenyl | 365 |
| 89 | H₃C~~~ (butyl) | CH₃ | 2-MeO-phenyl | 340 |
| 90 | H₃C~~~ (butyl) | CH₃ | 2-CF₃-phenyl | 378 |
| 91 | H₃C~~~ (butyl) | CH₃ | 2-Cl-phenyl | 345 |

-continued (II)

| Ex. # | R³ | R² | R¹ | Parent Ion m/z |
|---|---|---|---|---|
| 92 | H₃C-CH₂-CH- | CH₃ | -C₆H₄-OMe (4-) | 340 |
| 93 | H₃C-CH₂-CH- | CH₃ | -C₆H₄-OH (4-) | 326 |
| 94 | H₃C-CH₂-CH- | CH₃ | 2-Me, 4-OMe phenyl | 354 |
| 95 | H₃C-CH₂-CH- | CH₃ | 2-Cl, 4-OH phenyl | 361 |
| 96 | H₃C-CH₂-CH- | CH₃ | 2-MeO, 4-OH phenyl | 356 |
| 97 | H₃C-CH₂-CH- | CH₃ | 2-Me, 4-OH phenyl | 340 |
| 98 | cyclopropyl | CH₃ | 2-Cl phenyl | 343 |
| 99 | cyclopropyl | CH₃ | 2-MeO phenyl | 338 |
| 100 | H₃C-CH- (isopropyl) | CH₃ | 2-CF₃ phenyl | 364 |
| 101 | H₃C-CH- (isopropyl) | CH₃ | 2-MeO phenyl | 326 |

-continued (II)

| Ex. # | R³ | R² | R¹ | Parent Ion m/z |
|---|---|---|---|---|
| 102 | H₃C-CH₂- | CH₃ | 4-HO-C₆H₄- | 312 |
| 103 | H₃C-CH₂- | CH₃ | 2-Cl-C₆H₄- | 331 |
| 104 | H₃C-CH₂- | CH₃ | 2-MeO-4-HO-C₆H₃- | 342 |
| 105 | H₃C-CH₂- | CH₃ | 2-Me-4-HO-C₆H₃- | 326 |
| 106 | H₃C-CH₂- | CH₃ | 2-Me-4-OMe-C₆H₃- | 340 |
| 107 | H₃C-CH₂- | CH₃ | 2-Cl-4-OMe-C₆H₃- | 361 |
| 108 | HO-CH₂CH₂- | CH₃ | 2-Me-4-OMe-C₆H₃- | 356 |
| 109 | F-CH₂CH₂- | CH₃ | 2-Cl-4-OH-C₆H₃- | 365 |
| 110 | F-CH₂CH₂- | CH₃ | 2-CF₃-C₆H₄- | 382 |
| 111 | F-CH₂CH₂- | CH₃ | 2-Me-4-OMe-C₆H₃- | 358 |

-continued
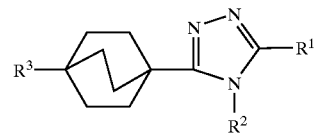
(II)
| Ex. # | R³ | R² | R¹ | Parent Ion m/z |
|---|---|---|---|---|
| 112 | FCH₂CH₂CH₂– | CH₃ | 2-Cl, 4-OMe phenyl | 379 |
| 113 | H₃C-CH₂-S-CH₂CH₂– | CH₃ | 2-Cl, 4-OH phenyl | 407 |
| 114 | H₃C-CH₂-S(O)₂-CH₂CH₂– | CH₃ | 2-Cl, 4-OH phenyl | 438 |
| 115 | CH₃ | CH₃ | phenyl | 282 |
| 116 | CHF₂– | CH₃ | 2-OMe phenyl | 348 |
| 117 | H | CH₃ | 4-OH phenyl | 284 |
| 118 | H | CH₃ | 2-OMe phenyl | 298 |
| 119 | H | CH₃ | 2-Cl phenyl | 302 |
| 120 | H | CH₃ | 4-OMe phenyl | 298 |
| 121 | H | CH₃ | 2-CF₃ phenyl | 336 |

-continued (II)

| Ex. # | R³ | R² | R¹ | Parent Ion m/z |
|---|---|---|---|---|
| 122 | phenyl | CH₃ | phenyl | 344 |
| 123 | phenyl | CH₃ | 2-MeO-phenyl | 374 |
| 124 | phenyl | CH₃ | 2-Me-phenyl | 358 |
| 125 | phenyl | CH₃ | 4-OH-phenyl | 360 |
| 126 | 5-Br-pyrimidin-2-yl-NH— | CH₃ | 2-MeO-phenyl | 471 |
| 127 | 5-Br-pyrimidin-2-yl-NH— | CH₃ | 4-OH-phenyl | 456 |
| 128 | MeO₂C-CH— | CH₃ | phenyl | 326 |
| 129 | CbzNH— | CH₃ | 2-MeO-phenyl | 428 |
| 130 | NH₂ | CH₃ | 2-MeO-phenyl | 313 |
| 131 | 4-F₃C-thiazol-2-yl | CH₃ | 2-MeO-phenyl | 450 |

-continued (II)

| Ex. # | R³ | R² | R¹ | Parent Ion m/z |
|---|---|---|---|---|
| 132 | cyclopropylmethyl-1,2,4-oxadiazol-5-yl | CH₃ | 2-MeO-phenyl | 421 |
| 133 | H₃C-CH₂-S(O)₂-CH₂- | CH₃ | 2-Cl-phenyl | 422 |
| 134 | H₃C-CH₂-S(O)₂-CH₂- | CH₃ | 2-Me-phenyl | 402 |
| 135 | Me-S(O)₂-(CH₂)₃- | CH₃ | 2-F₃C-phenyl | 456 |
| 136 | iPr-S(O)₂-CH₂- | CH₃ | 2-F₃C-phenyl | 470 |
| 137 | Me-CH₂-S(O)₂-CH₂- | CH₃ | 2-F₃C-phenyl | 442 |
| 138 | Me-CH₂-S(O)-CH₂- | CH₃ | 2-F₃C-phenyl | 440 |
| 139 | Me-CH₂-CH₂-S(O)₂-CH₂- | CH₃ | 2-F₃C-phenyl | 470 |
| 140 | tBu-S(O)₂-CH₂- | CH₃ | 2-F₃C-phenyl | 484 |

-continued (II) Structure: R³—[bicyclooctane]—[1,2,4-triazole with R¹ at 3-position and R² on N4]

| Ex. # | R³ | R² | R¹ | Parent Ion m/z |
|---|---|---|---|---|
| 141 | phenyl-SO₂-CH₂-CH₂-~ | CH₃ | 2-(CF₃)-phenyl | 490 |
| 142 | 4-F-phenyl-SO₂-CH₂-CH₂-~ | CH₃ | 2-(CF₃)-phenyl | 508 |
| 143 | H₃C-C(=O)-(CH₂)₃-~ | CH₃ | 2-(CF₃)-phenyl | 420 |

Furthermore following procedure similar to those described above, the following compounds of formula III were also prepared:

(III) Structure: R⁵-phenyl—[1,2,4-oxadiazole]—[bicyclooctane]—[1,2,4-triazole with R¹ and N-CH₃]

| Ex. # | R⁵ | R¹ | Parent Ion m/z |
|---|---|---|---|
| 144 | Cl | 2-MeO-phenyl | 477 |
| 145 | Cl | 2-(CF₃)-phenyl | 515 |
| 146 | Cl | 2-Cl-phenyl | 480 |
| 147 | Cl | 2-Cl-4-OMe-phenyl | 511 |
| 148 | Cl | 2-Cl-4-OH-phenyl | 497 |
| 149 | F | 3-MeO-4-OH-phenyl | 476 |

-continued

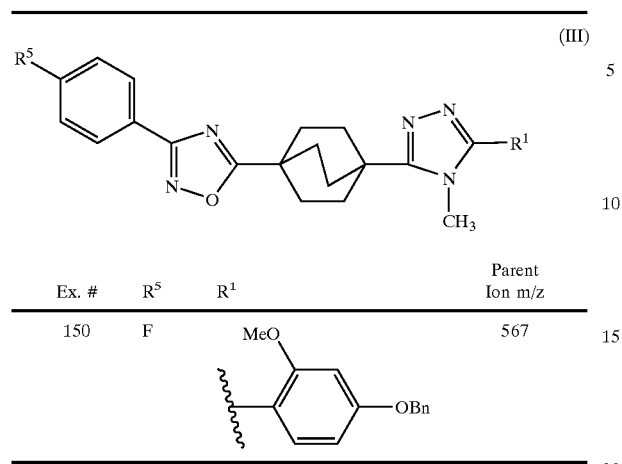

(III)

| Ex. # | R⁵ | R¹ | Parent Ion m/z |
|---|---|---|---|
| 150 | F | 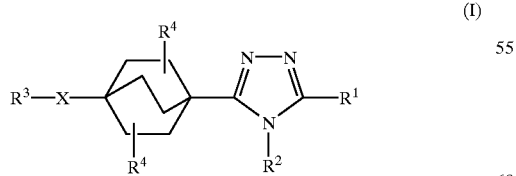 | 567 |

EXAMPLE OF A PHARMACEUTICAL FORMULATION

As a specific embodiment of an oral composition of a compound of the present invention, 50 mg of any of Examples 1–15 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I:

(I)

R³—X—[bicyclic with R⁴, R⁴]—[triazole with R¹, R²]

or a pharmaceutically acceptable salt thereof; wherein
each p is independently 0, 1, or 2;
each n is independently 0, 1, or 2;
X is selected from the group consisting of a single bond, O, $S(O)_p$, $NR^6$,

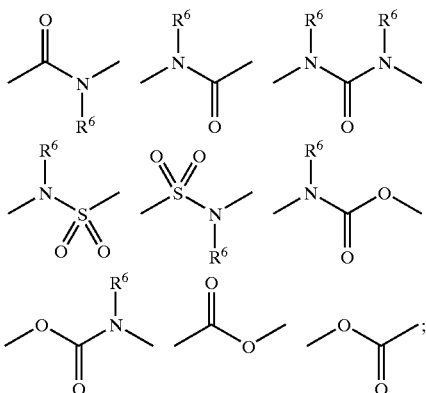

$R^1$ is selected from the group consisting of
 arylcarbonyl,
 $(CH_2)_n$-aryl, and
 $(CH_2)_n$-heteroaryl;
in which aryl and heteroaryl are unsubstituted or substituted with one to three substituents independently selected from $R^5$;
$R^2$ is selected from the group consisting of
 hydrogen,
 $C_{1-8}$ alkyl,
 $C_{2-6}$ alkenyl, and
 $(CH_2)_n$—$C_{3-6}$ cycloalkyl;
in which alkyl, alkenyl, and cycloalkyl are unsubstituted or substituted with one to three substituents independently selected from $R^8$ and oxo;
each $R^4$ is independently selected from the group consisting of
 hydrogen,
 halogen,
 hydroxy,
 oxo,
 $C_{1-3}$ alkyl, and
 $C_{1-3}$ alkoxy;
$R^3$ is selected from the group consisting of
 hydrogen,
 $C_{1-10}$ alkyl,
 $C_{2-10}$ alkenyl,
 $(CH_2)_n$—$C_{3-6}$ cycloalkyl,
 $(CH_2)_n$-aryl, and
 $(CH_2)_n$-heteroaryl;
 $(CH_2)_n$-heterocyclyl;
in which aryl, heteroaryl and heterocyclyl are unsubstituted or substituted with one to three substituents independently selected from $R^5$; and alkyl, alkenyl, and cycloalkyl are unsubstituted or substituted with one to five groups independently selected from $R^8$ and oxo;
$R^5$ and $R^8$ are independently selected from the group consisting of
 hydrogen,
 formyl,
 $C_{1-6}$ alkyl,
 $(CH_2)_n$-aryl,
 $(CH_2)_n$-heteroaryl,
 $(CH_2)_n$-heterocyclyl,
 $(CH_2)_nC_{3-7}$ cycloalkyl,
 halogen,
 $OR^7$,
 $(CH_2)_nN(R^7)_2$,
 cyano, $(CH_2)_nCO_2R^7$,
$NO_2$,
$(CH_2)_nNR^7SO_2R^6$,
$(CH_2)_nSO_2N(R^7)_2$,
$(CH_2)_nS(O)_pR^6$,
$(CH_2)_nSO_2OR^7$,
$(CH_2)_nNR^7C(O)N(R^7)_2$,
$(CH_2)_nC(O)N(R^7)_2$,
$(CH_2)_nNR^6C(O)R^6$,
$(CH_2)_nNR^6CO_2R^7$,
$O(CH_2)_nC(O)N(R^7)_2$,
$CF_3$,
$CH_2CF_3$,
$OCF_3$,
$OCHCF_2$, and
$OCH_2CF_3$;

wherein aryl, heteroaryl, cycloalkyl, and heterocyclyl are unsubstituted or substituted with one to three substituents independently selected from halogen, hydroxy, $C_{1-4}$ alkyl, trifluoromethyl, trifluoromethoxy, and $C_{1-4}$ alkoxy; and wherein any methylene ($CH_2$) carbon atom in $R^5$ and $R^8$ is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;

each $R^6$ is independently selected from the group consisting of
$C_{1-8}$ alkyl,
$(CH_2)_n$-aryl,
$(CH_2)_n$-heteroaryl, and
$(CH_2)_nC_{3-7}$ cycloalkyl;

wherein alkyl and cycloalkyl are unsubstituted or substituted with one to five substituents independently selected from halogen, oxo, $C_{1-4}$ alkoxy, $C_{1-4}$ alkylthio, hydroxy, amino; and aryl and heteroaryl are unsubstituted or substituted with one to three substituents independently selected from cyano, halogen, hydroxy, amino, carboxy, trifluoromethyl, trifluoromethoxy, $C_{1-4}$ alkyl, and $C_{1-4}$ alkoxy; or two $R^6$ groups together with the atom to which they are attached form a 5- to 8-membered mono- or bicyclic ring system optionally containing an additional heteroatom selected from O, S, and $NC_{1-4}$ alkyl; and each $R^7$ is hydrogen or $R^6$.

2. The compound of claim 1 wherein $R^2$ is cyclopropyl, $C_{1-3}$ alkyl, or $C_{2-3}$ alkenyl and $R^1$ is phenyl or naphthyl in which phenyl and naphthyl are unsubstituted or substituted with one to three substituents independently selected from $R^5$.

3. The compound of claim 2 wherein $R^5$ is selected from the group consisting of halogen, hydroxy, trifluoromethyl, trifluoromethoxy, $C_{1-3}$ alkyl, $C_{1-3}$ alkoxy, $C_{1-3}$ alkylthio, and $C_{1-3}$ alkylsulfonyl.

4. The compound of claim 3 wherein $R^2$ is methyl and $R^4$ is hydrogen.

5. The compound of claim 1 wherein

X is a single bond;

$R^1$ is phenyl or naphthyl in which phenyl and naphthyl are unsubstituted or substituted with one to three substituents independently selected from $R^5$;

$R^2$ is cyclopropyl, $C_{1-3}$ alkyl, or $C_{2-3}$ alkenyl; and $R^3$ is $C_{1-6}$ alkyl unsubstituted or substituted with one to three substituents independently selected from $R^8$ and oxo.

6. The compound of claim 5 wherein $R^5$ is selected from the group consisting of halogen, hydroxy, trifluoromethyl, trifluoromethoxy, $C_{1-3}$ alkyl, $C_{1-3}$ alkoxy, $C_{1-3}$ alkylthio, and $C_{1-3}$ alkylsulfonyl.

7. The compound of claim 6 wherein $R^2$ is methyl and $R^4$ is hydrogen.

8. The compound of claim 5 wherein $R^8$ is selected from the group consisting of halogen, hydroxy, oxo, $C_{1-4}$ alkoxy, $C_{1-4}$ alkylthio, $C_{1-4}$ alkylsulfinyl, $C_{1-4}$ alkylsulfonyl, and phenyl unsubstituted or substituted with one to three groups independently selected from halogen and trifluoromethyl.

9. The compound of claim 8 wherein $R^2$ is methyl and $R^4$ is hydrogen.

10. The compound of claim 5 wherein $R^5$ is selected from the group consisting of halogen, hydroxy, trifluoromethyl, trifluoromethoxy, $C_{1-3}$ alkyl, $C_{1-3}$ alkoxy, $C_{1-3}$ alkylthio, and $C_{1-3}$ alkylsulfonyl; and $R^8$ is selected from the group consisting of halogen, hydroxy, oxo, $C_{1-4}$ alkoxy, $C_{1-4}$ alkylthio, $C_{1-4}$ alkylsulfonyl, and phenyl unsubstituted or substituted with one to three groups independently selected from halogen and trifluoromethyl.

11. The compound of claim 10 wherein $R^2$ is methyl and $R^4$ is hydrogen.

12. The compound of claim 1 wherein

X is a single bond;

$R^1$ is phenyl or naphthyl in which phenyl and naphthyl are unsubstituted or substituted with one to three substituents independently selected from $R^5$;

$R^2$ is cyclopropyl, $C_{1-3}$ alkyl, or $C_{2-3}$ alkenyl; and $R^3$ is phenyl or heteroaryl wherein phenyl and heteroaryl are unsubstituted or substituted with one with one to three substituents independently selected from $R^5$.

13. The compound of claim 12 wherein $R^2$ is methyl and $R^4$ is hydrogen.

14. The compound of claim 12 wherein $R^3$ is phenyl unsubstituted or substituted with one with one to three substituents independently selected from $R^5$.

15. The compound of claim 14 wherein $R^5$ is selected from the group consisting of halogen, hydroxy, trifluoromethyl, trifluoromethoxy, $C_{1-3}$ alkyl, $C_{1-3}$ alkoxy, $C_{1-3}$ alkylthio, and $C_{1-3}$ alkylsulfonyl.

16. The compound of claim 15 wherein $R^2$ is methyl and $R^4$ is hydrogen.

17. The compound of claim 12 wherein $R^3$ is oxadiazolyl, unsubstituted or substituted with one with one to two substituents independently selected from $R^5$.

18. The compound of claim 17 wherein $R^5$ is phenyl unsubstituted or substituted with one to three substituents independently selected from halogen, hydroxy, $C_{1-4}$ alkyl, trifluoromethyl, trifluoromethoxy, and $C_{1-4}$ alkoxy.

19. The compound of claim 18 wherein $R^2$ is methyl and $R^4$ is hydrogen.

20. A compound of structural formula II selected from the group consisting of:

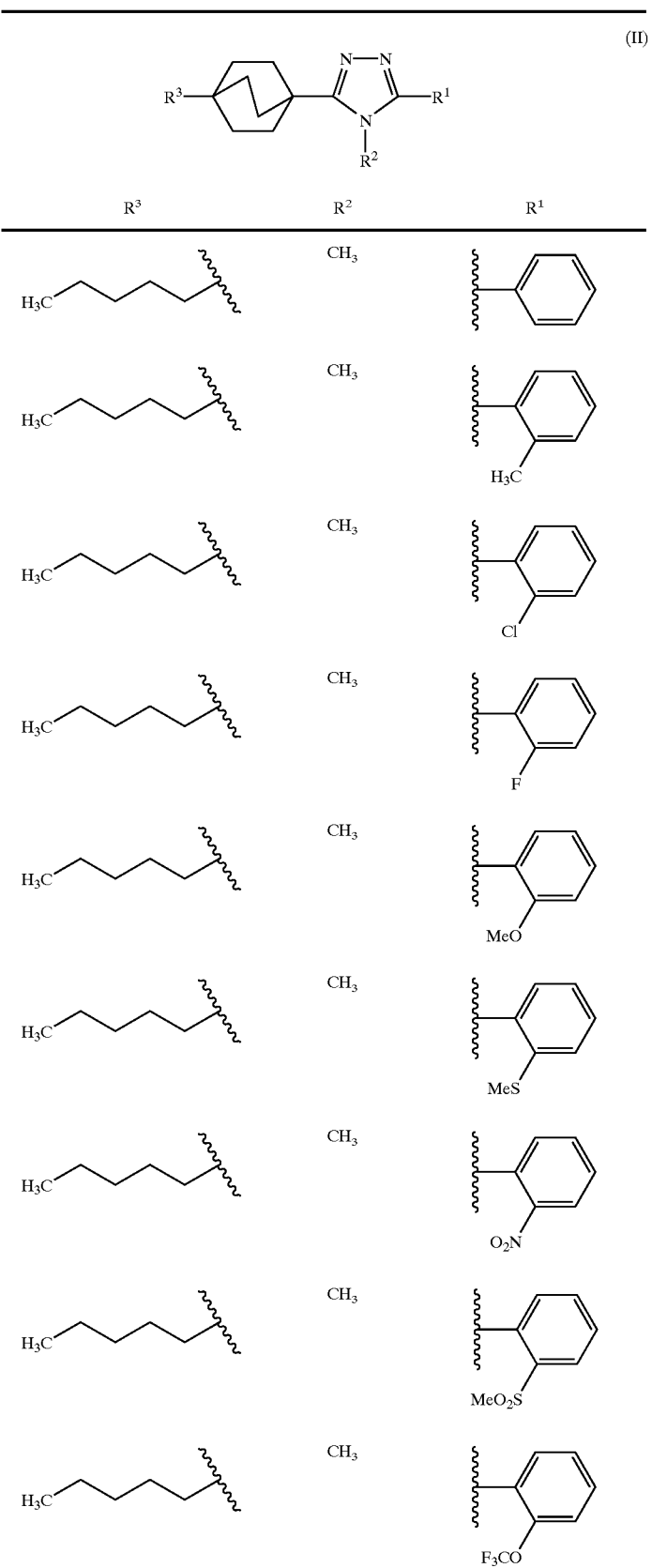

-continued
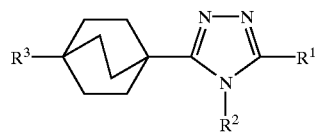
(II)
| R³ | R² | R¹ |
|---|---|---|
| 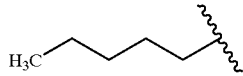 | CH₃ | 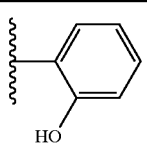 (2-OH phenyl) |
| 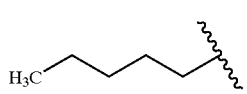 | CH₃ | 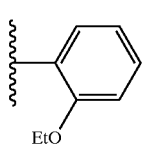 (2-OEt phenyl) |
| 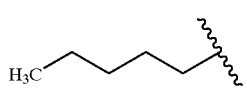 | CH₃ | 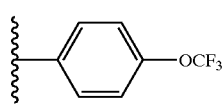 (4-OCF₃ phenyl) |
| 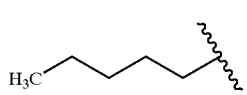 | CH₃ | 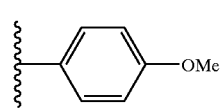 (4-OMe phenyl) |
| 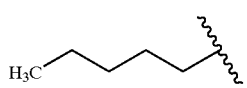 | CH₃ | 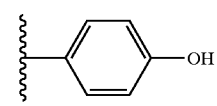 (4-OH phenyl) |
| 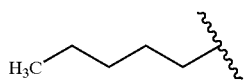 | CH₃ | 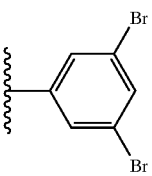 (3,5-diBr phenyl) |
| 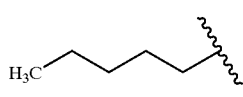 | CH₃ | 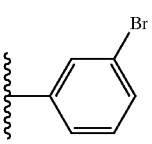 (3-Br phenyl) |
| 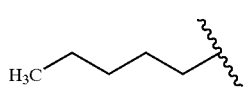 | CH₃ | 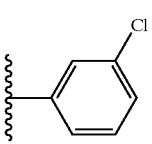 (3-Cl phenyl) |
| 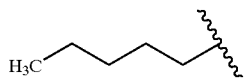 | CH₃ | 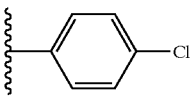 (4-Cl phenyl) |
| 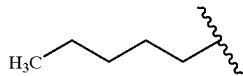 | CH₃ | 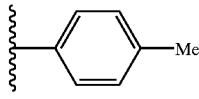 (4-Me phenyl) |

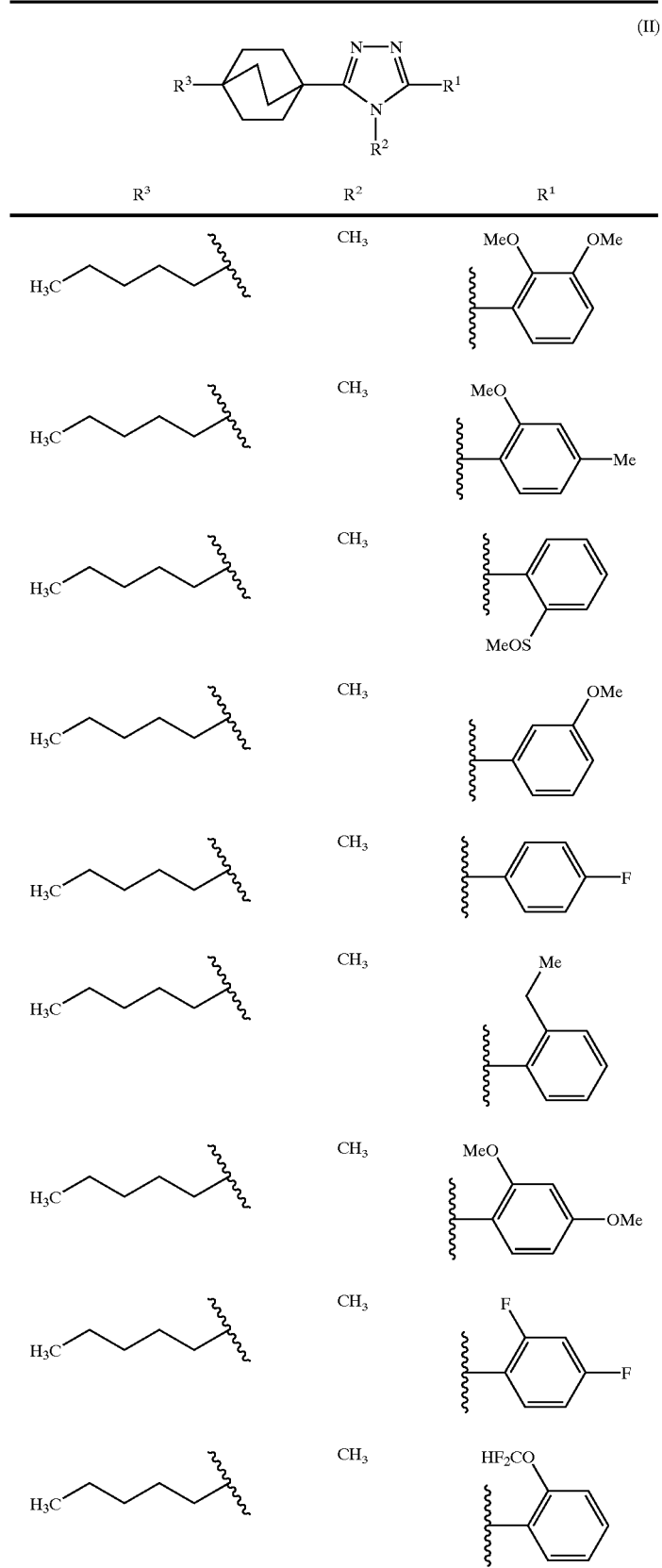

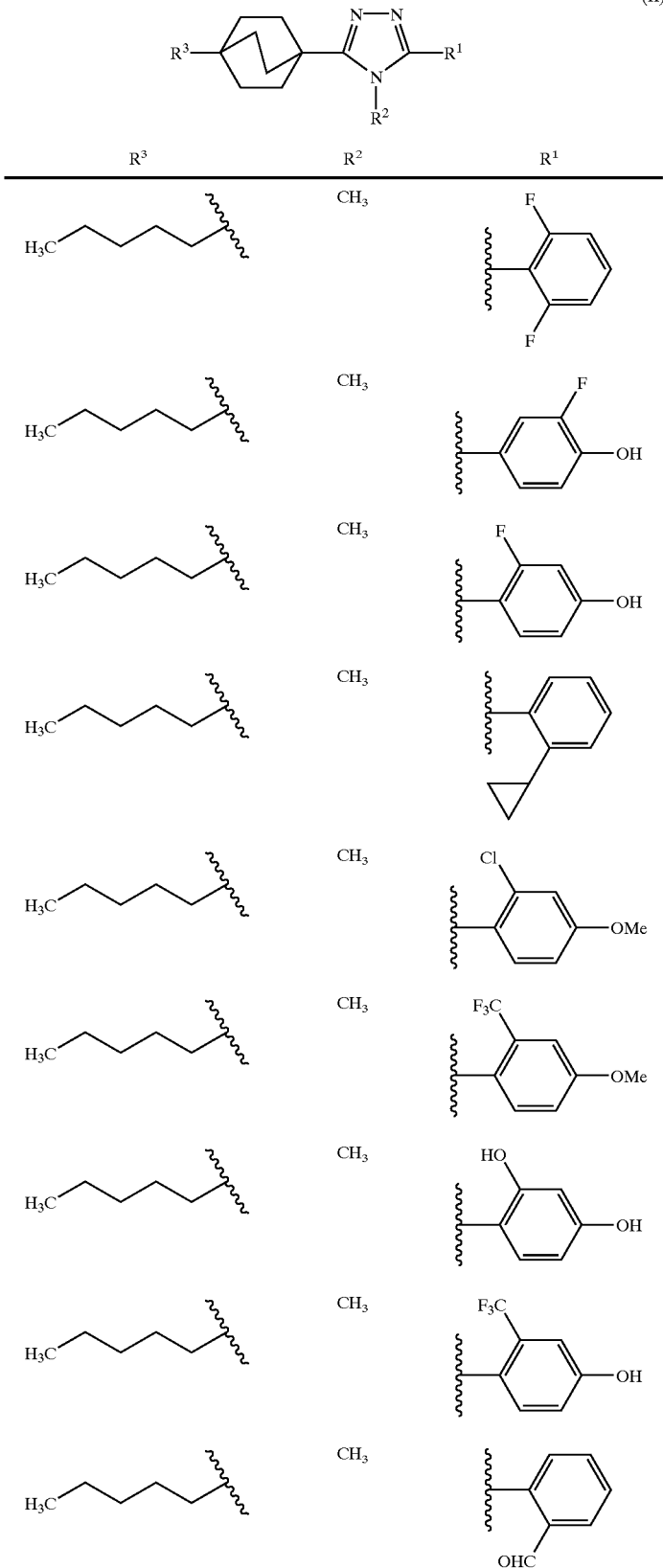

-continued
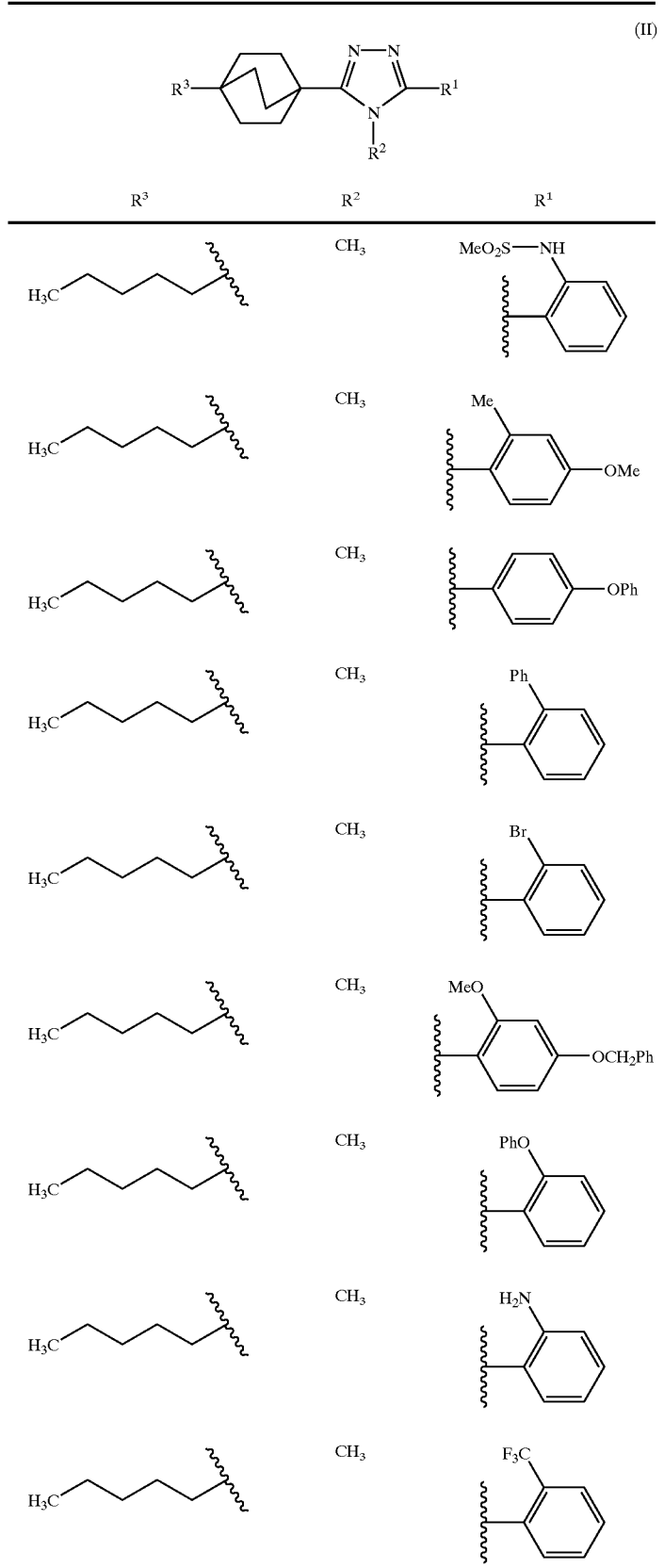

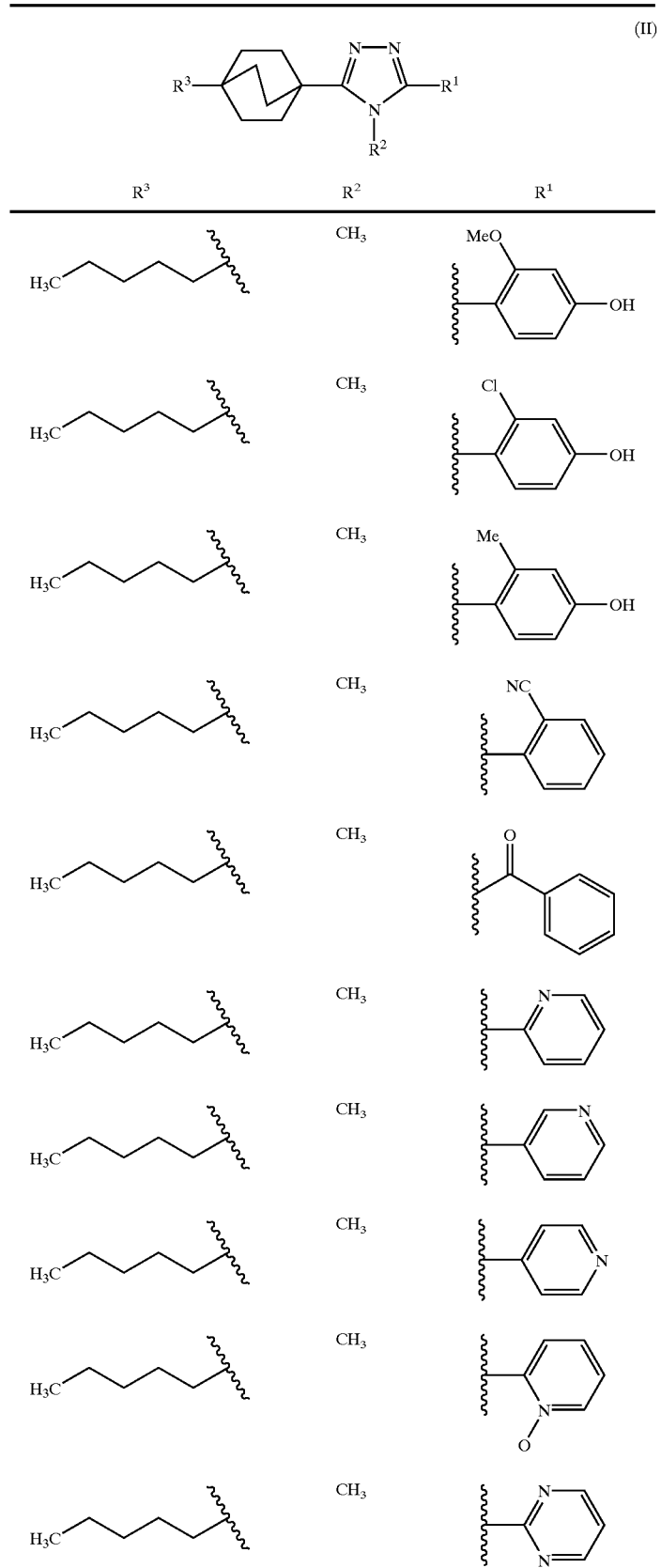

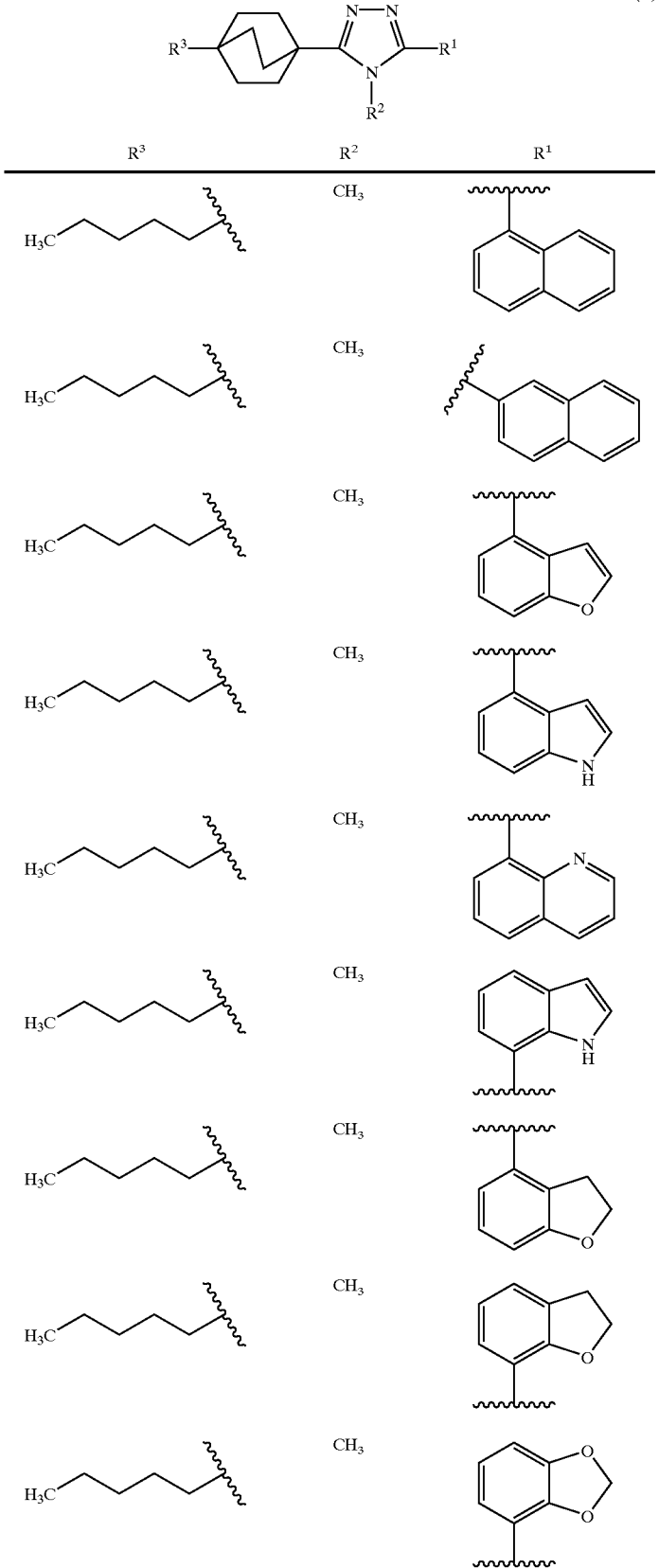

-continued
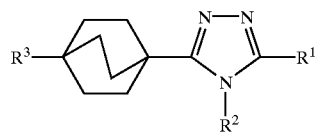
(II)
| R³ | R² | R¹ |
|---|---|---|
| 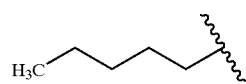 | CH₃ | 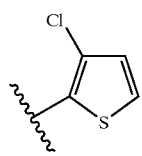 |
| 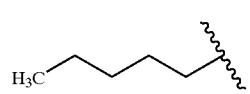 | CH₂CH₃ | 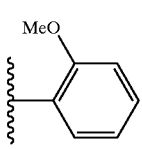 |
| 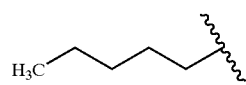 | CH₂CH₃ | 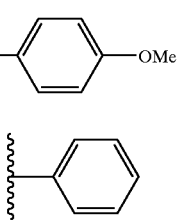 |
| 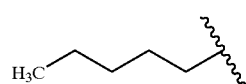 | CH₂CH₃ | 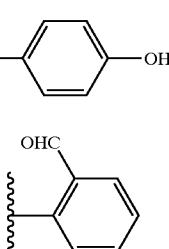 |
| 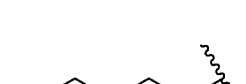 | CH₂CH₃ | 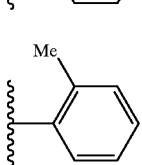 |
| 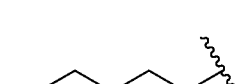 | CH₂CH₃ | 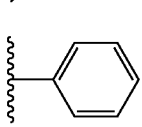 |
| 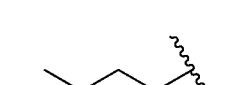 | CH₂CH₃ | 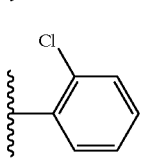 |
| 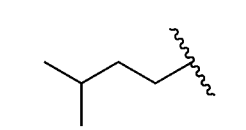 | CH₃ | 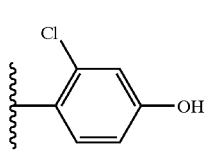 |
| | CH₃ | |

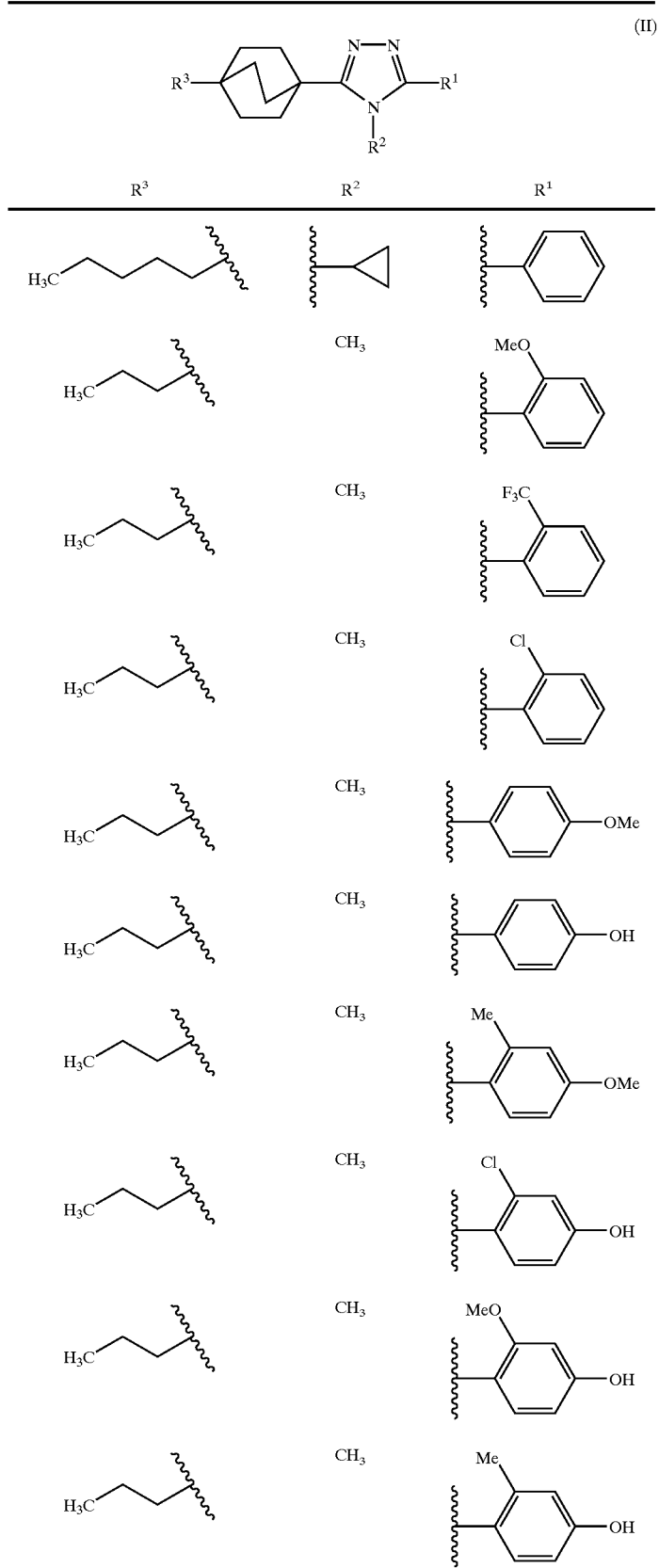

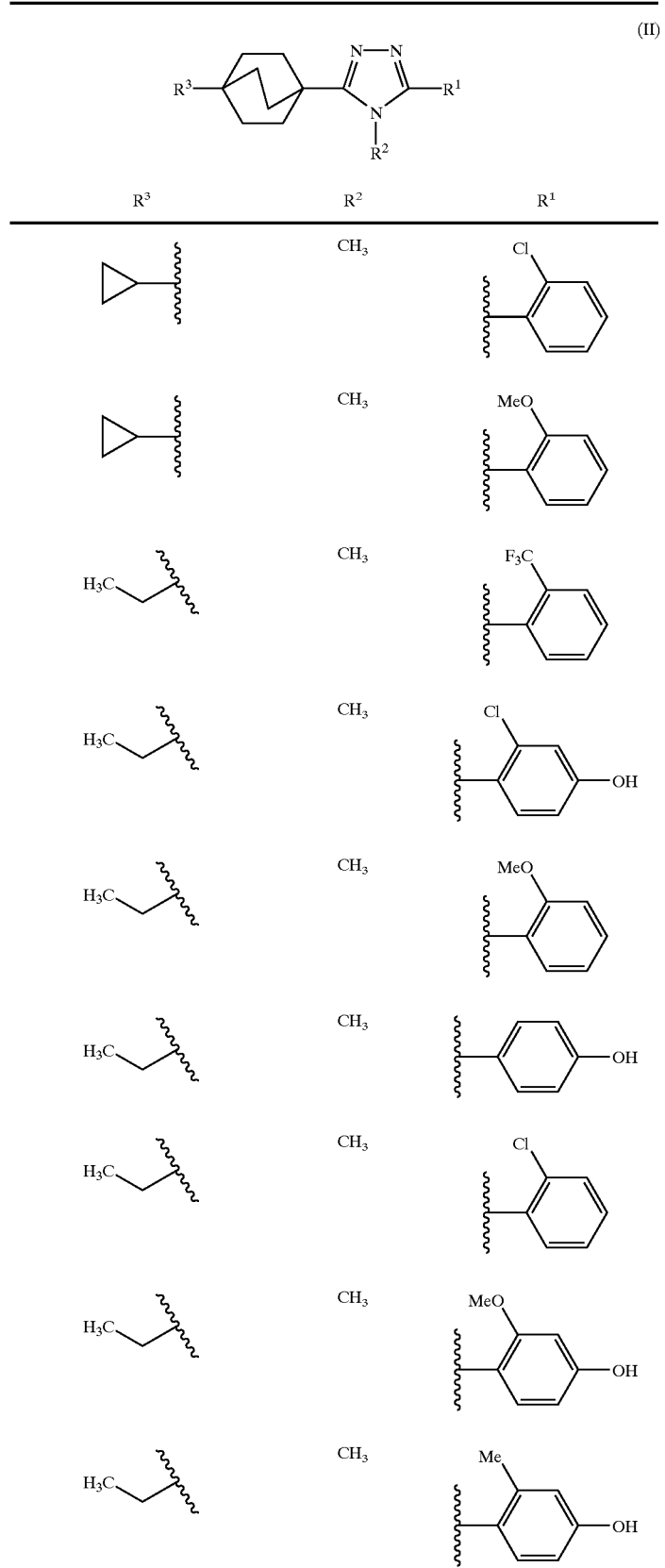

-continued
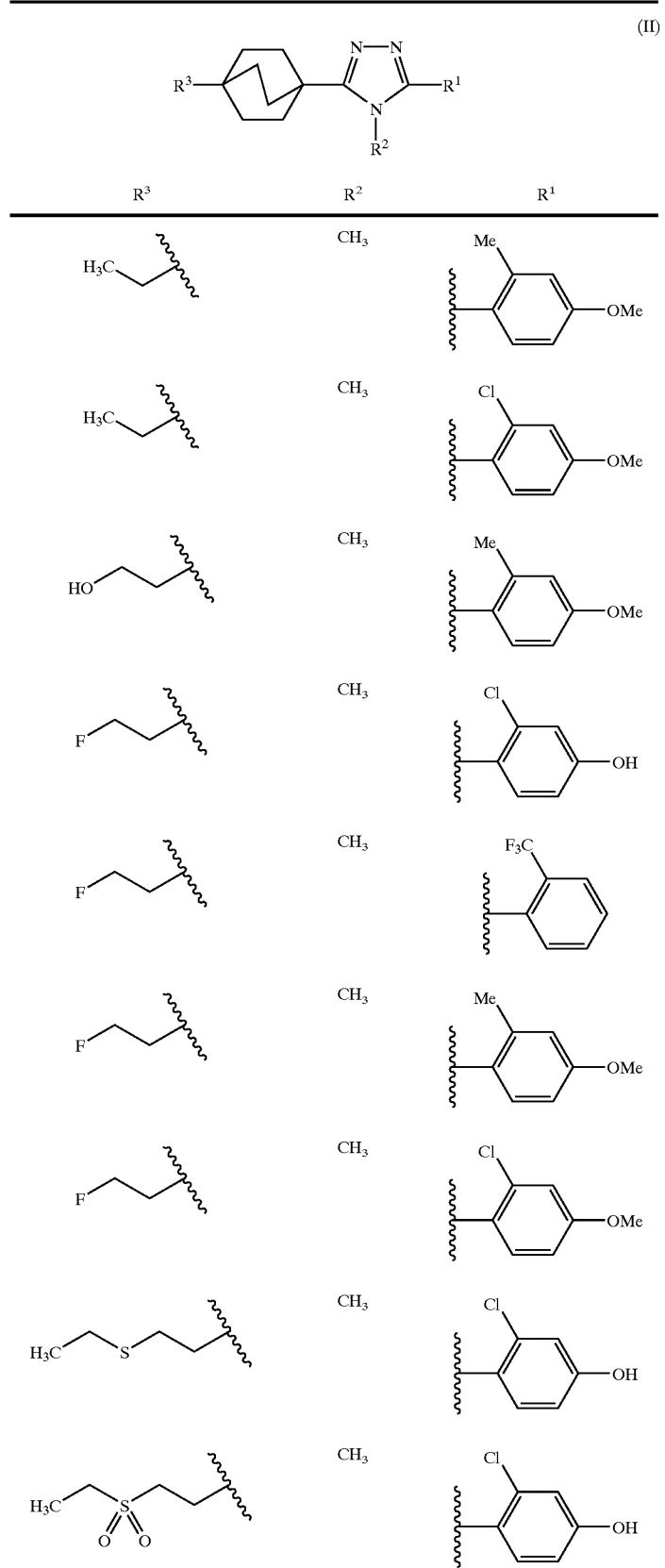

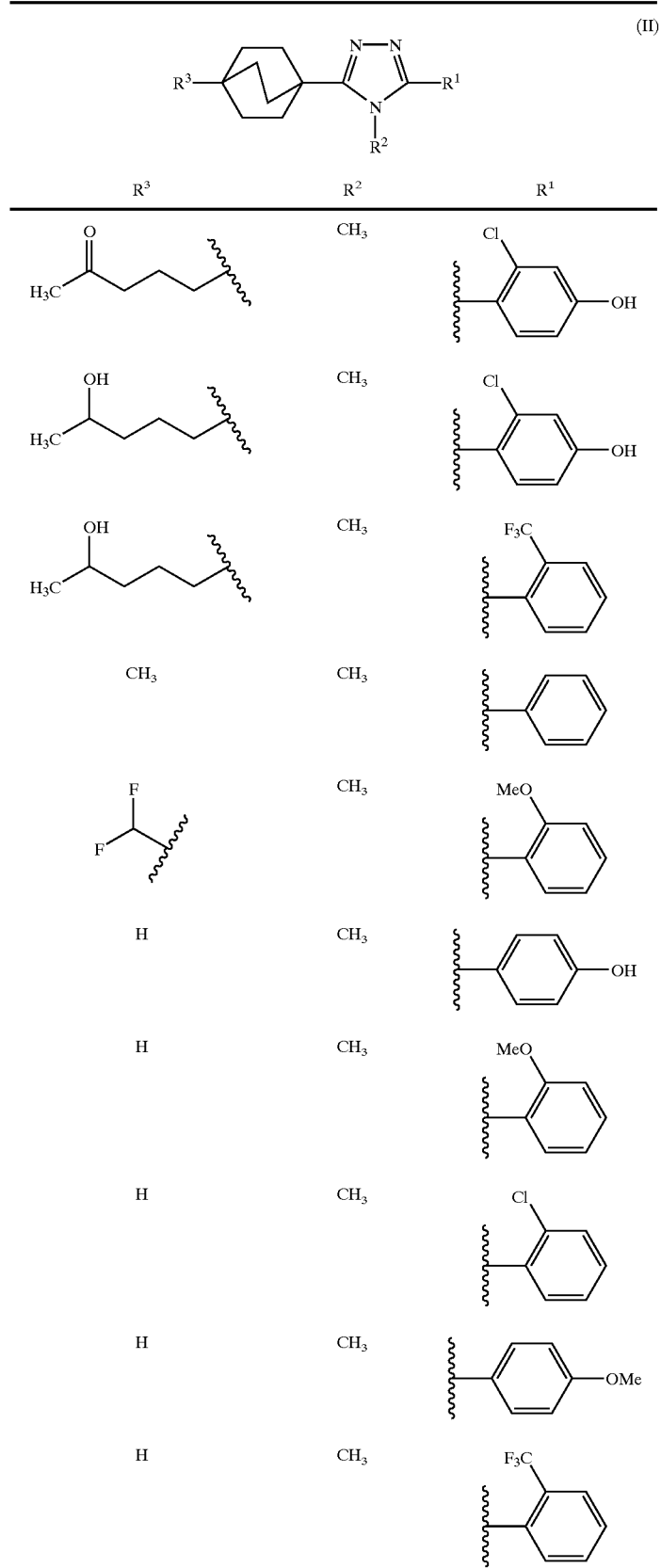

-continued (II) Structure: R³-[bicyclooctyl]-[1,2,4-triazole with R¹ at 3-position and R² on N4]

| R³ | R² | R¹ |
|---|---|---|
| phenyl | CH₃ | phenyl |
| phenyl | CH₃ | 2-methoxyphenyl |
| phenyl | CH₃ | 2-methylphenyl |
| phenyl | CH₃ | 2-trifluoromethyl-4-hydroxyphenyl |
| phenyl | CH₃ | 4-hydroxyphenyl |
| 4-(MeO₂S)phenyl | CH₃ | 2-trifluoromethylphenyl |
| 5-bromopyrimidin-2-ylamino | CH₃ | 2-methoxyphenyl |
| 5-bromopyrimidin-2-ylamino | CH₃ | 4-hydroxyphenyl |
| MeO-C(=O)- | CH₃ | phenyl |
| CbzNH— | CH₃ | 2-methoxyphenyl |

-continued
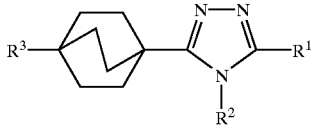
(II)
| R³ | R² | R¹ |
|---|---|---|
| NH₂ | CH₃ |  |
|  | CH₃ |  |
|  | CH₃ | 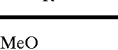 |
|  | CH₃ | 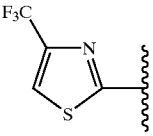 |
|  | CH₃ |  |
|  | CH₃ | 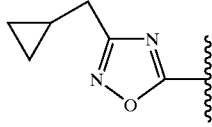 |
|  | CH₃ | 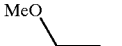 |
|  | CH₃ | 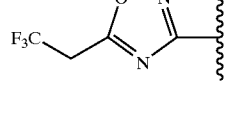 |
|  | CH₃ | 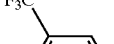 |

-continued (II)

| R³ | R² | R¹ |
|---|---|---|
| Me-SO₂-CH₂CH₂- | CH₃ | 2-(CF₃)C₆H₄- |
| iPr-SO₂-CH₂CH₂- | CH₃ | 2-(CF₃)C₆H₄- |
| Me-CH₂-SO₂-CH₂- | CH₃ | 2-(CF₃)C₆H₄- |
| Et-SO₂-CH₂CH₂CH₂- | CH₃ | 2-(CF₃)C₆H₄- |
| Me-CH₂-S(O)-CH₂CH₂- | CH₃ | 2-(CF₃)C₆H₄- |
| Me-CH₂CH₂-SO₂-CH₂CH₂- | CH₃ | 2-(CF₃)C₆H₄- |
| tBu-SO₂-CH₂CH₂- | CH₃ | 2-(CF₃)C₆H₄- |
| Ph-SO₂-CH₂- | CH₃ | 2-(CF₃)C₆H₄- |
| 4-F-C₆H₄-SO₂-CH₂- | CH₃ | 2-(CF₃)C₆H₄- |

-continued
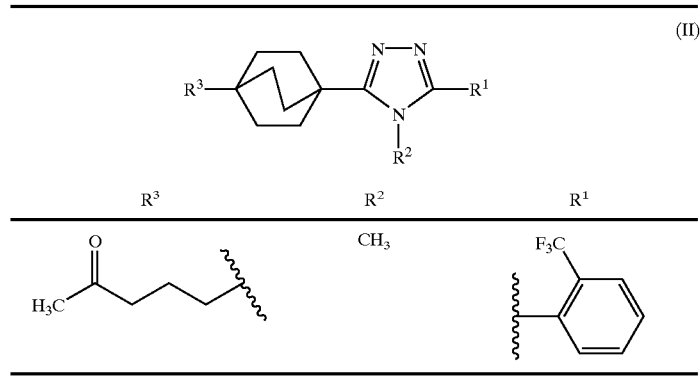
or a pharmaceutically acceptable salt thereof.
21. A compound of structural formula III selected from the group consisting of:
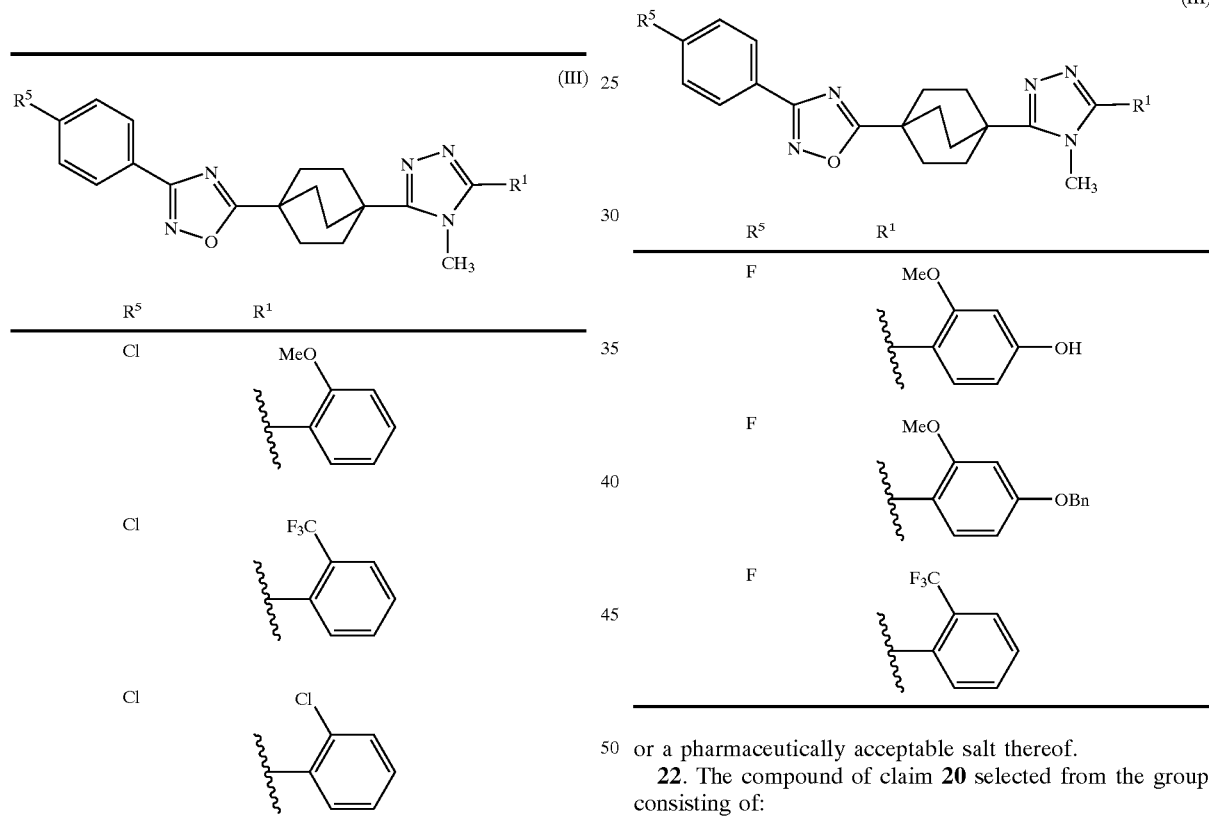
or a pharmaceutically acceptable salt thereof.
22. The compound of claim 20 selected from the group consisting of:
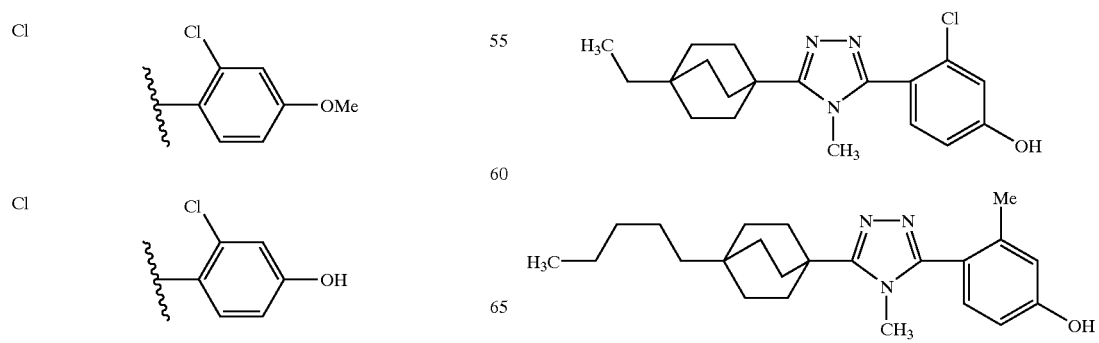

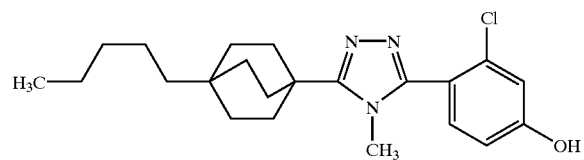
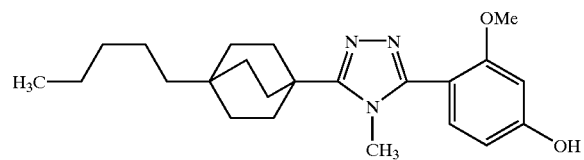
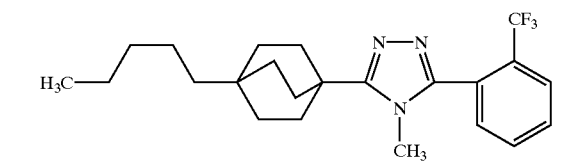
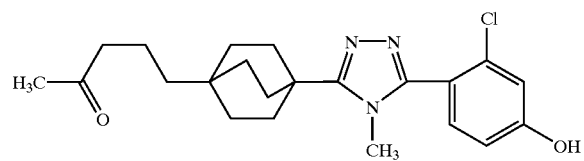
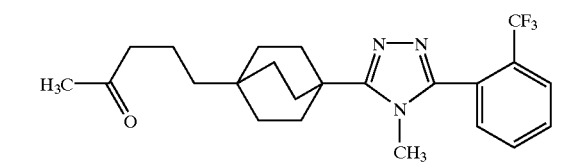
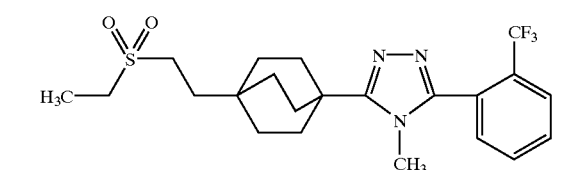
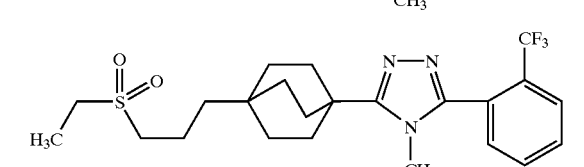
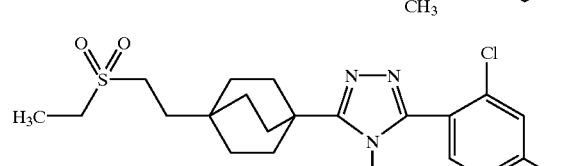
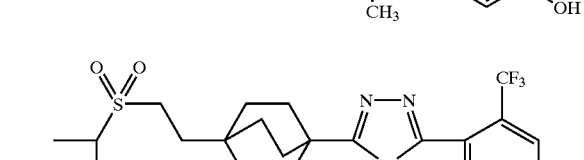
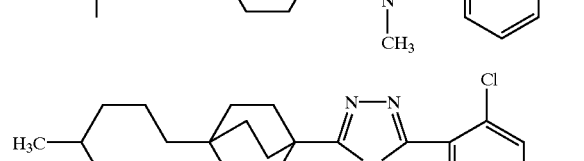
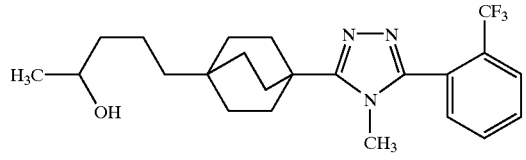
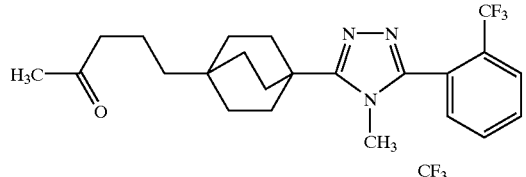
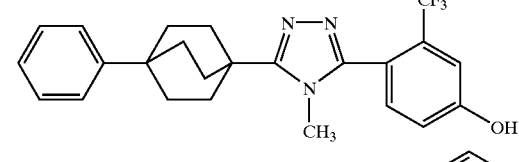
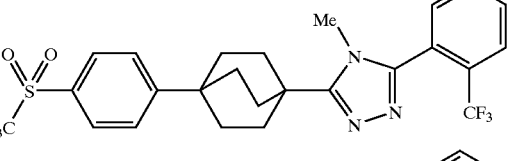
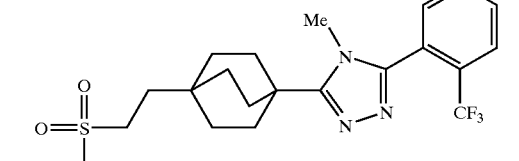
or a pharmaceutically acceptable salt thereof.
23. The compound of claim 21 which is
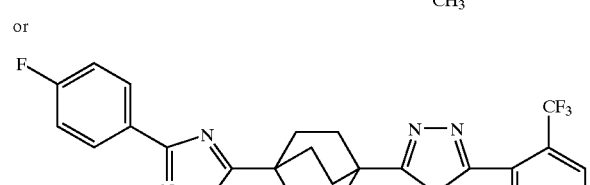
or
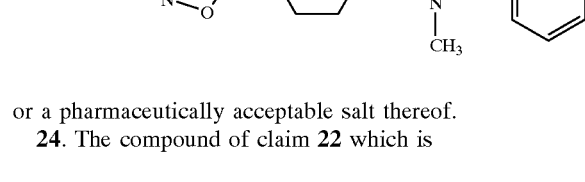
or a pharmaceutically acceptable salt thereof.
24. The compound of claim 22 which is
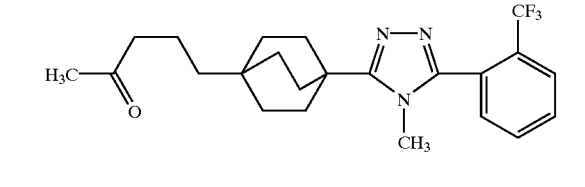
or a pharmaceutically acceptable salt thereof.

25. The compound of claim 22 which is

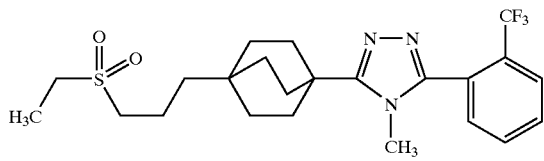

or a pharmaceutically acceptable salt thereof.

26. The compound of claim 22 which is

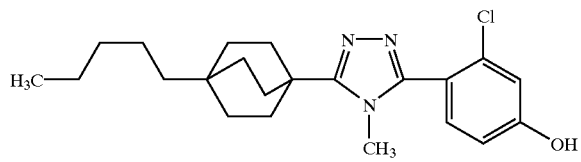

or a pharmaceutically acceptable salt thereof.

27. The compound of claim 22 which is

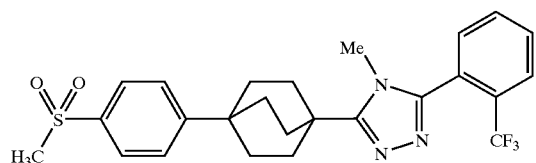

or a pharmaceutically acceptable salt thereof.

28. A pharmaceutical composition comprising a compound in accordance with claim 1 in combination with a pharmaceutically acceptable carrier.

29. A method of treating hyperglycemia, diabetes or insulin resistance in a mammalian patient in need of such treatment which comprises administering to said patient an effective amount of a compound in accordance with claim 1.

30. A method of treating non-insulin dependent diabetes mellitus in a mammalian patient in need of such treatment comprising administering to the patient an anti-diabetic effective amount of a compound in accordance with claim 1.

31. A method of treating obesity in a mammalian patient in need of such treatment compriseing administering to said patient a compound in accordance with claim 1 in an amount that is effective to treat obesity.

32. A method of treating Syndrome X in a mammalian patient in need of such treatment, comprising administering to said patient a compound in accordance with claim 1 in an amount that is effective to treat Syndrome X.

33. A method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound in accordance with claim 1 in an amount that is effective to treat said lipid disorder.

34. A method of treating atherosclerosis in a mammalian patient in need of such treatment, comprising administering to said patient a compound in accordance with claim 1 in an amount effective to treat atherosclerosis.

35. A method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with claim 1 in an amount that is effective to treat said condition.

36. A method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need of such treatment, comprising administering to the patient a compound in accordance with claim 1 in an amount that is effective to delay the onset of said condition.

37. A method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need of such treatment, comprising administering to the patient a compound in accordance with claim 1 in an amount that is effective to reduce the risk of developing said condition.

38. A method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient an effective amount of a compound as defined in claim 1, and a compound selected from the group consisting of:
  (a) DP-IV inhibitors;
  (b) insulin sensitizers selected from the group consisting of (i) PPAR agonists and (ii) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 mimetics, and GLP-1 receptor agonists;
  (h) GIP,GIP mimetics, and GIP receptor agonists;
  (i) PACAP, PACAP mimetics, and PACAP receptor 3 agonists;
  (j) cholesterol lowering agents selected from the group consisting of (i) HMG-CoA reductase inhibitors, (ii)

sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferdse inhibitors, and (viii) anti-oxidants;

(k) PPARα agonists;
(l) antiobesity compounds;
(m) ileal bile acid transporter inhibitors;
(n) anti-inflammatory agents excluding glucocorticoids;
(o) protein tyrosine phosphatase-1B (PTP-1B) inhibitors; and
(p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan;

said compounds being administered to the patient in an amount that is effective to treat said condition.

39. A method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a therapeutically effective amount of a compound as defined in claim 1 and an HMG-CoA reductase inhibitor.

40. The method of claim 39 wherein the HMG-CoA reductase inhibitor is a statin.

41. The method of claim 40 wherein the statin is selected from the group consisting of lovastatin, simvastatin, pravastatin, fluvastatin, atorvastatin, itavastatin, ZD-4522 and rivastatin.

42. A method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound as defined in claim 1 and an HMG-CoA reductase inhibitor.

43. A method for delaying the onset or reducing the risk of developing atherosclerosis in a human patient in need of such treatment comprising administering to said patient an effective amount of a compound as defined in claim 1 and an HMG-CoA reductase inhibitor.

44. The method of claim 42 wherein the HMG-CoA reductase inhibitor is a statin.

45. The method of claim 44 wherein the statin is selected from the group consisting of lovastatin, simvastatin, pravastatin, fluvastatin, atorvastatin, itavastatin, ZD-4522 and rivastatin.

46. The method of claim 45 wherein the statin is simvastatin.

47. The method of claim 46 further comprising administering a cholesterol absorption inhibitor.

48. The method of claim 47 wherein the cholesterol absorption inhibitor is ezetimibe.

49. A pharmaceutical composition comprising
(1) a compound according to claim 1,
(2) a compound selected from the group consisting of:
    (a) DP-IV inhibitors;
    (b) insulin sensitizers selected from the group consisting of (i) PPAR agonists and (ii) biguanides;
    (c) insulin and insulin mimetics;
    (d) sulfonylureas and other insulin secretagogues;
    (e) α-glucosidase inhibitors;
    (f) glucagon receptor antagonists;
    (g) GLP-1, GLP-1 mimetics, and GLP-1 receptor agonists;
    (h) GIP, GIP mimetics, and GIP receptor agonists;
    (i) PACAP, PACAP mimetics, and PACAP receptor 3 agonists;
    (j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
    (k) PPARSδ agonists;
    (l) antiobesity compounds;
    (m) ileal bile acid transporter inhibitors;
    (n) anti-inflammatory agents other than glucocorticoids;
    (o) protein tyrosine phosphatase-1B (PTP-1B) inhibitors; and
    (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and
(3) a pharmaceutically acceptable carrier.

* * * * *

UNITED STATES PATENT AND TRADEMARK OFFICE
CERTIFICATE OF CORRECTION

PATENT NO.         : 6,849,636 B2  Page 1 of 1
APPLICATION NO. : 10/739716
DATED              : February 1, 2005
INVENTOR(S)        : Sherman T. Waddell et al.

It is certified that error appears in the above-identified patent and that said Letters Patent is hereby corrected as shown below:

(1) Col. 138 in claims 35 and 38, lines 2 & 45, delete "(16) neurodegenerative disease".

(2) Col. 138 in claims 36 and 37, lines 15 & 31, delete "(16) neurodegenerative disease".

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

PATENT NO.      : 6,849,636 B2
APPLICATION NO. : 10/739716
DATED           : February 1, 2005
INVENTOR(S)     : Sherman T. Waddell et al.

It is certified that error appears in the above-identified patent and that said Letters Patent is hereby corrected as shown below:

(1)  Replace claims 35-38 with the following text:

35. A method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension and other conditions and disorders where insulin resistance is a component, in a mammalian patient in need of such treatment, comprising administering to the patient a compound in accordance with claim 1 in an amount that is effective to treat said condition.

36. A method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension and other conditions and disorders where insulin resistance is a component in a mammalian patient in need of such treatment, comprising administering to the patient a compound in accordance with claim 1 in an amount that is effective to delay the onset of said condition.

37. A method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension and other conditions and disorders where insulin resistance is a component in a mammalian patient in need of such treatment, comprising administering to the patient a compound in accordance with claim 1 in an amount that is effective to reduce the risk of developing said condition.

38. A method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension

UNITED STATES PATENT AND TRADEMARK OFFICE
CERTIFICATE OF CORRECTION

PATENT NO.        : 6,849,636 B2
APPLICATION NO. : 10/739716
DATED             : February 1, 2005
INVENTOR(S)       : Sherman T. Waddell et al.

It is certified that error appears in the above-identified patent and that said Letters Patent is hereby corrected as shown below:

and other conditions and disorders where insulin resistance is a component, in a mammalian patient in need of such treatment, comprising administering to the patient an effective amount of a compound as defined in claim 1, and a compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) .alpha.-glucosidase inhibitors; (f) glucagon receptor antagonists; (g) GLP-1 GLP-1 mimetics, and GLP-1 receptor agonists; (h) GIP,GIP mimetics, and GIP receptor agonists; (i) PACAP, PACAP mimetics, and PACAP receptors 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPAR.alpha. agonists, (v) PPAR.alpha./.gamma. dual agonists, (vi) inhibitors of cholesterol absorption, (vii) acyl CoA:cholesterol acyltransferdse inhibitors, and (viii) anti-oxidants; (k) PPAR.alpha. agonists; (l) antiobesity compounds; (m) ileal bile acid transporter inhibitors; (n)
anti-inflammatory agents excluding glucocorticoids; (o) protein tyrosine phosphatase-1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan;

said compounds being administered to the patient in an amount that is effective to treat said condition.

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 6,849,636 B2
APPLICATION NO. : 10/739716
DATED : February 1, 2005
INVENTOR(S) : Sherman T. Waddell et al.

It is certified that error appears in the above-identified patent and that said Letters Patent is hereby corrected as shown below:

Column 137, line 62 thru Column 139, line 22, (1) Replace claims 35-38 with the following text:

35. A method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension and other conditions and disorders where insulin resistance is a component, in a mammalian patient in need of such treatment, comprising administering to the patient a compound in accordance with claim 1 in an amount that is effective to treat said condition.

36. A method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension and other conditions and disorders where insulin resistance is a component in a mammalian patient in need of such treatment, comprising administering to the patient a compound in accordance with claim 1 in an amount that is effective to delay the onset of said condition.

37. A method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension and other conditions and disorders where insulin resistance is a component in a mammalian patient in need of such treatment, comprising administering to the patient a compound in accordance with claim 1 in an amount that is effective to reduce the risk of developing said condition.

UNITED STATES PATENT AND TRADEMARK OFFICE
CERTIFICATE OF CORRECTION

PATENT NO. : 6,849,636 B2
APPLICATION NO. : 10/739716
DATED : February 1, 2005
INVENTOR(S) : Sherman T. Waddell et al.

It is certified that error appears in the above-identified patent and that said Letters Patent is hereby corrected as shown below:

38. A method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) retinopathy, (17) nephropathy, (18) neuropathy, (19) Syndrome X, (20) hypertension and other conditions and disorders where insulin resistance is a component, in a mammalian patient in need of such treatment, comprising administering to the patient an effective amount of a compound as defined in claim 1, and a compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) .alpha.-glucosidase inhibitors; (f) glucagon receptor antagonists; (g) GLP-1 GLP-1 mimetics, and GLP-1 receptor agonists; (h) GIP,GIP mimetics, and GIP receptor agonists; (i) PACAP, PACAP mimetics, and PACAP receptors 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPAR.alpha. agonists, (v) PPAR.alpha./.gamma. dual agonists, (vi) inhibitors of cholesterol absorption, (vii) acyl CoA:cholesterol acyltransferdse inhibitors, and (viii) anti-oxidants; (k) PPAR.alpha. agonists; (l) antiobesity compounds; (m) ileal bile acid transporter inhibitors; (n)
anti-inflammatory agents excluding glucocorticoids; (o) protein tyrosine phosphatase-1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan;

UNITED STATES PATENT AND TRADEMARK OFFICE
CERTIFICATE OF CORRECTION

PATENT NO. : 6,849,636 B2
APPLICATION NO. : 10/739716
DATED : February 1, 2005
INVENTOR(S) : Sherman T. Waddell et al.

It is certified that error appears in the above-identified patent and that said Letters Patent is hereby corrected as shown below:

said compounds being administered to the patient in an amount that is effective to treat said condition.

This certificate supersedes the Certificate of Correction issued July 22, 2008.

Signed and Sealed this

Twelfth Day of August, 2008

JON W. DUDAS
*Director of the United States Patent and Trademark Office*